United States Patent
Laughlin et al.

(10) Patent No.: US 9,233,127 B2
(45) Date of Patent: Jan. 12, 2016

(54) COMPOSITIONS AND METHODS FOR CXCR4 SIGNALING AND UMBILICAL CORD BLOOD STEM CELL ENGRAFTMENT

(71) Applicant: University of Virginia Patent Foundation, Charlottesville, VA (US)

(72) Inventors: Mary J. Laughlin, Charlottesville, VA (US); Mariusz Z. Ratajczak, Charlottesville, VA (US); Claudio Brunstein, Minneapolis, MN (US)

(73) Assignee: University of Virginia Patent Foundation, Charlottesville, VA (US)

( * ) Notice: Subject to any disclaimer, the term of this patent is extended or adjusted under 35 U.S.C. 154(b) by 62 days.

(21) Appl. No.: 13/779,092

(22) Filed: Feb. 27, 2013

(65) Prior Publication Data
US 2013/0236425 A1    Sep. 12, 2013

Related U.S. Application Data

(60) Provisional application No. 61/605,035, filed on Feb. 29, 2012.

(51) Int. Cl.
*A61K 35/28* (2015.01)
*A61K 35/51* (2015.01)

(52) U.S. Cl.
CPC *A61K 35/28* (2013.01); *A61K 35/51* (2013.01)

(58) Field of Classification Search
None
See application file for complete search history.

(56) References Cited

U.S. PATENT DOCUMENTS 8,383,095 B2 *   2/2013   Christensen et al. ........ 424/93.1
2011/0305676 A1  12/2011  Zon et al.
2012/0003189 A1   1/2012  Pelus et al.

FOREIGN PATENT DOCUMENTS

WO    WO 2007/095594    *    8/2007

OTHER PUBLICATIONS

The Jackson Laboratory "Body Weight Information Jax® Mice Strain BALB/cJ" obtained from URL: http://jaxmice.jax.org/support/weight/000651.html on Jul. 17, 2015 (screen shot & enlarged table; 2 pages total).*
Delaney, C., et al., "Strategies to enhance umbilical cord blood stem cell engraftment in adult patients", Expert Rev. Hematol., Jun. 2010, vol. 3, No. 3, pp. 273-283.
Nauta, Alma J., et al., "Enhanced engraftment of umbilical cord blood-derived stem cells in NOD/SCID mice by cotransplantation of a second unrelated cord blood unit", Experimental Hematology, Oct. 2005, vol. 33, No. 10, pp. 1249-1256.
Fei, X.M., et al., "Co-culture of cord blood CD34(+) cells with human BM mesenchymal stromal cells enhances short-term engraftment of cord blood cells in NOD/SCID mice", Cytotherapy, 2007, vol. 9, No. 4, pp. 338-347.
Weitzel, R. Patrick, et al., "microRNA 184 regulates expression of NFAT1 in umbilical cord blood CD4+ T cells", Blood, Jun. 25, 2009, vol. 113, No. 26, pp. 6648-6657.
Ratajczak, M.Z., et al., "Transplantation studies in C3-deficient animals reveal a novel role of the third complement component (C3) in engraftment of bone marrow cells", Leukemia, 2004, 18, pp. 1482-1490.
Marquez-Curtis, Leah A., et al., "The Ins and Outs of Hematopoietic Stem Cells: Studies to Improve Transplantation Outcomes", Stem Cell Rev. and Rep., DOI 10.1007/s12015-010-9212-8, Sep. 2011 vol. 7, No. 3, pp. 590-607.
Reca, Ryan, et al., Functional receptor for C3a anaphylatoxin is expressed by normal hematopoietic stem/progenitor cells, and C3a enhances their homing-related responses to SDF-1, Blood, May 15, 2003, vol. 101, No. 10, pp. 3784-3793.
Wysoczynski, Marcin, et al., "Incorporation of CXCR4 into membrane lipid rafts primes homing-related responses of hematopoietic stem/progenitor cells to an SDF-1 gradient", Blood, Jan. 1, 2005, vol. 105, No. 1, pp. 40-48.
Shirvaikar, Neeta, et al., "Hyaluronic Acid and Thrombin Upregulate MT1-MMP Through P13K and Rac-1 Signaling and Prime the Homing-Related Responses of Cord Blood Hematopoietic Stem/Progenitor Cells", Stem Cells and Development, vol. 20, No. 1, 2011, pp. 19-30.
Ratajczak, M.Z., et al., "Reply to 'C5L2 receptor is not involved in C3a/C3a-desArg-mediated enhancement of bone marrow hematopoietic cell migration to CXCL12' by Honczarenko, et al., "Leukemia (2005), 19, pp. 1684-1685.

* cited by examiner

*Primary Examiner* — Allison Fox
(74) *Attorney, Agent, or Firm* — Rodney L. Sparks

(57) ABSTRACT

The present invention provides for enhancing engraftment by co-infusing at least two partially HLA matched umbilical cord blood ("UCB") units. The invention further provides for positive C3a mediated priming on responsiveness to doses of SDF-1 and C3a induced incorporation of CXCR4 in membranes in HSC and progenitors. The invention further provides for enhancing the homing of UCB HSC and progenitors via the SDF-1/CXCR4 pathway and that C3a and LL-37 are useful for this method. It is also disclosed herein that fragments of C3a (e.g., des-Arg) are effective in the methods of the invention, including enhancing homing of HSPCs to BM. The invention further encompasses the disclosure herein of NFAT1 regulation post-transcriptionally by both mir-184 and IFN-γ. The present invention further provides for measuring and using differences between UCB and adult CD4+/45RA+ T-cells as a means of defining strategies to enhance optimal allogeneic stem cell transplantation outcomes. The present invention further provides methods for maintaining IL-2 production in the absence of NFAT1 normal protein levels.

21 Claims, 60 Drawing Sheets

Figure 2. Improvement on Engraftment after Myeloablation with Double Umbilical Cord Transplantation

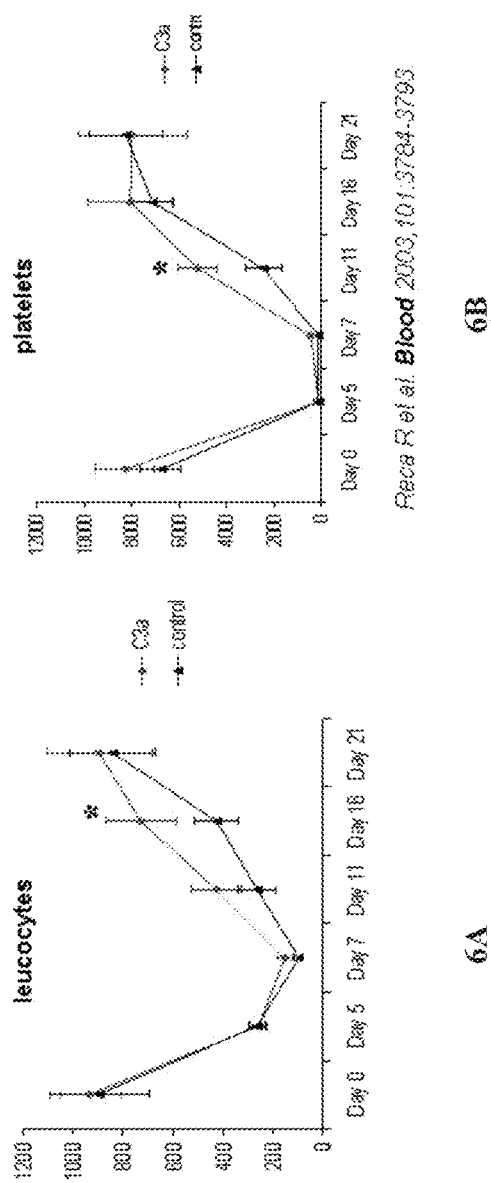
FIG. 6A-B

A) BM monuclear cell and B) CFU-GM migration in
response to an SDF-1 gradient after priming with LL-37 or hBD-2.
Values are fold increases of migrated cells compared to media alone

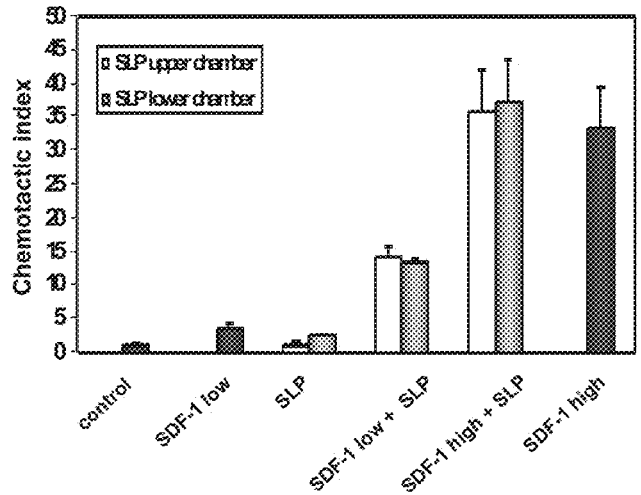
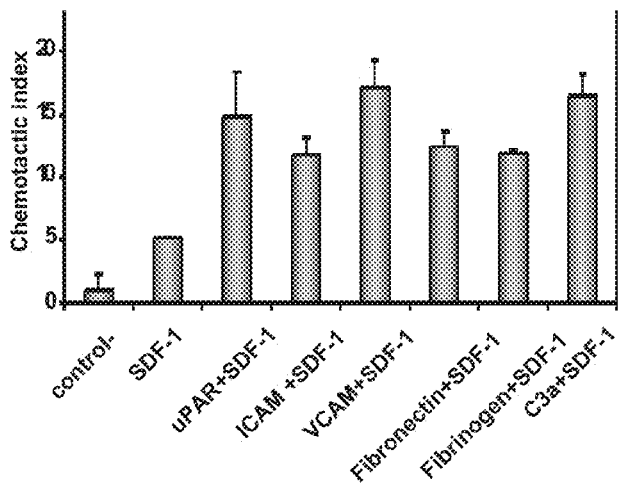
FIG. 11A-B. Effect of SLP and its components on chemotaxis of CD34+ cells.

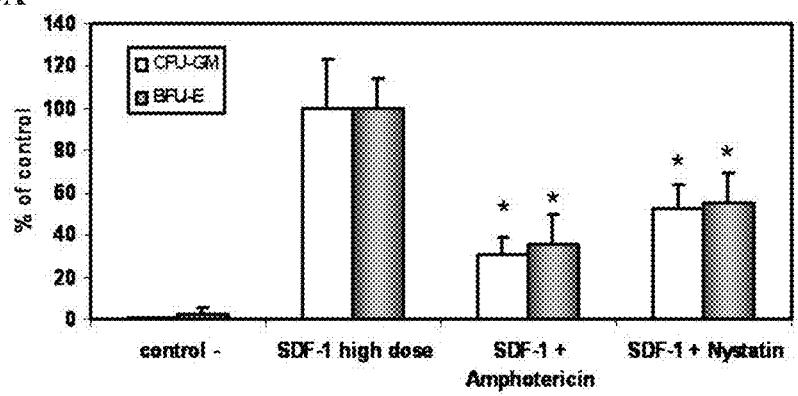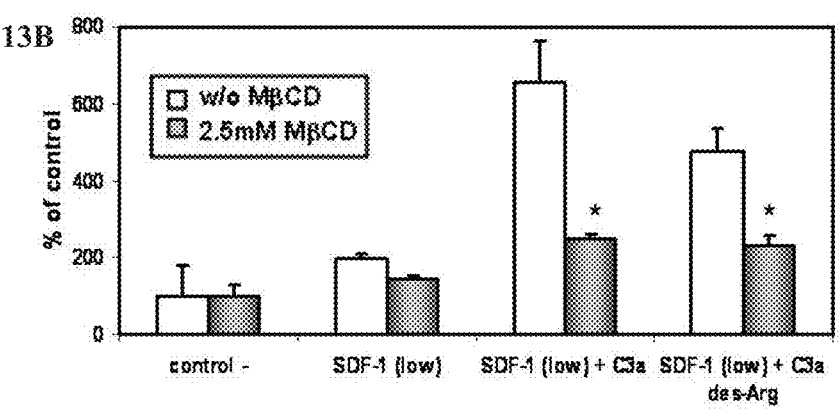
FIG. 13A-B

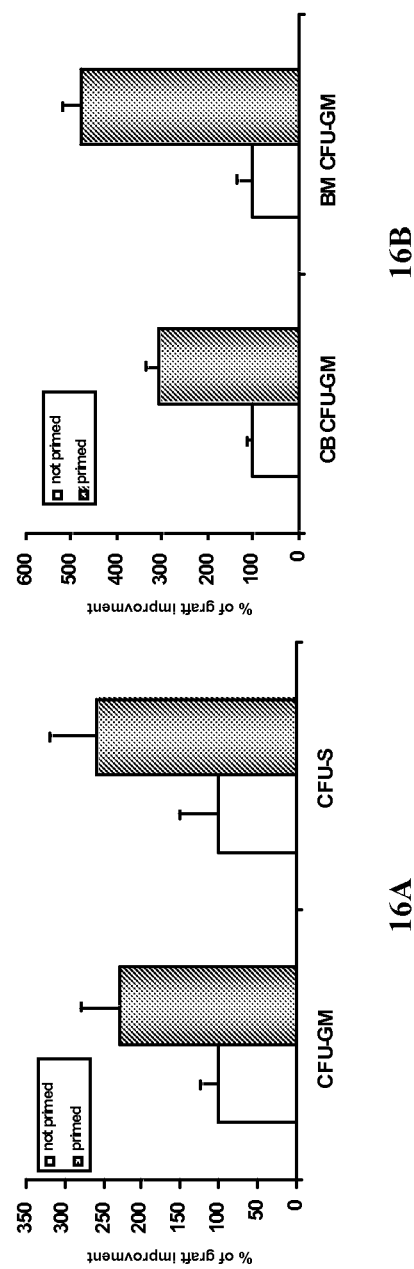
FIG. 16A-B

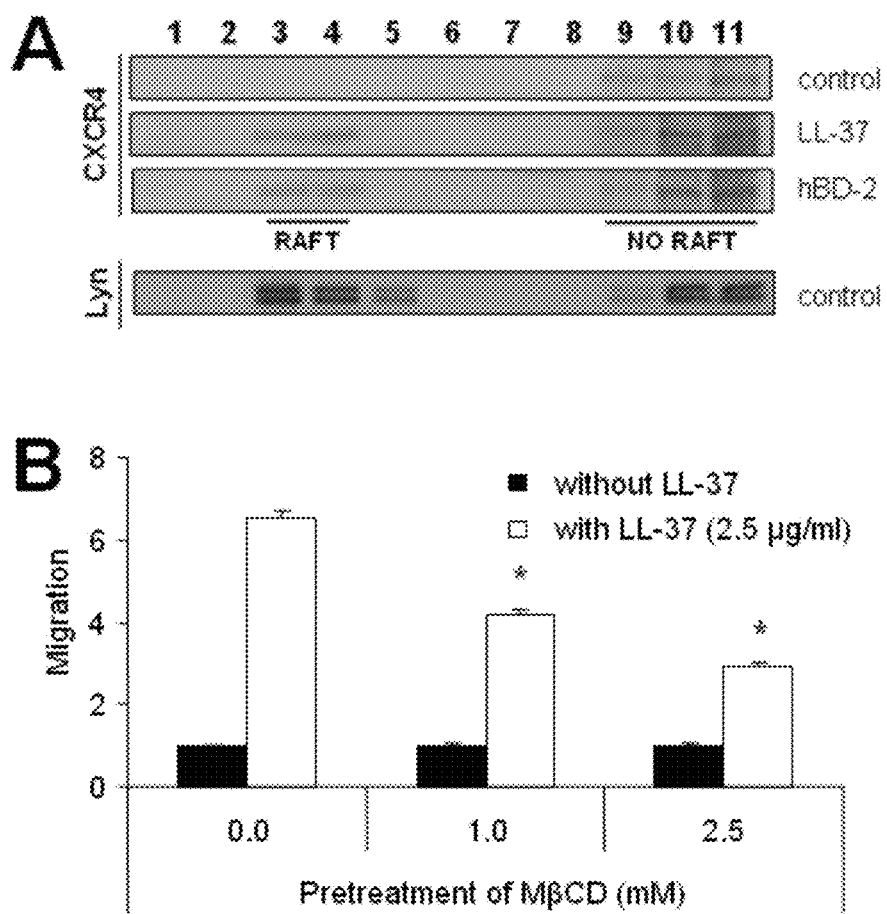
FIG. 18A-B

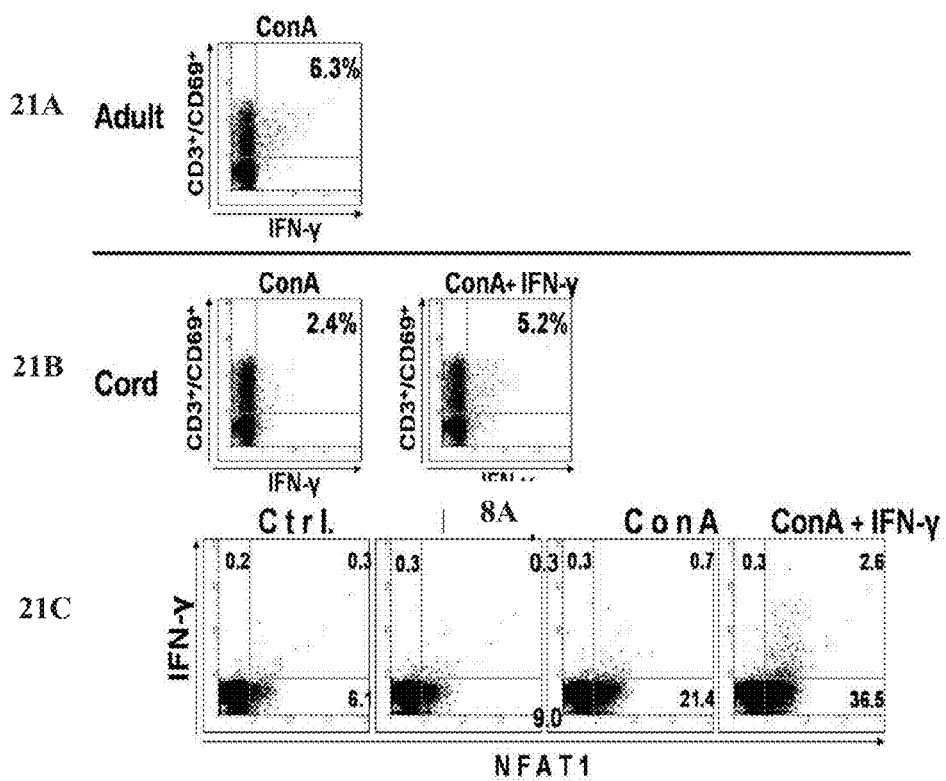
FIG. 21A-C

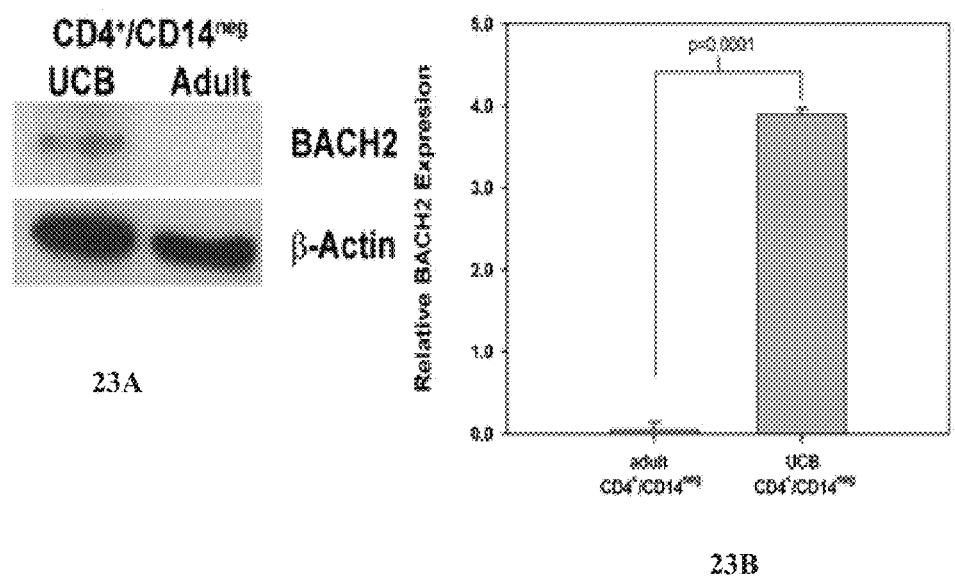
FIG. 23A-B

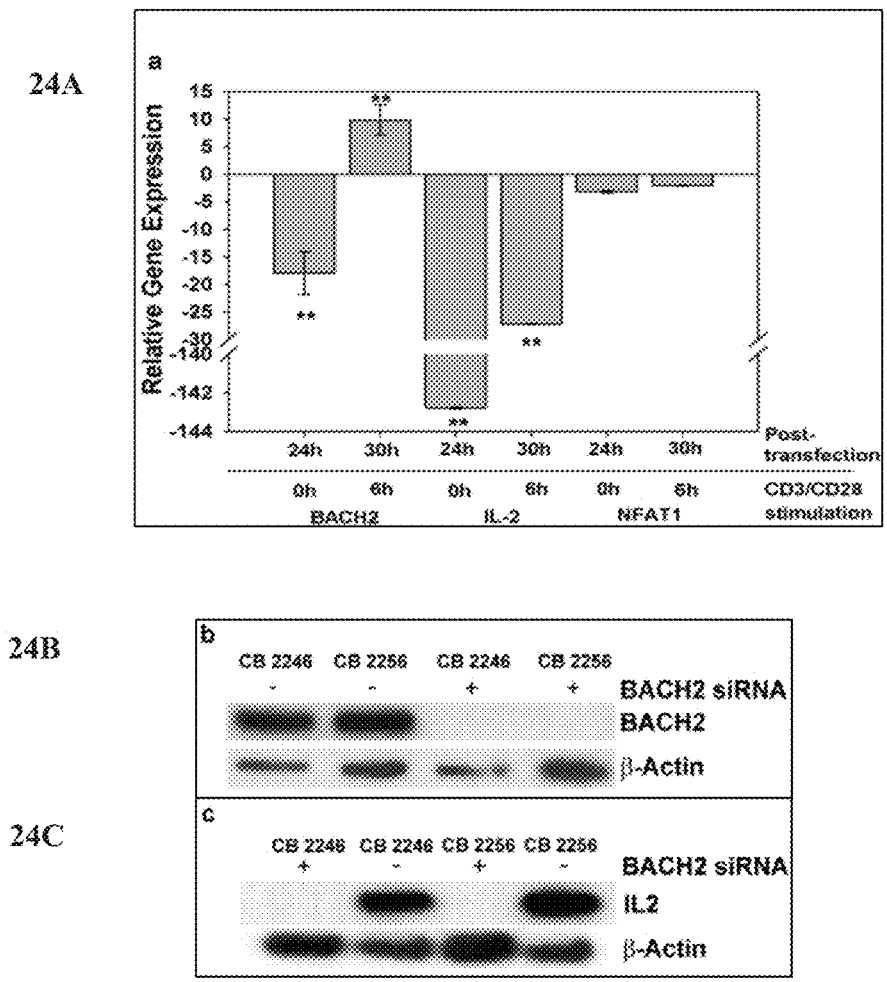
FIG. 24A-C

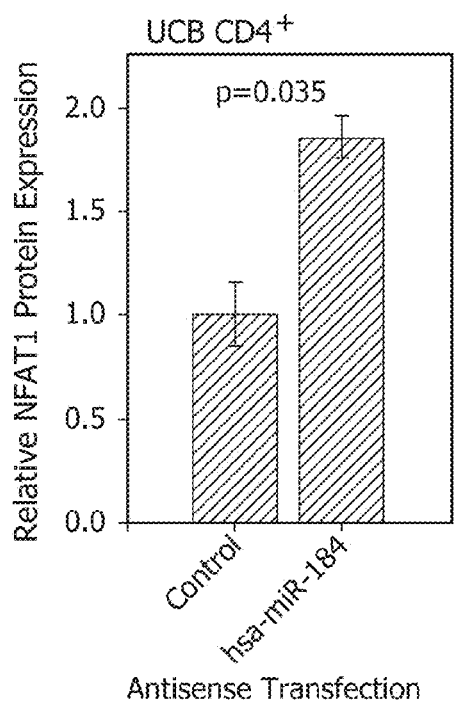
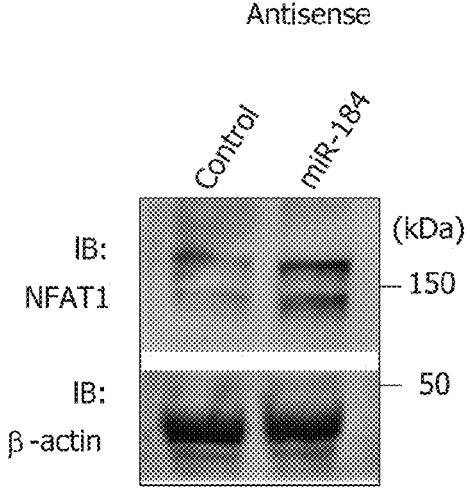
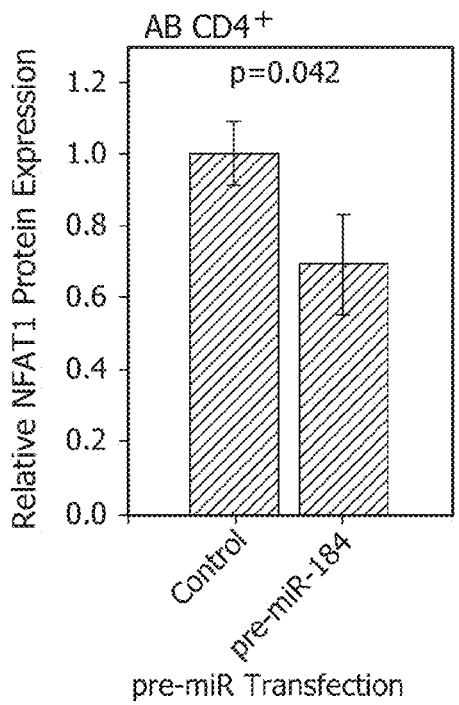
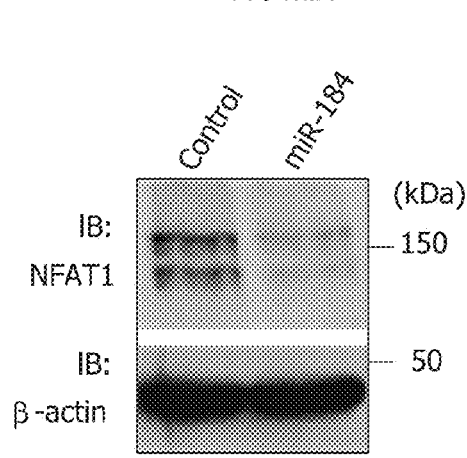
FIG. 27A-B

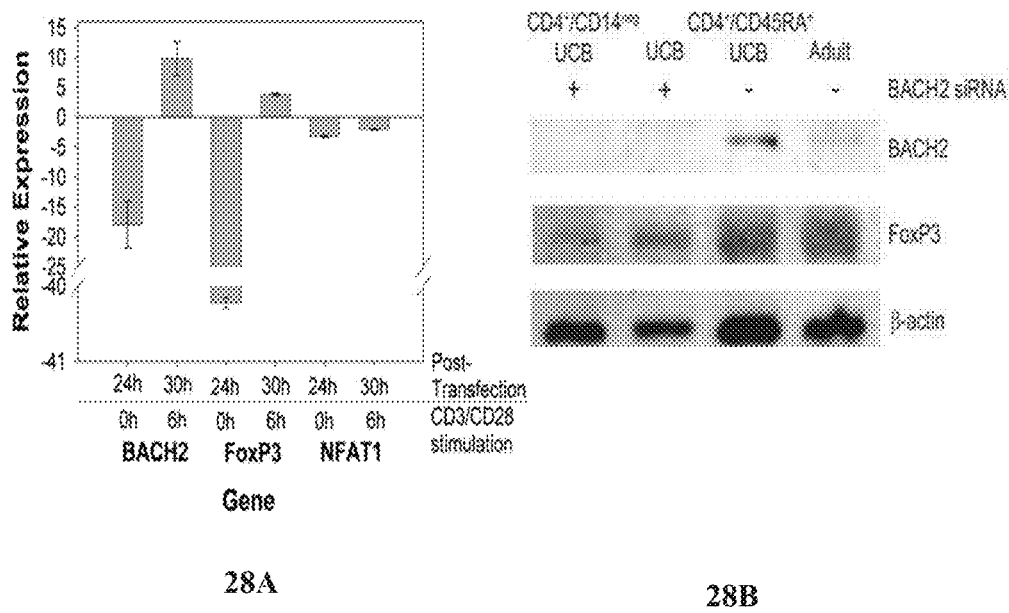
FIG. 28A-B

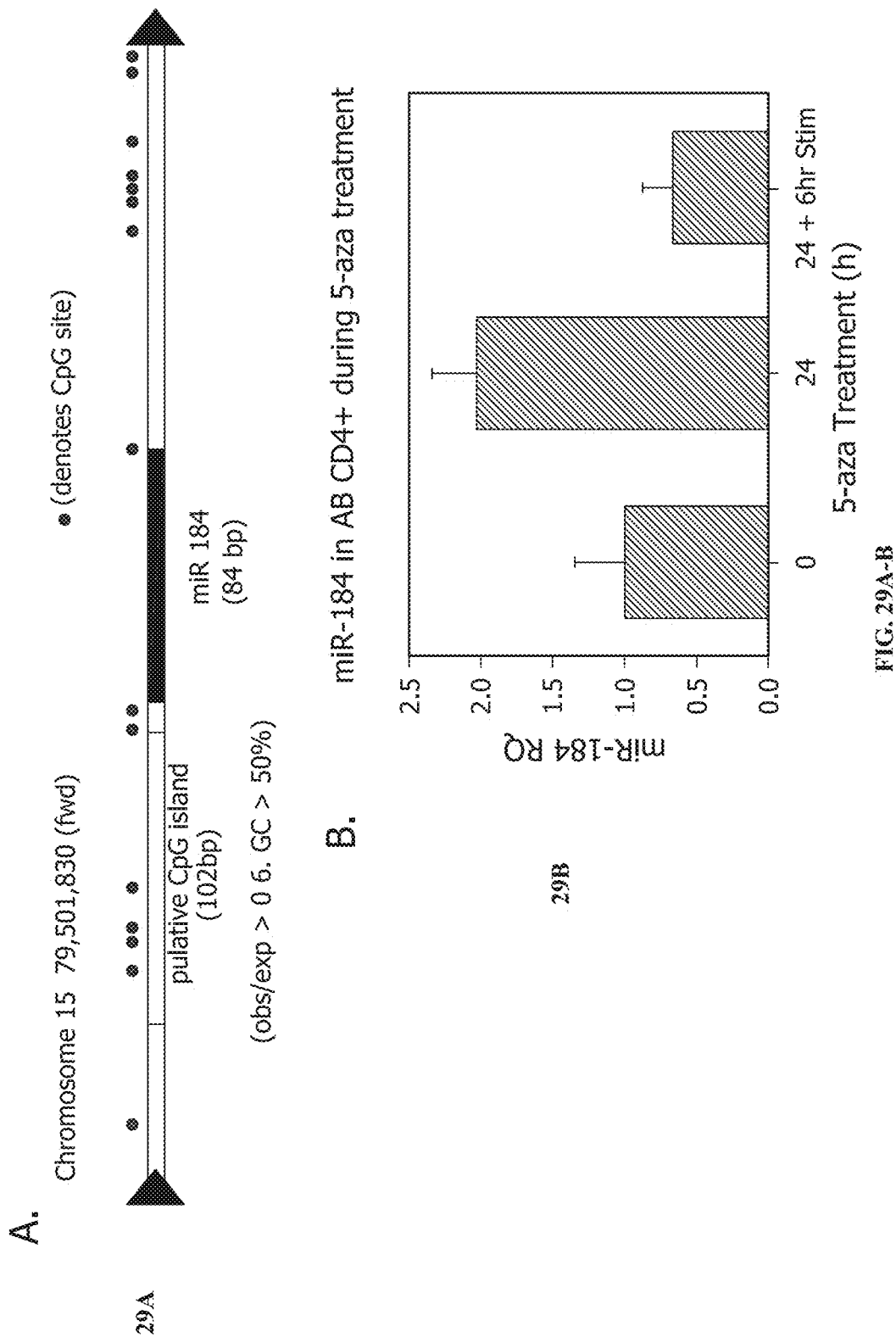
FIG. 29A-B

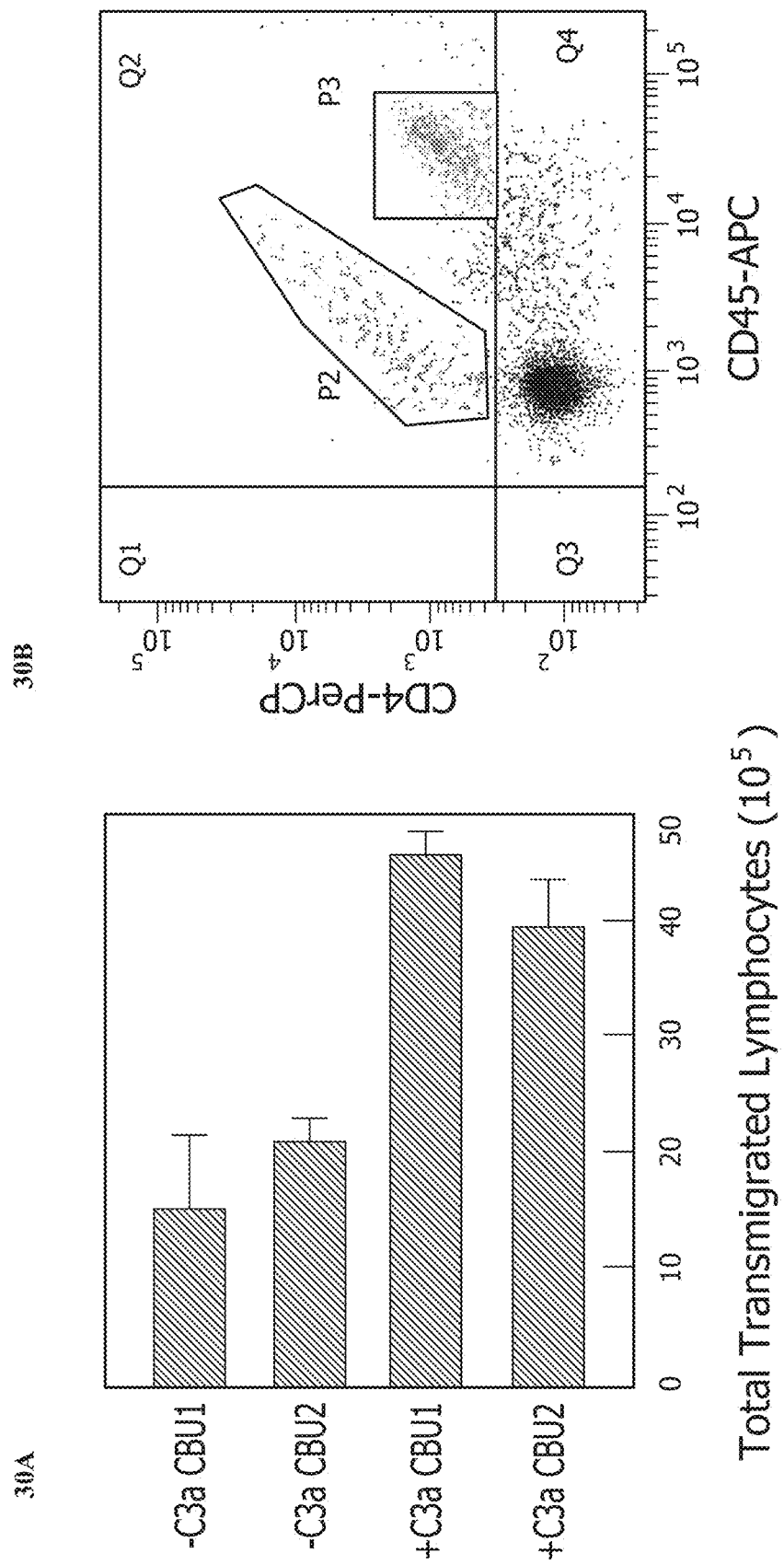
FIG. 30A-B

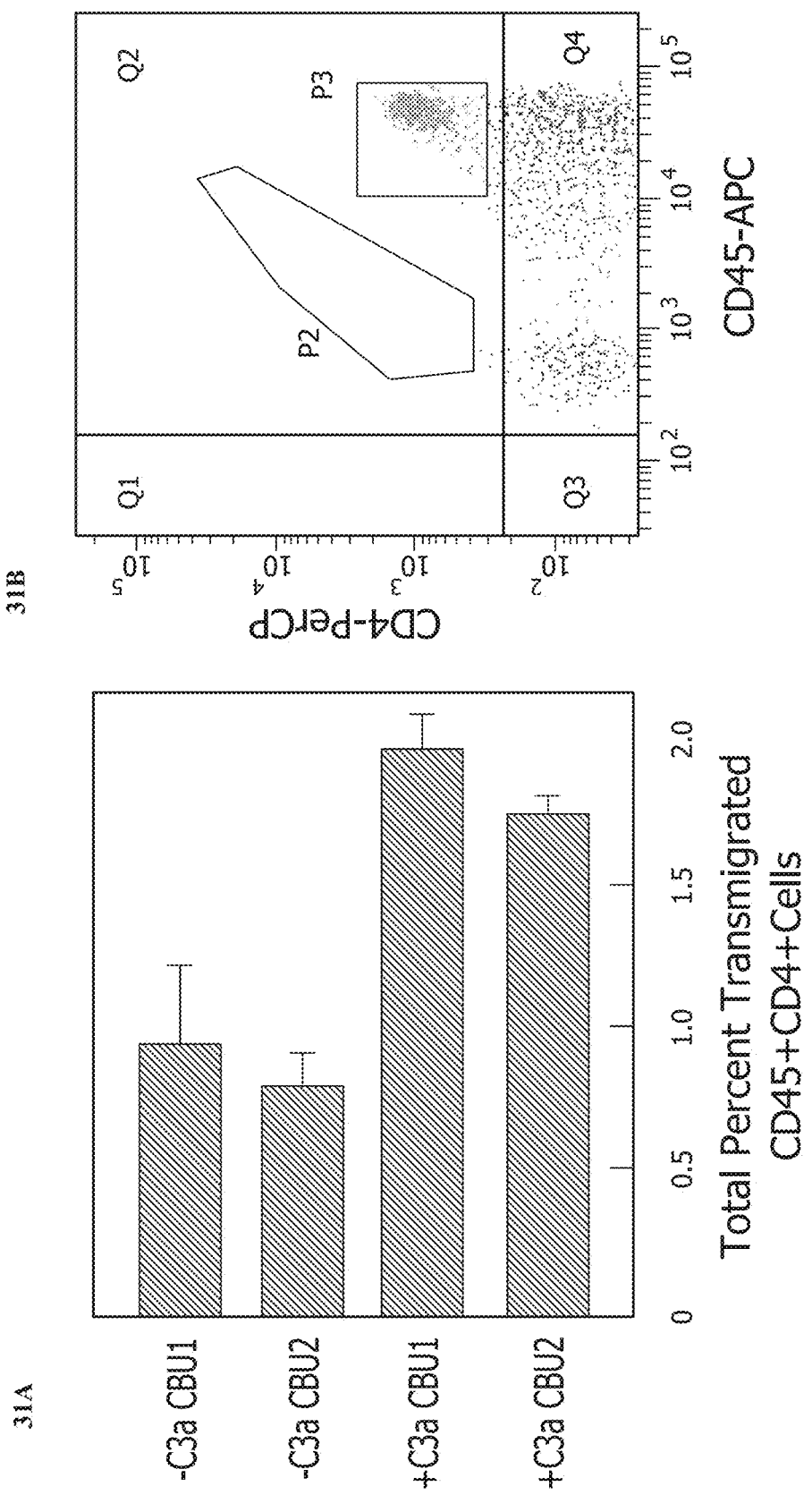
FIG. 31A-B

Summary of phase I clinical trial patient BM cell counts and sterility results

| Patient Number | Pre-MNC count (10⁶) | Post-CD133+ CD45+ (%) | Post-CD133+ counts | Post-selection viability | Gram Staining | Endotoxin | Mycoplasma |
|---|---|---|---|---|---|---|---|
| 1 | 5,940 | 88.0 | 20.3 | 98.0 | None | Neg | Neg |
| 2 | 6,280 | 77.0 | 48.5 | 97.0 | None | Neg | Neg |
| 3 | 8,120 | 77.3 | 11.6 | 87.2 | None | Neg | Neg |
| 4 | 4,550 | 80.0 | 8.00 | 75.0 | None | Neg | Neg |
| 5 | 4,660 | 91.0 | 11.8 | 80.0 | None | Neg | Neg |
| 6 | 9,540 | 94.5 | 30.2 | 93.9 | None | Neg | Neg |
| 7 | 8,040 | 78.0 | 19.5 | 84.0 | None | Neg | Neg |
| 8 | 6,980 | 88.3 | 13.2 | 70.0 | None | Neg | Neg |
| 9 | 4,720 | 80.8 | 17.8 | 72.0 | None | Neg | Neg |
| Summary | 6,537 (± 1,774) | 83.4 (± 6.9) | 20.1 (± 13.4) | 82.4 (± 10) | | | |

TNC (total nucleated cells, x 10⁶). % AC133+ (% AC133+ of gated CD45+ MNC).

FIG. 33

There was no effect of the infusion of C3a primed UCB on downstream pathways
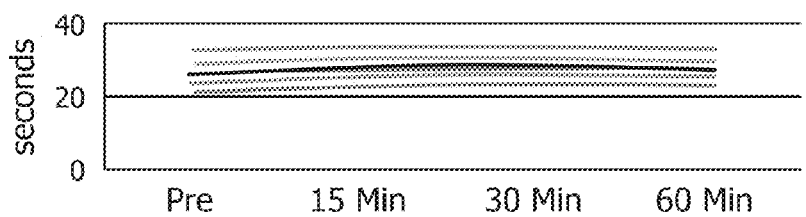
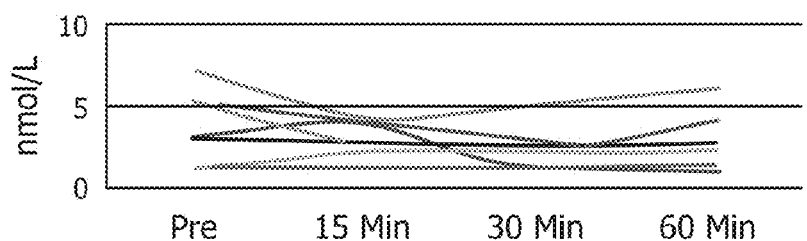
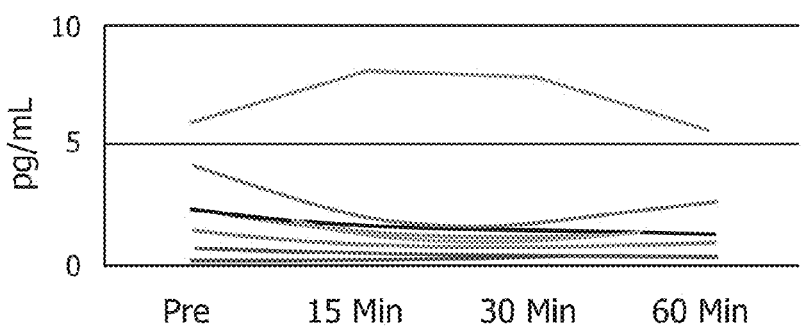
FIG. 42B Significantly higher CD3+ cell doses may have introduced bias against predominance of C3a primed UCB units

| Patient Number | Predominant at Day +21 | TNC (x10e8/kg) C3a | TNC (x10e8/kg) Other | CD3+ (x10e7/kg) C3a | CD3+ (x10e7/kg) Other | HLA-match (X out of 8) C3a | HLA-match (X out of 8) Other | MNC Visbility C3a | MNC Visbility Other |
|---|---|---|---|---|---|---|---|---|---|
| 1 | C3a | 0.13 | 0.28 | 0.6 | 0.8 | 4 | 4 | 88 | 76 |
| 2 | C3a | 0.18 | 0.26 | 0.6 | 0.8 | 8 | 8 | 83 | 84 |
| 3 | C3a | 0.11 | 0.28 | 0.4 | 0.7 | 6 | 6 | 78 | 68 |
| 4 | C3a | 0.18 | 0.18 | 0.5 | 0.5 | 8 | 6 | 84 | 72 |
| 5 | C3a | 0.18 | 0.28 | 0.7 | 0.8 | 6 | 6 | 85 | 48 |
| 6 | other | 0.13 | 0.31 | 0.7 | 1.7 | 4 | 4 | 78 | 80 |
| 7 | other | 0.12 | 0.49 | 0.4 | 2.8 | 8 | 6 | 81 | 48 |
| 8 | other | 0.35 | 013 | 1.0 | 0.4 | 4 | 6 | 71 | 72 |
| 9 | C3a | 0.03 | 0.21 | 0.3 | 0.8 | 6 | 4 | 74 | 81 |
| 10 | Not evaluable | NA | NA | NA | NA | NA | NA | NA | NA |
| | Median | 0.13 | 0.26 | 0.5 | 0.8 | 5 | 5 | 69 | 61 |
| | P-value | <.01 | | <.01 | | NS | | NS | |

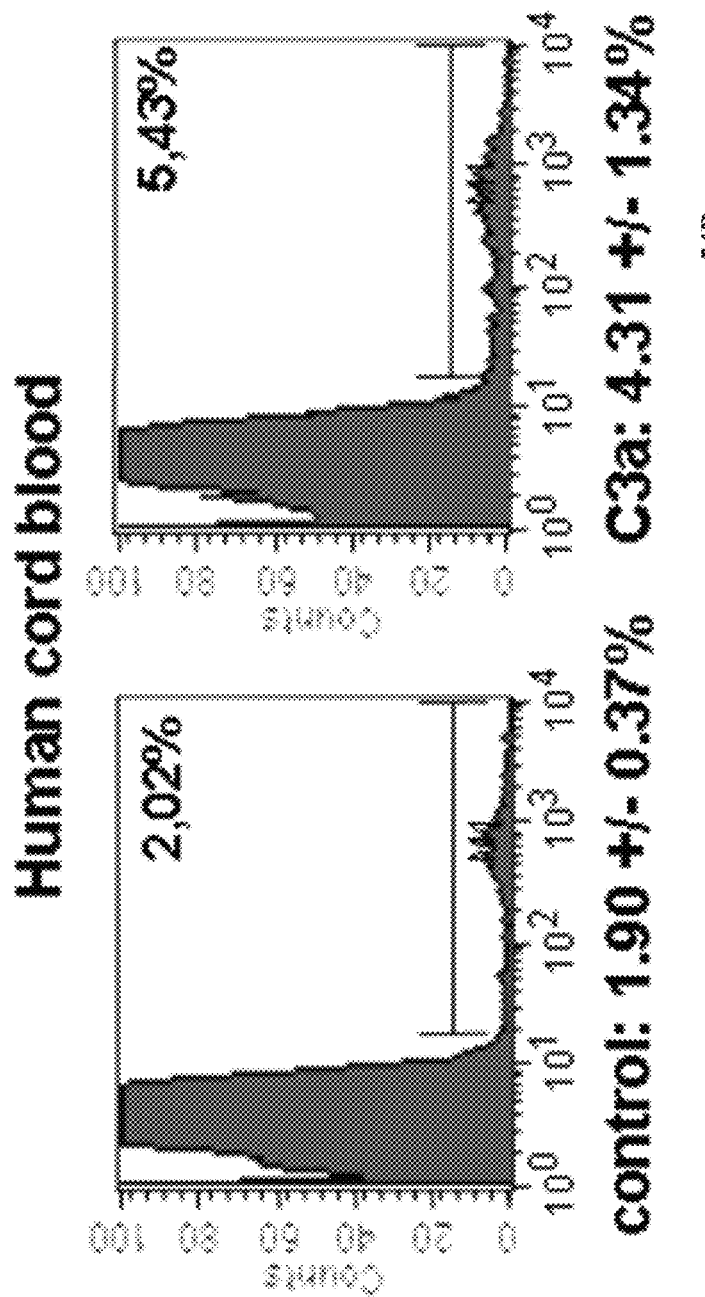
FIG. 54A-B

COMPOSITIONS AND METHODS FOR CXCR4 SIGNALING AND UMBILICAL CORD BLOOD STEM CELL ENGRAFTMENT

CROSS REFERENCE TO RELATED APPLICATIONS

This application is entitled to priority pursuant to 35 U.S.C. §119(e) to U.S. provisional patent application No. 61/605,035, filed on Feb. 29, 2012. The entire disclosure of the afore-mentioned patent application is incorporated herein by reference.

STATEMENT REGARDING FEDERALLY SPONSORED RESEARCH OR DEVELOPMENT

This invention was made with government support under Grant No. RC1 HL 099047-01, awarded by The National Institutes of Health. The government has certain rights in the invention.

BACKGROUND

Umbilical Cord Blood (UCB)-derived stem cells, which are non-embryonic, are non-controversial (with approval by the Vatican and all religious groups), and offer the potential for numerous "off the shelf" cell therapeutic products that are easier to obtain and faster to distribute than individual adult directly donated bone marrow and blood cells. An emerging technology, UCB stem cell grafts for treatment of hematology patients have a U.S. market potential of $425 million/year, with additional market potential combining Europe, Asia, and S. America of $978 million/year, rendering a world-wide market potential of $1.4 billion annually and growing. Cord blood not only has these immediate therapeutic applications in hematology patients, but many more in the pipeline in regenerative medicine applications. So far, doctors have found the most promise in cord blood for conditions such as blood cancers, leukemia, and sickle-cell anemia. In addition, UCB, like embryonic stem cells, contains multi-potential stem cells that give rise to all somatic cells. Many investigators believe that UCB will eventually prove useful in regenerative medicine, helping patients with cardiovascular disease, spinal bifida, traumatic brain injuries, and neurodegenerative disorders. However, successful infusion and engraftment in humans of $CD34^+$ hematopoietic stem cells (HSC) from a UCB graft is challenged by the cellular content that is generally a log order less in total cell dose than that of bone marrow or mobilized peripheral cells from adult donors.

Hematopoietic stem cells are multipotent stem cells that give rise to all the blood cell types including human CD34+ stem cell. The CD34 molecule is a cluster of differentiation molecules present on certain cells within the human body. It is a cell surface glycoprotein and functions as a cell-cell adhesion factor. It may also mediate the attachment of stem cells to bone marrow extracellular matrix or directly to stromal cells. CD34 is also the name for the human gene that encodes the protein.

Cells expressing CD34 (CD34+ cell) are normally found in the umbilical cord and bone marrow as hematopoietic cells and tend to migrate from the blood stream to the bone marrow along a gradient of stromal derived factor-1 (SDF-1) where SDF-1 levels are high in the bone marrow and low in the peripheral blood. SDF-1 is a cytokine belonging to the chemokine family CXCL12. When a bone marrow transplant patient receives allogeneic UCB mononuclear cells via intravenous infusion, successful engraftment entails UCB stem cells taking up residence in the patient's bone marrow. A peripheral blood mononuclear cell is any blood cell having a round nucleus. Activation of the complement system in the transplant patient as part of the stress response elicited by chemoradiotherapy conditioning activates proteases in the marrow that reduce SDF-1 concentration. Low SDF-1 levels in the bone marrow tend to lessen homing and engraftment of allogeneic UCB CD34 stem cells. Because the numbers of CD34+ hematopoietic stem cells (HSC) in UCB is low, methods to enhance engraftment of this population of cells are needed.

Since the first unrelated donor UCB transplant in 1993 it has been demonstrated that cryopreserved UCB from HLA 0-2 antigen mismatched unrelated donors contain sufficient numbers of transplantable hematopoietic stem and progenitor cells or reliable engraftment in most recipients weighing <40 kilograms (kg) and that it is associated with a low incidence of acute graft-versus-host disease (GVHD) despite substantial disparities in HLA between the donor and recipient. Yet, poor engraftment and slow rate of neutrophil and platelet recovery remain important challenges that increase risk of transplant-related mortality (TRM).

The 'double' UCB transplant (UCBT) platform was initiated as a potential strategy for testing graft manipulations and h its safety and efficacy has been established. In addition, we and others have shown that its utility as a model for testing of novel strategies in which one unit manipulated and the second is left unmanipulated to maximize safety. This strategy offers the additional advantage of being able to 'track' the manipulated unit's lympho-hematopoietic progeny over time based on the inherent genetic differences between the two UCB units and the recipient. Importantly, the double UCBT approach has transformed the field by extending the eligibility of transplantation to nearly all patients regardless of size and racial or ethnic background.

Engraftment is the single most important barrier to successful use of UCB. In comparison to mobilized peripheral blood and marrow from adult unrelated donors, time to neutrophil recovery and ultimate engraftment after UCBT is markedly delayed. Engraftment of HSC and hematopoietic progenitors after transplantation is the result of a complex series of events within the marrow microenvironment, involving adhesion and migration, integrity of the 'stem cell niche and presence of chemotactic cytokines and growth factors that either preserve 'sternness', prevent or promote apoptosis or incite lineage-specific expansion and differentiation. While it is clear that UCB HSC have the capacity to engraft and insure life-long hematopoietic reconstitution (>20 years in the longest surviving UCBT recipient), interest in ex vivo expansion of HSC and progenitors has largely been driven by the clear association between cell dose and time to hematopoietic recovery and incidence of engraftment. Delayed engraftment may also be the result of the higher proportion of UCB CD34 in $G_0$ and greater likelihood of HLA mismatch.

Limitations of current management of vascular disease include re-occlusion and diffuse small vessel disease. Prior evidence links the level of circulating marrow-derived HSC, characterized by expression of CD133 and CD34, with the occurrence of ischemic vascular events. HSC which express CD34 and CD133 surface markers have been shown in models of acute and chronic ischemia to augment blood flow and prevent myocardial necrosis There is emerging evidence of age-related diminution in the number and function of marrow-derived CD34/133+ HSC in response to ischemia.

There is a long felt need in the art for compositions and methods to increase engraftment of UCB stem and T-cells, as well as other sources of stem and hemopoietic stem and progenitor cells. The present invention satisfies these needs.

SUMMARY OF THE INVENTION

The present application discloses the efficacy of pretreating populations of cells comprising hemopoietic cells such as umbilical cord blood to enhance engraftment. The present application further discloses agents useful for such purposes.

The use of umbilical cord blood has revolutionized bone marrow transplantation, rising from less than 1% of allografts in 2001 to 28% of all unrelated marrow and stem cell transplant procedures performed in the US annually (see CIBMTR and the website: 'Sources of Cells for Transplant'). UCB has clinical and logistic advantages over that of individual patient adult-derived stem cells. Clinical advantages include: UCB collection at no risk to the donor; greater accessibility for long-term storage; immediate availability in a bank; wider availability of diverse HLA genotypes with approximately 450,000 units banked worldwide and listed on web-based inventories; lower immune reactivity; and lower inherent pathogen transmission. UCB inventory is representative of the wide HLA genotype of a diverse American population, and has been shown to elicit reduced incidence and severity of graft vs. host disease (GVHD) reaction compared with standard adult-derived HSC. Thus, UCB allogeneic cellular therapy may be ideally suited for use in patients with hematologic disorders requiring allogeneic transplantation.

Recent data suggests that responsiveness of UCB HSC to an SDF-1 gradient may be positively modulated/primed/enhanced by several factors, e.g., C3 complement cleavage fragments (C3a and $_{desArg}$C3a), fibronectin, fibrinogen, and hyaluronic acid. The responsiveness of UCB HSC to an SDF-1 gradient is an important factor that determines allogeneic hematopoietic engraftment. Further, our data show that UCB HSC responsiveness to an SDF-1 gradient varies somewhat with each UCB unit. More importantly, since responsiveness of UCB HSC to an SDF-1 gradient may be enhanced by employing this 'priming' strategy, this phenomenon is of clinical importance. The problem of engraftment is particularly challenging with UCB because the stem cell population is lower than in adult derived mononuclear cell grafts.

Successful infusion and engraftment in humans of cells such as CD34+ HSC from a UCB graft is challenged by the cellular content that is generally a log order less in total cell dose than that of bone marrow or mobilized peripheral cells from adult donors. Thus methods are needed to increase engraftment of UCB stem and T-cells.

In one embodiment, the present invention encompasses administering a population of cells, such as umbilical cord blood cells, bone marrow, or peripheral blood, wherein the cells are pretreated with an engraftment enhancing agent before administration of the cells to a subject.

In one embodiment, the compositions and methods of the present invention satisfy the above-described need by pharmacologically or biologically manipulating UCB graft mononuclear cells to augment HSC and progenitor cell homing to the marrow and thereby to enhance allogeneic donor engraftment.

The present invention provides compositions and methods to enhance engraftment of UCB stem cells by, for example, enhancing UCB CD34+ stem cell and CD4 T-cell responsiveness to SDF-1 signaling. T helper cell (TH cells) assist other white blood cells in immunologic processes, including maturation of B cells into plasma cells and B memory cells, and activation of cytotoxic T cells and macrophages, among other functions. These cells are also known as CD4+ T cells because they express the CD4 protein on their surface. The invention encompasses treating populations of cells, such as UCB, ex vivo with activated complement cleavage fragments (C3a or $_{desArg}$C3a). This is done to activate the SDF-1 receptor CXCR-4 expressed on UCB CD34+ stem and CD4 T-cells, which sensitizes the UCB cells expressing CXCR-4 to SDF-1 signaling ("functional agonist"). More specifically, the cells can be sensitized, for example, using $_{desArg}$C3a fragment as a CXCR-4 receptor agonist.

In one embodiment, allogeneic cord blood units transfused into patients after administration of reduced intensity or myeloablative chemo-radiotherapy are first treated ex vivo with $_{desArg}$C3a fragment to enhance UCB CD34+ HSC and CD4 T-cell responsiveness to SDF-1 prior to infusion into the patient, rather than systemic administration of a $_{desArg}$C3a fragment. Thus, the amount of $_{desArg}$C3a fragment transfused is minimal. In one embodiment, C3a is used.

In one embodiment, the present invention encompasses the use of at least one CXCR4 receptor activating agent, including, but not limited to, C3 complement cleavage fragments (C3a and $_{desArg}$C3a), fibronectin (FN), fibrinogen (FG), or hyaluronic acid (HA) to sensitize CXCR4 receptors on UCB stem and CD4 T-cells to render them more capable to sense the SDF-1 gradient after infusion. UCB mononuclear cells are treated ex vivo and, after treatment, the UCB cells infused into the patient. Compounds such as C3a and $_{desArg}$C3a are known to be stable in whole blood ex vivo but are quickly adsorbed, and thus inactivated, in vivo. These agents are useful engraftment enhancing agents.

In another embodiment, the present invention encompasses the use of UCB mononuclear cells transfused into patients who have undergone reduced intensity or myeloablative therapy in anticipation of bone marrow reconstitution via UCB cell allograft would be pretreated ex vivo with C3a or $_{desArg}$C3a. The net effect is higher responsiveness of the treated UCB cells to a lower concentration of SDF-1 in the bone marrow, thus enhancing homing and engraftment of the donor allogeneic UCB stem cells to and within the patient's marrow.

The present invention provides compositions and methods useful for enhancing engraftment of cells for preventing and treating diseases, disorders, and conditions in a subject in need thereof or when used in conjunction with other treatments for preventing and treating diseases, disorders, and conditions. In one aspect, umbilical cord blood is used. In another aspect, bone marrow-derived cells are used. Compositions comprising populations of cells, such as umbilical cord blood cells, from various sources are disclosed herein to be useful to practice the methods of the invention. The present application further discloses that to improve efficiency the cell populations can be enriched for specific cell phenotypes. Furthermore, priming or pretreating the cells with various agents prior to administration can improve treatment. The agents include, but are not limited to, proteins and peptides and biologically active fragments and homologs thereof, nucleic acids, drugs, and combinations thereof.

The compositions and methods of the invention are useful for treating, for example, subjects with blood cancers, leukemia, myelodysplastic syndromes, and sickle-cell anemia. In another aspect, the compositions and methods of the invention are useful for treating subjects with cardiovascular disease, spinal bifida, traumatic brain injuries, and neurodegenerative disorders. In one aspect, the compositions and methods of the invention are useful for bone marrow transplant patients. In one aspect, the compositions and methods of the invention are useful for subjects with high-risk hematologic malignancy. In one aspect, the subject has been the recipient of a myeloablative or non-myeloablative regimen. The diseases, disorders, and conditions listed herein are not meant to be limiting and are instead meant to be examples of the usefulness of the compositions and methods of the present invention.

In one embodiment, a population of cells is contacted with an effective amount of an agent such as a protein or drug prior to administration of the cells to a subject, whereby the agent enhances engraftment. The amount of time after contacting the cells with an agent before the cells are administered to the subject can vary depending on the agent used, the type of cell population being used, the health of the subject, etc. In one aspect, the cells are contacted with a $CXCR_4$ receptor-activating agent prior to being administered to a subject. In one aspect, the activating agent is one or both of the C3 complement cleavage fragments C3a and des-ArgC3a, or biologically active fragments or homologs thereof. In one aspect, the agent is fibronectin, fibrinogen, or hyaluronic acid. In one aspect, more than one protein or agent is used, including, but not limited to, C3a, des-ArgC3a, fibronectin, fibrinogen, hyaluronic acid, soluble VCAM-1, soluble ICAM-1, cathelicidin, β2-defensin, and uPAR.

In one aspect, the cells administered to a subject are allogeneic. In one aspect, the cells are autologous.

In one embodiment, the cell population to be administered to a subject is enriched for CD133+ cells. In one embodiment, the cell population to be administered to a subject is enriched for CD34+ cells. In one embodiment, the cell population to be administered to a subject is enriched for CD133+ cells and CD34+ cells. Enrichment can be achieved by stimulating the cell of interest or by a method used to physically increase the number of cells of interest and/or decrease other cell types. In one aspect, the number of stem cells or progenitor cells is increased by expansion in cell culture.

In one embodiment, the present invention encompasses compositions and method useful for treating and preventing cardiovascular diseases, disorders, and conditions, including, but not limited to, re-occlusion and diffuse small vessel disease and ischemia. In one embodiment, the compositions and methods are useful for treating and preventing the age-related diminution in the function and number of marrow-derived hemopoietic stem cells in response to ischemia. In one aspect, the hemopoietic stem cells are CD34/133+ cells. In one aspect, the invention provides for administering a composition comprising population of cells, wherein said population comprises CD34/133+ cells. In one aspect, population of cells is selected from the group consisting of umbilical cord cells and bone marrow cells.

In one aspect, the use of allogeneic cells can be optimized by lowering the infused dose of cells.

Based on the disclosure of the present application and as described above, in one embodiment the present invention provides a method for enhancing hemopoietic cell engraftment in a subject comprising contacting a population of cells comprising hemopoietic cells with an effective amount of at least one agent that enhances engraftment of the hemopoietic cells, and then administering the population of cells to the subject. In one aspect, the population of cells is selected from the group consisting of umbilical cord blood cells, peripheral blood cells, and bone marrow cells. In one aspect, the engraftment enhancing agent is selected from the group consisting of complement protein fragment 3a (C3a), complement protein fragment desArg3a (desArgC3a), fibronectin, fibrinogen, hyaluronic acid, soluble VCAM-1, soluble ICAM-1, uPAR, hβ2-defensin, and cathelicidin, or active fragments and homologs thereof. One of ordinary skill in the art will appreciate that these agents can be used in combination as well.

A useful population of cells of the invention comprises hemopoietic cells selected from the group consisting of hemopoietic stem cells, hemopoietic progenitor cells, and both hemopoietic stem and progenitor cells.

In one embodiment, the engraftment comprises an allogeneic donor engraftment. In another, it is autologous.

In one embodiment, at least two different populations of cells are administered to a subject. For example, the two populations can be different units of cord blood, or are from peripheral blood or from bone marrow.

In one aspect, when two populations are used, they are at least partially HLA matched.

In one embodiment, when more than one population of cells is to be administered to a subject, not all populations of cells are contacted with at least one engraftment enhancing agent prior to administration of each populations of cells to a subject.

In one embodiment, two populations of cells are administered. In one aspect, both populations are contacted with an engraftment enhancing agent prior to administration, and in another aspect, only one population of cells is contacted with the agent.

The number of cells administered can be varied depending on, for example, the source of the cells, the age of the subject, and the health of the subject. In one embodiment, at least $1.5 \times 10^7$ nucleated cells/kg are administered to a subject. In another embodiment, when at least two populations of cells are administered, each population has at least $1.5 \times 10^7$ nucleated cells/kg. In one aspect, when two populations of umbilical cord blood cord cells are administered, each of the two administered populations comprises at least $1.5 \times 10^7$ nucleated cells/kg.

When umbilical cord blood is used as a source of a population of cells for engraftment, more than one unit can be used. In one aspect, when two or more units are used, only one unit is pretreated by contacting the cells with at least one agent to enhance engraftment of hemopoietic cells. In one aspect, two units are contacted with at least one engraftment enhancing agent. In another aspect, all units are pretreated. In one embodiment, when two populations of umbilical cord blood cells are administered, a first population is administered without being contacted with at least one agent that enhances engraftment and then a second population of umbilical cord blood cells is administered that has been contacted with at least one engraftment enhancing agent.

In one embodiment, an engraftment enhancing agent of the invention enhances responsiveness of the infused hemopoietic cells to an SDF-1 gradient. In one aspect, the agent enhances homing of the hemopoietic cells to bone marrow. In one aspect, the agent enhances chemotaxis.

The amount of time that a population of cells is exposed to an engraftment enhancing agent can vary, depending on the particular circumstances for the engraftment. For example, exposure can be from several minutes to several hours. In one aspect, cells are exposed to an engraftment enhancing agent for about 30 minutes. In one aspect, the cells were frozen and then thawed before being contacted with the agent.

In one embodiment, a patient is subjected to a conditioning regimen prior to administration of a population of cells that has been contacted with at least one engraftment enhancing agent. In one embodiment, more than one population of cells can be administered, and as described herein one or more of the populations can be contacted with an engraftment enhancing agent prior to administration to the subject.

One of ordinary skill in the art will appreciate that the amount of engraftment enhancing agent used can vary, depending on such factors as the source of the cells used, the age of the subject, the health of the subject, and the agent used. In one aspect, cells are contacted with an engraftment enhancing agent at a concentration ranging from about 0.1 μg/ml to about 10 mg/ml. In one aspect, the range is from about 1.0 μg/ml to about 1.0 mg/ml. In one aspect, about 1.0 μg/ml of engraftment enhancing agent is used.

In one embodiment, a population of cells comprising hemopoietic cells is contacted with an effective amount of at least two agents prior to administration to a subject. In one embodiment, two or more populations of cells are each contacted with at least one engraftment enhancing agent prior to administration of the cells to the subject. In one embodiment, when two or more populations of cells are used, at least one of the populations of cells is contacted with at least two engraftment enhancing agents. In one embodiment, when two or more populations of cells are administered to a subject, at least one of the populations of cells is not contacted with an engraftment enhancing agent.

In one embodiment, the engraftment enhancing agent increases activity of the SDF-1 receptor CXCR4 in a cell expressing CXCR4. In one aspect, the agent enhances the responsiveness of cells to SDF-1.

In one embodiment, the umbilical cord blood cells administered comprise CD34+ hemopoietic stem cells and CD3 T-cells.

In one embodiment, the population of cells administered comprises CD133+ cells.

In one embodiment, the population of cells administered comprises CD133+/CD34+ cells.

In one embodiment, the C3a administered comprises the sequence SEQ ID NO:1, or homologs and fragments thereof. In one embodiment, the desArgC3a administered comprises the sequence SEQ ID NO:2. In one aspect, each are used.

In one embodiment, the method of the invention enhances the rate of hemopoietic recovery in a subject.

In one embodiment, a subject is being treated for a disease, condition, or disorder including, but not limited to, cancer, blood cancers, leukemia, myelodysplastic syndromes, sickle-cell anemia, high risk hematologic malignancy, cardiovascular disease, spinal bifida, traumatic brain injuries, and neurodegenerative disorders.

In one embodiment, the subject to whom the population of cells is being administered has been the recipient of a myeloablative or non-myeloablative regimen.

In one embodiment, cells are administered to a subject, at least one therapeutic agent is also administered.

In one embodiment, prior to administration a population of cells is enriched for hemopoietic stem cells, hemopoietic progenitor cells, or both hemopoietic stem and progenitor cells. In one aspect, the population of cells is enriched for CD133+ cells prior to administration to the subject. In one aspect, the population of cells is enriched for CD34+ cells prior to administration to the subject. In one embodiment, an enriched populations of cells is contacted with an engraftment enhancing agent prior to administration. In another embodiment, an enriched population of cells is not contacted with an engraftment enhancing agent prior to administration to a subject. One of ordinary skill in the art will appreciate that enriched populations of cells can be used as described herein for other populations of cells, including the descriptions for using one or more populations, contacting one or more populations with an engraftment enhancing agent at different concentrations, etc., when the populations have not been subjected to an enrichment procedure.

The present invention further provides kits. In one embodiment, the invention provides kits for enhancing hemopoietic cell engraftment. In one aspect, the kit comprises at least one population of cells comprising hemopoietic cells. In one aspect, the cells are umbilical cord blood cells, peripheral blood cells, or bone marrow cells. The kit further provides at least one agent effective for stimulating engraftment. The kit optionally provides a pharmaceutically acceptable carrier, an applicator, and an instructional material for the use thereof.

In one embodiment, the present invention further provides a method to enhance a response to ischemia in a subject in need thereof. In one aspect, the method comprises administering to the subject an effective amount of a population of cells comprising CD133+ cells. In one aspect, the ischemia is vascular ischemia. In one aspect, the vascular ischemia is coronary artery ischemia. In one aspect, the CD133+ cells are umbilical cord blood CD133+ cells or they are CD133+ autologous marrow-derived cells. In one aspect, the subject being treated has age related diminution of CD133+ angiogenic function. In another aspect, the subject has disease related diminution of CD133+ angiogenic function. The present further provides for processing the population of cells to increase the proportion of administered CD133+ cells. The invention further encompasses processing a population of cells to delete or decrease the number of immune and antigen presenting cells.

In one embodiment, the invention encompasses administering an effective amount of CD133+ autologous marrow-derived cells to a subject with occluded coronary arteries to enhance revascularization intervention. In one aspect, the autologous marrow-derived cells are hemopoietic stem cells.

In one aspect, the present invention provides compositions and methods useful for using dose escalating CD133+ autologous marrow-derived HSC for patients with occluded coronary arteries to enhance revascularization intervention. Methods for administering CD133+ HSC include via coronary infusion in the vessel providing collateral blood flow. In one aspect, the CD133+ cells are selected from bone marrow.

The present application discloses age and disease-related diminution of CD133+ angiogenic function. Therefore, the present invention comprises methods for determining if a subject has such age related diminution and coupling such determination with a treatment regimen for a subject. Changes in response to various chemokines or growth factors or to secretion of various factors can be used to establish a treatment regimen for the subject.

In one aspect, autologous peripheral blood or bone marrow can be used and in another aspect, allogeneic UCB can be used. In one aspect, at least two of these sources of populations of cells can be used.

Without wishing to be bound by any particular theory, it is hypothesized herein that there is a relationship between CD133+ immunogenicity and vasculogenesis functionality.

In one embodiment, based on the disclosure herein that there is diminished angiogenic function of CD133+ from advanced age patients with cardiovascular disease, administration of HSC is useful for treatment of vascular ischemia. In one aspect, allogeneic HSC are used. The stem cell therapeutics of the present invention can be coupled with other treatments and with the administration of other agents. In one aspect, UCB-derived HSC are used. In one aspect, selected CD133+ UCB-derived HSC are used. In one aspect, methods of the invention are useful to delete immune and antigen presenting cells from a MNC preparation that may exert adverse immunologic effects in a patient with an intact immune system.

One of skill in the art will appreciate that in some instances populations of cells comprising CD34+/CD133+ cells can be used or enriched populations can be used.

The present invention provides compositions and methods useful for developing treatment strategies comprising stem cell therapy, as well as the use optional use of additional agents, based on determining what age related changes have occurred in a subject and what diseases or conditions are present in the subject.

Useful sequences of the invention include, for example:

```
                                          SEQ ID NO: 1-
Human Complement C3a anaphylatoxin
(77 residues)-
SVQLTEKRMDKVGKYPKELRKCCEDGMRENPMRFSCQRRTRFISLGEACK

KVFLDCCNYITELRRQHARASHLGLAR

SEQ ID NO: 2-
Human C3a des-arg (76 residues)-
SVQLTEKRMDKVGKYPKELRKCCEDGMRENPMRFSCQRRTRFISLGEACK

KVFLDCCNYITELRRQHARASHLGLA

SEQ ID NO: 3-
Human miR-184-
UGGACGGAGAACUGAUAAGGGU

SEQ ID NO: 4-
complementary miR-184-
UGGGAAUAGUCAAGAGGCAGGU

SEQ ID NO: 5-
portion of NFAT1 as described in Example 3,
FIG. 7-
AUCCUGGUUGAUCUUAAUGGUGUCCGUCCAAAUAGUAAAUAG
```

The underlined portions of SEQ ID NOs:4 and 5 indicate the complementary

Various aspects and embodiments of the invention are described in further detail below.

BRIEF DESCRIPTION OF THE DRAWINGS

Example 1

FIG. 6A-B—Sca-1+ Cells Primed with C3a Engraft Faster in Lethally Irradiated Mice. 6A—left panel; 6B—right panel.

Example 2

Figure 9:
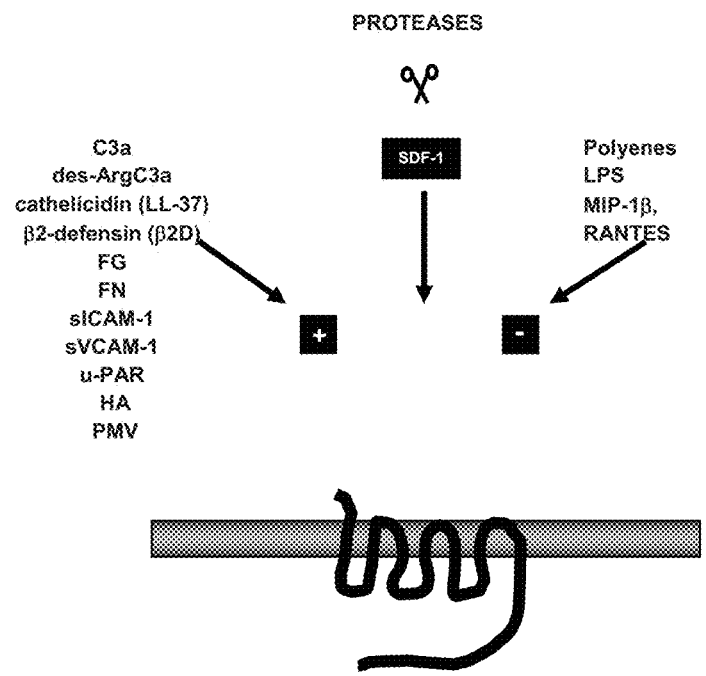

FIG. 9—Schematic of SDF-1-CXCR4 axis modulation/priming by various factors. The SDF-1-CXCR4 axis is modulated by various external factors. In one regard, these target SDF-1 or the N-terminus of CXCR4, which are both cleaved by leukocyte-derived proteases or MMPs. Conversely, they target the SDF-1-CXCR4 axis, which can be primed positively (e.g., by C3a, $_{des-Arg}$C3a, cathelicidin, β2-defensin, uPAR, FG, FN, HA, sICAM1, and cVCAM1) or negatively (e.g., by polyene antibiotics). Several of these molecules are present in leucopheresis product as well as can also be found in tissues affected by inflammation and modulate the responsiveness of CXCR4+ cells to an SDF-1 gradient.

Figure 10:
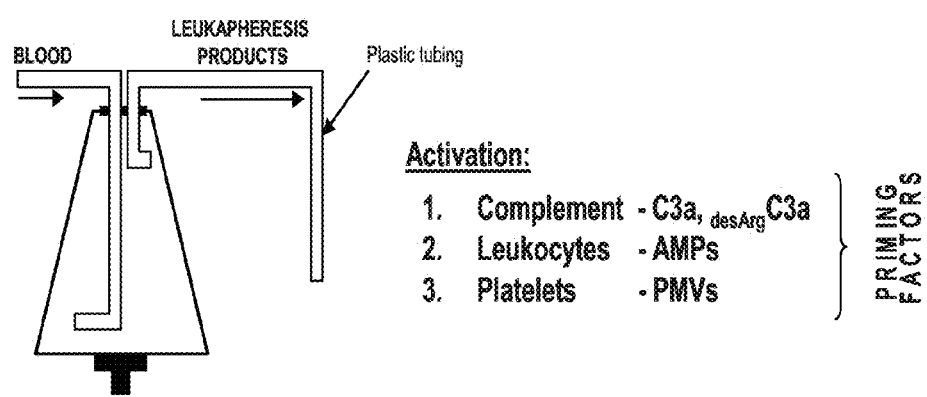

FIG. 10—Leucopheresis activates several components of mPB. Due to contact with plastic tubing and share forces leucopheresis product becomes enriched in i) complement cleavage fragments (e.g., C3a and $_{desArg}$C3a), ii) leucocyte-derived antimicrobial cationic peptides cathelicidin and β2-defensin and iii) released from activated platelet microvesicles (PMV). Our published data demonstrate that all these compounds enhance engraftment of HSPCs by enhancing homing responsiveness of HSPCs to SDF-1 gradient (C3a, defensin, β2-cathelicidin) or by transferring homing relevant receptors to surface of HSPCs (PMV).

FIG. 11A-B—Effect of SLP and its components on chemotaxis of CD34+ cells. Panel A: Chemotaxis of BM CD34+ cells towards medium alone (control), SDF-1 low (10 ng/mL) alone, SLP (combined SLP from three patients), SDF-1 low+SLP, and SDF-1 high (300 ng/mL). Data are pooled from quadruplicate samples from three independent experiments. *p<0.00001. Panel B: Chemotaxis of UCB CD34+ cells to medium alone (control), SDF-1 low (10 ng/mL) alone and SDF-1 low (10 ng/mL)+uPAR (1 μg/mL) or +ICAM (1 μg/mL) or +VCAM (1 μg/mL) or +FN (2 μg/mL), or +FG (4 μg/mL) or +C3a (1 μg/mL). Data are pooled from quadruplicate samples from three independent experiments. * p<0.00001.

Figure 12:
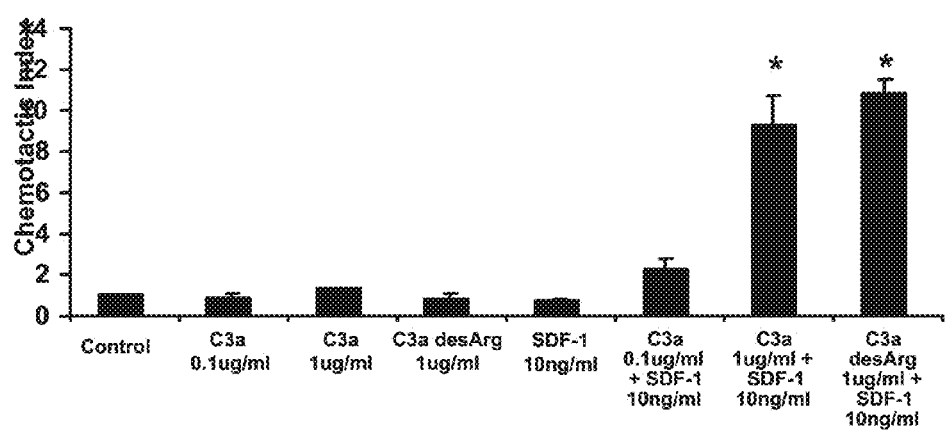

FIG. 12—Both C3a and C3$_{ades-Arg}$ potentiate chemotaxis of human BM-derived CD34+ cells to low/threshold dose of SDF-1. Chemotaxis of CD34+ cells to medium alone (control), C3a (1 μg/ml), C3a$_{desArg}$ (1 μg/ml), SDF-1 low (10 ng/mL) alone, and SDF-1 low (10 ng/mL)+C3a low (0.1 μg/ml) or SDF-1 low (10 ng/mL)+C3a (1 μg/ml) or SDF-1 low (10 ng/mL)+C3a$_{desArg}$ (1 μg/ml). Data are pooled from quadruplicate samples from three independent experiments.* p<0.00001.

FIG. 13A-B—Chemotaxis of cells to an SDF-1 gradient is lipid raft-dependent. Panel A: Chemotaxis of CD34+ cells to medium alone (control), SDF-1 (300 ng/mL) and SDF-1 (300 ng/mL) after preincubation for 1 hr with Amphotericin (10 μg/mL) or Nystatin (50 μg/mL). Cells were collected after chemotaxis from the lower chambers and plated in a clonogenic assay. The number of CFU-GM and BFU-E colonies formed by harvested cells is shown as a percentage of control values. Data are pooled from quadruplicate samples from three independent experiments. *p<0.0001. Panel B: Chemotaxis of CD34+ cells towards medium alone (control), SDF-1 low (10 ng/mL) alone, or SDF-1 low with cells exposed to C3a (1 μg/mL). Cells pretreated before chemotaxis for 1 hr with MβCD (2.5 mM) are shown as gray bars. Data are pooled from quadruplicate samples from three independent experiments. * p<0.00001.

Figure 14:
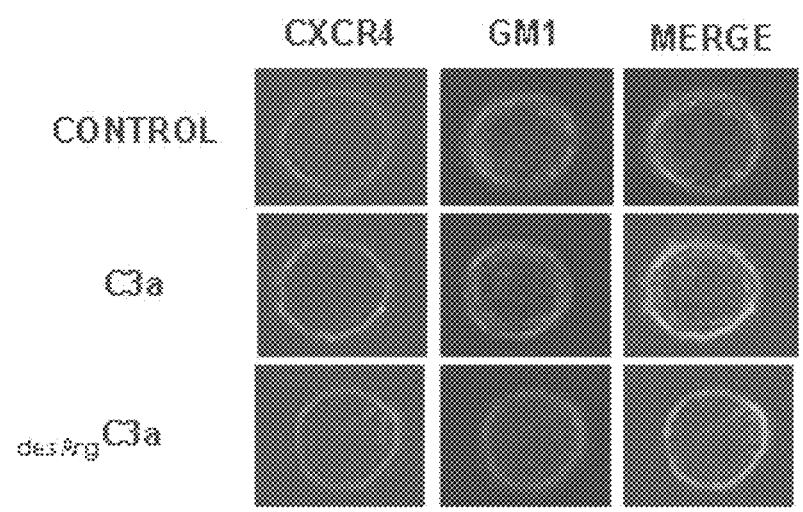

FIG. 14—Priming effect depends on inclusion of CXCR4 into membrane lipid rafts. FIG. 6 comprises three rows and three columns of images of micrographs. Lipid raft formation on normal human UCB-derived CD34+ cells not stimulated (control) or stimulated with C3a or $_{desArg}$C3a. For visualization of lipid rafts, CD34+ cells were fixed in 3.7% paraformaldehyde/Ca- and Mg-free PBS for 15 min and permeabilized by Triton X-100 in PBS for 5 min at room temperature (RT). The primary antibodies used for raft analysis are cholera toxin B-subunit conjugated with Fluorescein Isothiocyanate (FITC) (Sigma Aldrich, St. Louis, Mo.) and mouse monoclonal anti-hCXCR4 immunoglobulin (Ig)G (R&D Systems, Minneapolis, Minn.). After rinsing in phosphate-buffered saline (PBS), the sections were incubated with Alexa Fluor 568 goat anti-mouse IgG (Molecular Probes, Eugene, Oreg.) for 45 min.

Figure 15A:
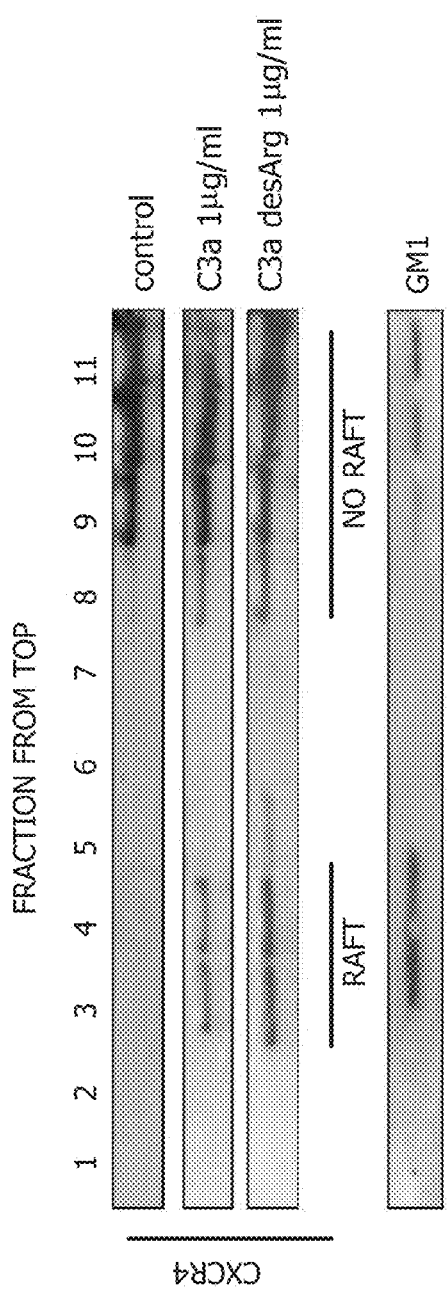
Figure 15B:
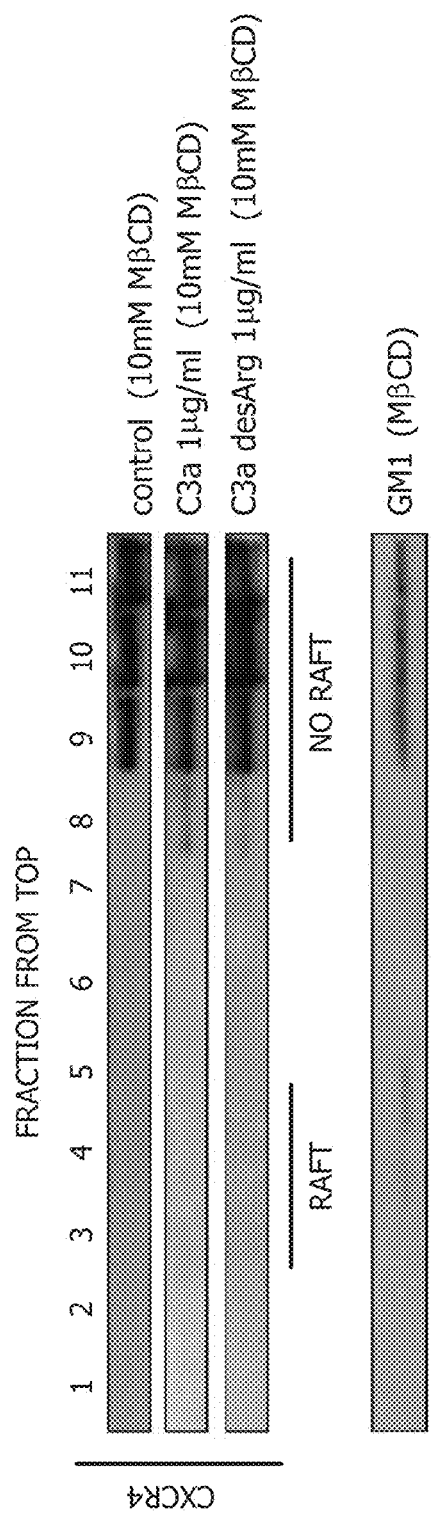

FIG. 15A-B—Western blot analysis of the colocalization of CXCR4 in fractions of cell membranes enriched in lipid rafts (fractions 3-5) and depleted of lipid rafts (fractions 9-11). Panel A: Hematopoietic THP-1 cells were stimulated by C3a (1 µg/mL) or $_{desArg}$C3a (1 µg/mL) or not stimulated (control). CXCR4 was detected in these membrane fractions by Western blot along with ganglioside GM1, a marker of lipid rafts. Experiments were performed three times with similar results. Panel B: In control experiments, cells were pretreated for 1 hr with 10 mM MβCD. A representative study is shown.

FIG. 16A-B—Panel A: C3a primes homing of murine CFU-GM and CFU-S into BM of lethally irradiated mice. Murine BM-derived Sca-1$^+$ cells ($10^5$/mouse) were transplanted into lethally irradiated syngeneic mice. At 16 hrs after transplant, cells were recovered from the femurs of transplanted animals and assayed in secondary cultures for the number of clonogenic CFU-GM (left panel) and, after transplant into secondarily irradiated animals, for the number of day-12 CFU-S (right panel). Data are pooled from three independent experiments using 10 mice each/tested cells (n=30). * p<0.0001. No HSPC cells were recovered from the marrow cavities of control animals (irradiated, not transplanted) Panel B: C3a primes homing of human CB and BM CD34$^+$ cells into the BM of lethally irradiated NOD/SCID mice. At 16 hrs after transplantation of human CD34$^+$ cells ($10^6$/animal), mice were sacrificed and CFU-GM colonies were assayed in methylcellulose cultures. Data are pooled from independent experiments preformed on three different CB- and three different BM samples using 2-4 mice/tested cell sample. p<0.0001.

Figure 17A:
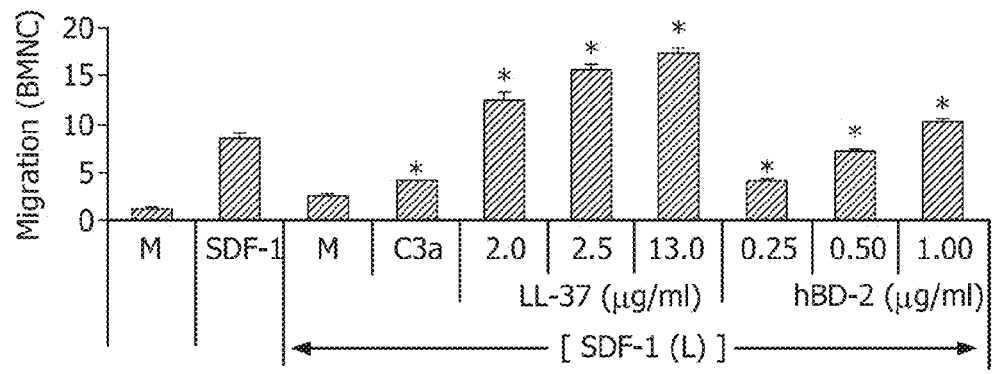
Figure 17B:
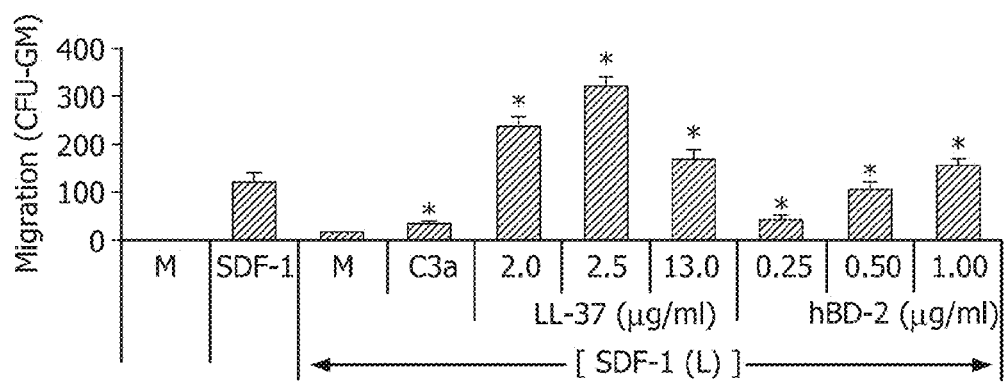

FIG. 17A-B—Cationic peptides released from granulocytes enhance responsiveness of HSPCs to SDF-1 gradient. Recombinant cationic peptides LL-37 and hBD-2 strongly enhanced migration of murine BMNCs (17A) and CFU-GM progenitor cells (17B) in response to SDF-1 gradient. Values are the fold increases of migrated cells compared to media alone. M, media alone; SDF-1 (L), 50 ng/ml; SDF-1 (H), 300 ng/ml; C3a, 1 µg/ml. * P<0.05 as compared with SDF-1 (50 ng/ml) alone. The data shown represent the combine results from four independent experiments carried out in triplicate per group (n=12).

FIG. 18A-B—Priming effect of cationic peptides is dependent on enhanced incorporation of CXCR4 into lipid rafts. (A) Western blot analysis of the localization of CXCR4 in various fractions of cell membranes. Membranes enriched in lipid rafts (fractions 3-5) and depleted of lipid rafts (fractions 9-11). Human pre-B cell line, Nalm-6, was stimulated with (5 µg/ml) β2-defensin (hBD-2) (250 ng/ml) or was not stimulated (control). CXCR4 was detected in these membrane fractions by Western blot along with Lyn, a marker of lipid rafts. Experiments were performed three times with similar results. (B) LL-37-induced enhancement of THP-1 cell migration to SDF-1 gradient was inhibited by 1 h pretreatment with MβCD (1.0 or 2.5 mM). * P<0.05 as compared with migration of control cells in the absence of LL-37 (2.5 µg/ml). Lipid raft formation was analyzed. Shown are representative of three independent experiment carried out in triplicate per group. The data shown represent the combine results from four independent experiments carried out in triplicate per group (n=12).

Example 3

Figure 19:
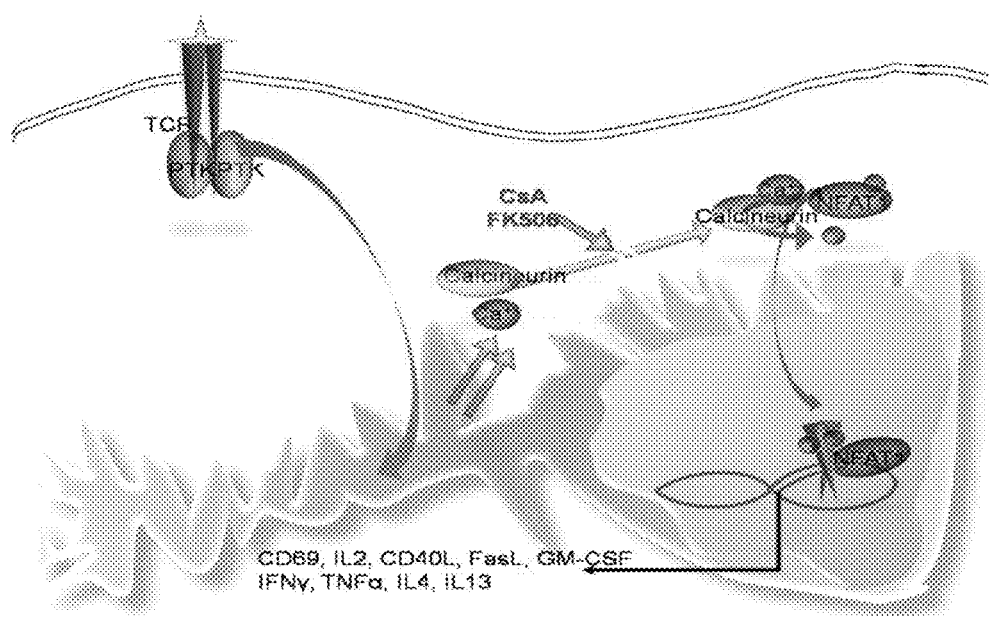

FIG. 19—NFAT1 ACTIVATION CASCADE. Schematic diagram illustrating that NFAT1 resides in phosphorylated latent form in the cytoplasm. Increase of intracellular $Ca^{2+}$ concentration (TCR activation) results in activation of the phosphatase calcineurin, which then dephosphorylates NFAT1. Dephosphorylation of NFAT1 results in increased DNA affinity, translocation to the nucleus, and transcriptional activation of numerous immunomodulatory molecules. NFAT1, depending on the target gene, binds promoter elements alone and/or forms transcription complexes with other transcription factors including AP-1 and FoxP3.

Figure 20:
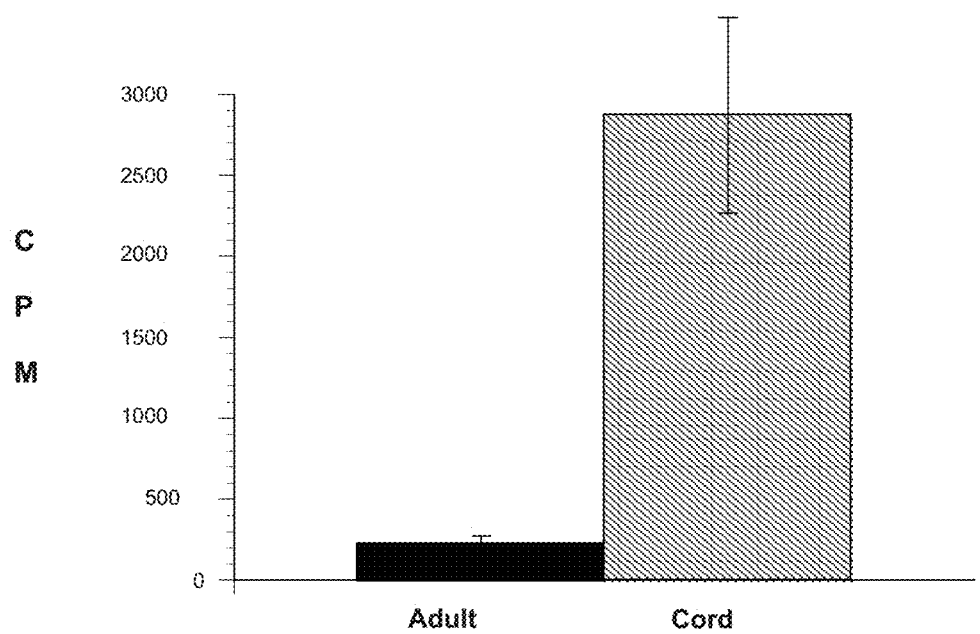

FIG. 20—Higher rates of proliferation in UCB T-cells as compared to adult. T-cells isolated from NFAT1 gene deleted mice demonstrate markedly increased proliferation in the absence of any external stimulation. We measured proliferation in absence of stimulation in human UCB T-cells, and noted that after 24 hours of culture, UCB proliferation was significantly greater than adult (2870±603 cpm for UCB vs. 225±47 cpm for adult) (FIG. 20). $0.2 \times 10^6$ T-cells were plated in triplicate and pulsed with 1 µCi of $^3$H-thymidine (Amersham, Buckinghamshire, UK), cultured for 24 h in 96-well plates, and harvested onto glass fiber filtermats (Wallac, Turku, Finland) using a Harvester 96 (Tomtec Inc., Hamden, Conn.). Incorporated $^3$H-thymidine was measured using a MicroBeta Trilux scintillation counter. Reduced NFAT1 expression in human UCB T-cells was associated with this measured increased rate of proliferation (data not shown). These results correlated with observations by other investigators, and our subsequent gene array studies demonstrating the up-regulation of cell cycle proteins cyclin A2, cyclin E2, $p21^{cip1/waf}$ in UCB CD4$^+$ T-cells as compared to adult.

FIG. 21A-C—Rescue of IFN-γ expression in UCB T-cells after IFN-γ-induced up-regulation of NFAT1. 21A—Adult; 21B—cord; 21C—IFN-γ

Figure 22A:
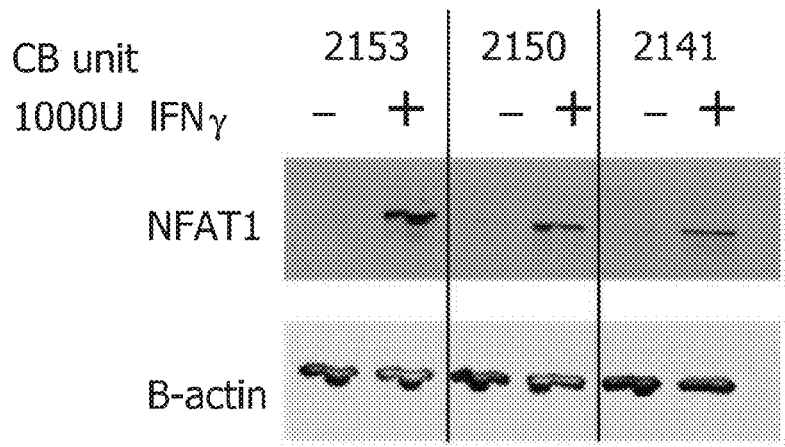
Figure 22B:
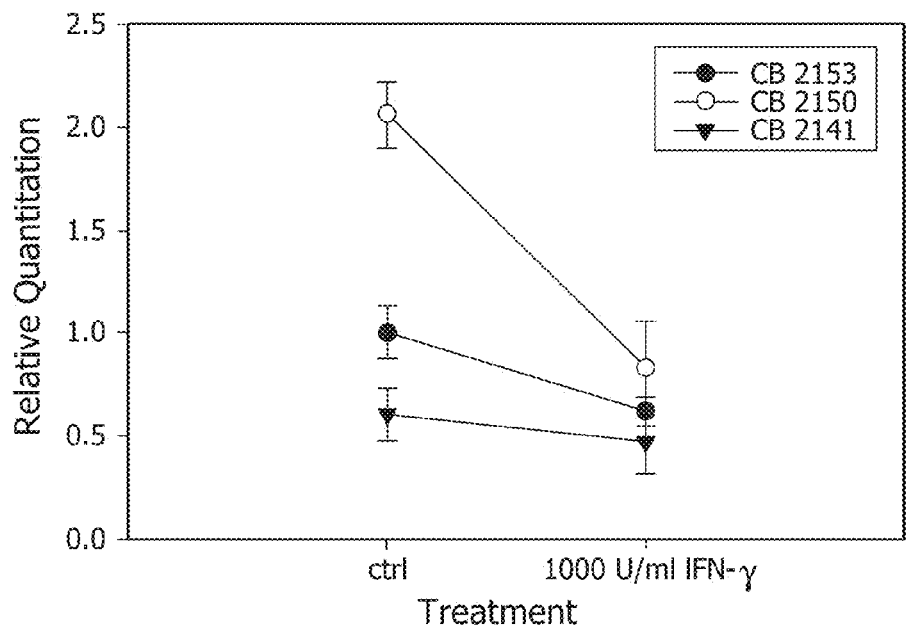

FIG. 22A-B—Rescue of NFAT1 protein in UCB CD4 T-cells during primary stimulation in the presence of exogenous IFN-γ. UCB CD4 T-cells were stimulated with αCD3/CD28 for 24 h with 1000 U/ml of exogenous rh-IFN-γ. Cell lysates were harvested and Western Blot was probed for NFAT1 and β-actin. NFAT1 was noted to increase in UCB CD4 T-cells treated with rh-IFN-γ (22A). qRT-PCR for mir-184 was also observed to decrease in UCB CD4 T-cells treated with exogenous IFN-γ during primary stimulation (22B).

FIG. 23A-B—Adult CD4$^+$CD45RA$^+$ T-cells lack expression of BACH2 in the presence of normal NFAT1 expression. Examination of our prior gene array data showed that BACH2, a bZIP transcription factor with no previously known function in adult human T-cells was up-regulated compared to adult CD4 T-cells. Western blot confirmed absence of BACH2 in adult CD4 T-cells with normal NFAT1 protein expression (23A). These differing BACH2 expression levels comparing UCB vs. adult were confirmed in selected CD4$^+$/45RA$^+$ T-cells (23B).

FIG. 24A-C—a.) qRT-PCR analysis of NFAT1 and NFAT1-dependent IL-2 gene in UCB CD4$^+$/45RA$^+$ T-cells transfected with BACH2 siRNA. Relative expression is compared to the level in control (scrambled) siRNA transfected UCB CD4$^+$/45RA$^+$ T-cells. Results are the average of three separate knockdown transfections with three different UCB units [**=(p<0.002)]. Error bars represent (SEM). b./c.) IL-2 protein expression in primary UCB CD4$^+$ T-cells transfected with BACH2 siRNA. Whole cell extracts of un-stimulated as well as 6 h stimulated UCB CD4$^+$/45RA$^+$ T-cells were analyzed by Western Blot.

Figure 25:
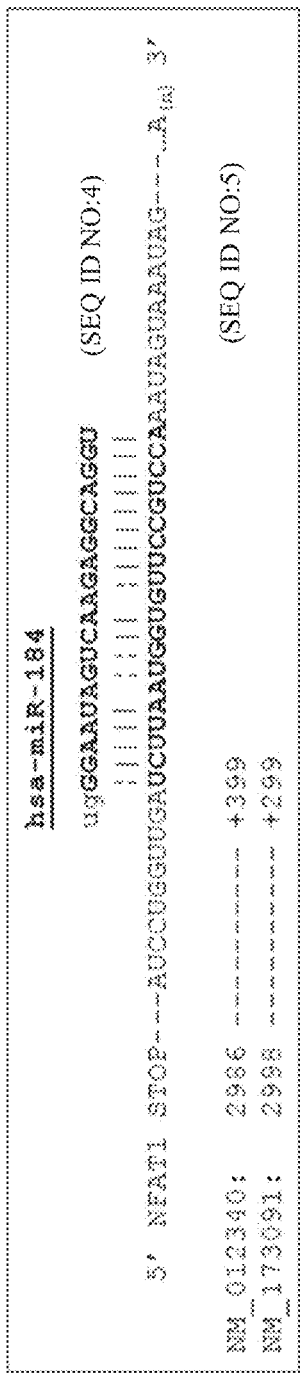

FIG. 25—miR-184 Regulation of NFAT1 in UCB CD4$^+$ T Cells. Complementary miR-184 (SEQ ID NO:4)/NFAT1 (SEQ ID NO:5) sequences are diagrammed, with the predicted interaction occurring 399 and 299 nucleotides downstream of the stop codons respectively.

Figure 26:
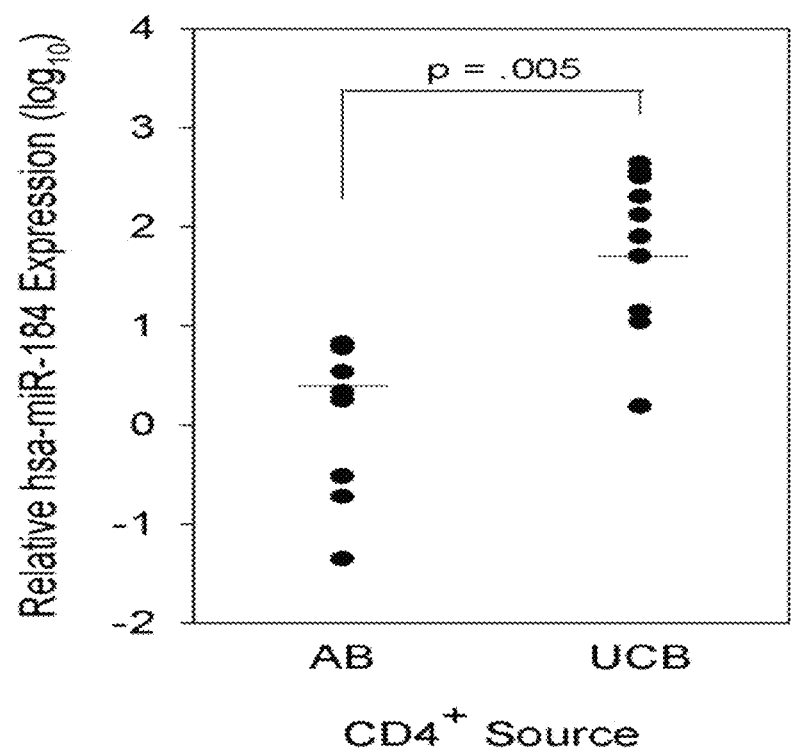

FIG. 26—miR-184 Expression in UCB vs. adult CD4+ T-cells. Unstimulated CD4+ T cell lysates from UCB and adult were analyzed for mir-184 expression levels. N=6. If hsa-miR-184 regulates translation of NFAT1 specifically in UCB naïve CD4+ T-cells, we hypothesized that hsa-mir-184 would be more highly expressed in UCB CD4 T-cells compared to adult. Unstimulated CD4 T-cell lysates were enriched for small RNAs with the Sigma MISSION™ Small RNA isolation kit. RT-PCR was carried out with specific hairpin TaqMan™ RT primers for hsa-miR-184 (Applied Biosystems). FIG. 26 outlines that UCB CD4 T-cells express between 20 and 50 times more hsa-miR-184 than adult CD4+ cells. Results were confirmed in UCB vs. adult selected CD4+ CD45RA+ T-cells (data not shown).

FIG. 27A-B—Western Blot and RT-PCR of NFAT1 following transfection of decoy sequence to hsa-miR-184. Quantification and representative blot of NFAT1 protein expression in UCB CD4+ T-cells 16 hours following transfection with antisense to hsa-miR-184. A) Manipulation of NFAT1 levels in UCB T cells (n=3). B) NFAT1 expression in adult T cells (n=4).

FIG. 28A-B—Loss of BACH2 expression results in reduced Fox3 expression in UCB CD4+/45RA+ T-cells. 28A—graph; 28B—blot FIG. 29A-B—A.) Schematic of the genomic region surrounding hsa-miR-184. Dots denote CpG sites and a putative CpG island (defined by observed/expected CpG incidence>0.06, GC>50%, length>100 bp) located closely upstream. B) Adult CD4 T-cells were cultured with and without the DNA methyltransferase blocker 5-aza deoxycytidine (5-aza) for 24 h, a portion stimulation for 6 h, then assayed for miR-184 expression by RT-PCR.

FIG. 30A-B—UCB MNC migration to SDF-1. Lymphocytes from SSC/FSC plots were gated to determine the number of transmigrating UCB CD45+CD4+ T-cells. A. The total number of transmigrated lymphocytes migrating without and with C3a priming prior to exposure to 10 ng/ml SDF-1 (mean±SD). B. Within this lymphocyte gate, two populations of CD45+CD4+ cells (gates P2 and P3) were observed to be labeled with anti-CD4-PerCP antibody. Labeling of Ficoll-isolated, non-primed MNC with anti-CXCR4-FITC antibody (BD Biosciences) showed 9.3% of the gated lymphocytes expressed the CXCR4 receptor. All staining patterns of labeled cells were compared to cells incubated with APC- and PerCP-isotype antibodies to set negative quadrants gates.

FIG. 31A-B—UCB CD4+45RA T-cell migration to SDF-1. Transmigrated selected naïve CD45+CD4+ cells (using the same UCB units as in FIG. 12) were displayed on CD4-PerCP versus CD45-APC plots from an initial SSC/FSC plot. A. Percentage of selected CD4+/45RA+ T-cells transmigrating without and with C3a priming prior to exposure to 10 ng/ml SDF-1 (mean±SD). B. CD45+CD4+ T-cells were observed only in gate P3 in contrast to the transmigration of MNC. Labeling of non-primed selected CD4+ T-cells with anti-CXCR4-FITC antibody showed 8% of the gated naïve CD45+ CD4+ T-cells expressing the CXCR4 receptor.

Example 4

Figure 32:
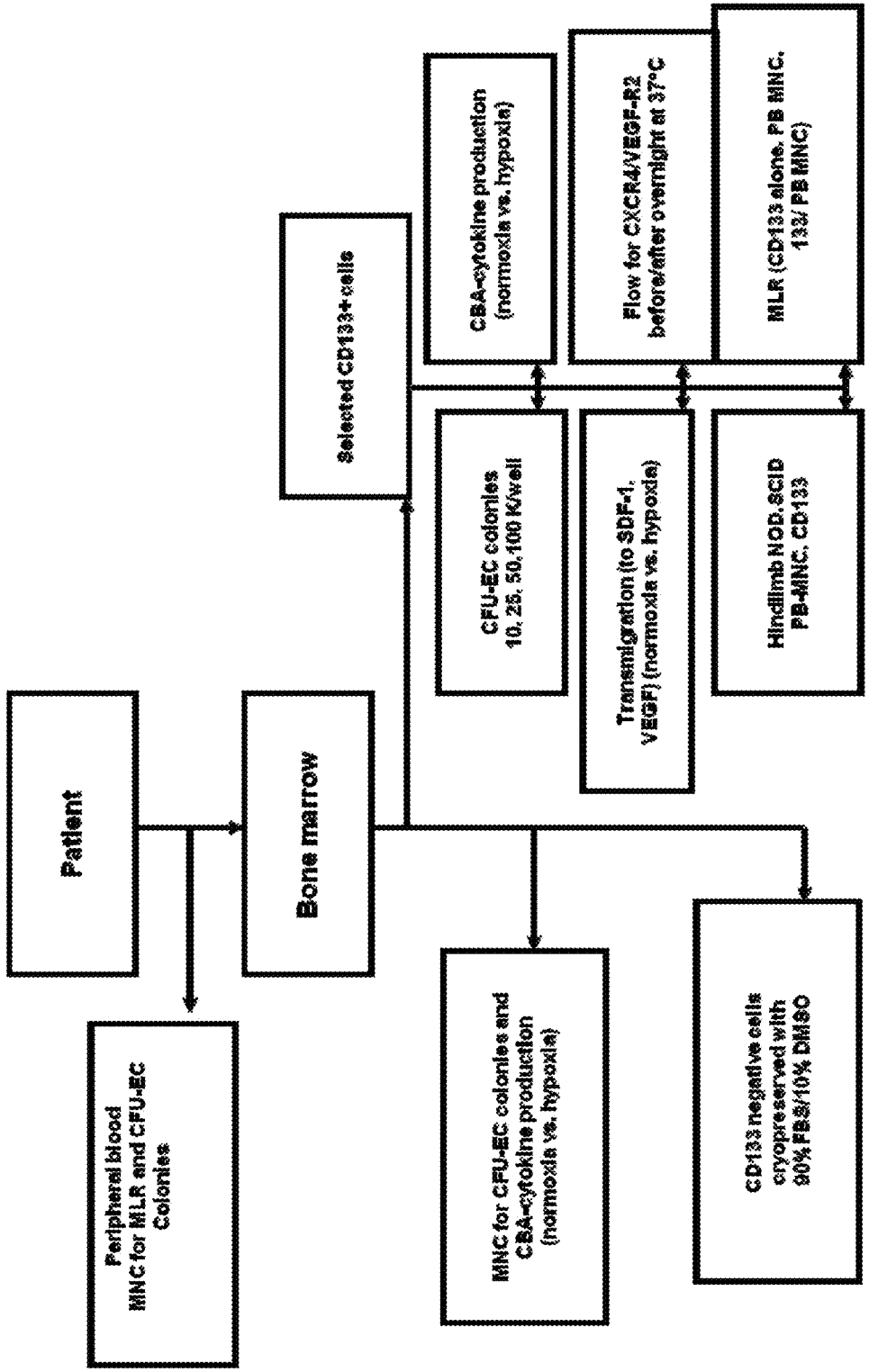

FIG. 32—Correlative Studies: CD133 in Coronary Ischemia schematically illustrates correlative studies of CD133 in coronary ischemia.

FIG. 33—Summary of phase I clinical trial patient BM cell counts and sterility results a table summarizing the results of a phase I clinical and provides BM cell counts, sterility results, etc. for nine subjects.

Figure 34:
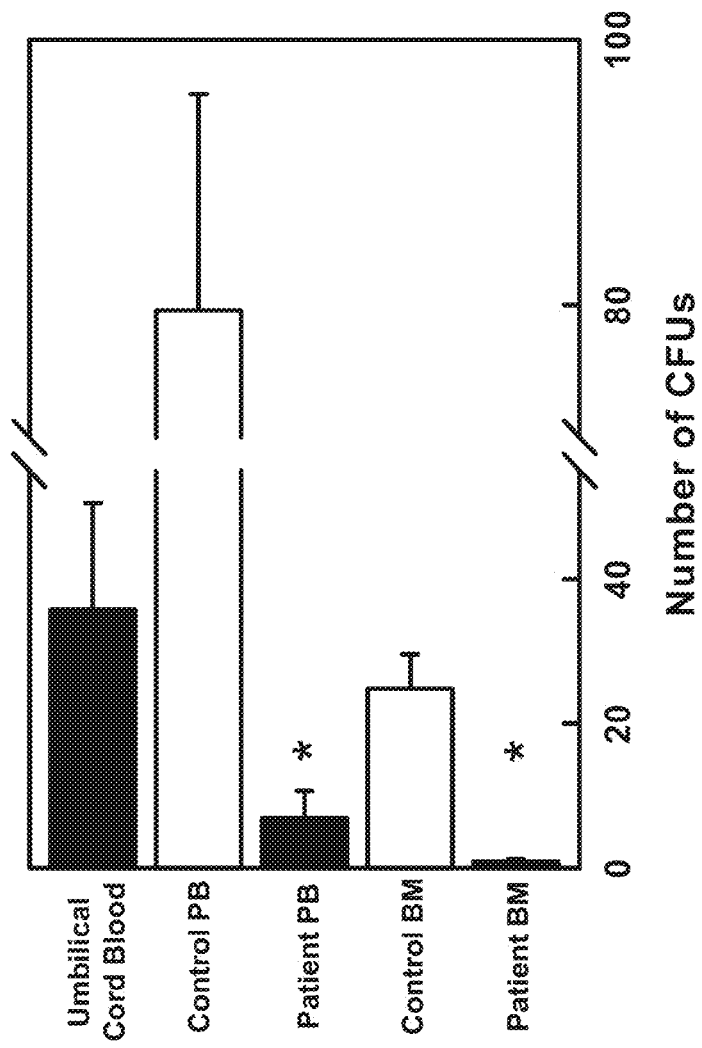

FIG. 34—Age and Disease-Related Diminution in CD133 Angiogenic Function graphically illustrates age and disease-related diminution in CD133 angiogenic function. Groups include umbilical cord blood, control PB, patient PB, control BM, and patient BM. Results are expressed as Number of CFUs.

Figure 35:
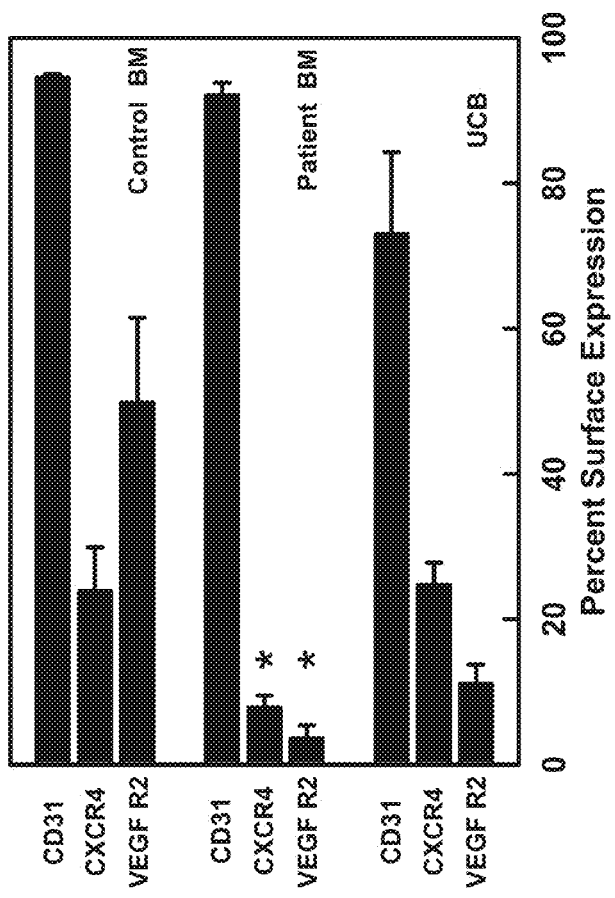

FIG. 35—Age and Disease-Related Diminution in CD133 Angiogenic Function Expression of Chemotactic Receptors graphically illustrates age and disease-related diminution of CD133 angiogenic function and the expression of chemotactic receptors. Groups include CD31, CXCR4, and VEGFR2 for control BM, Patient BM and UCB. Results are expressed as Percent Surface Expression.

Figure 36:
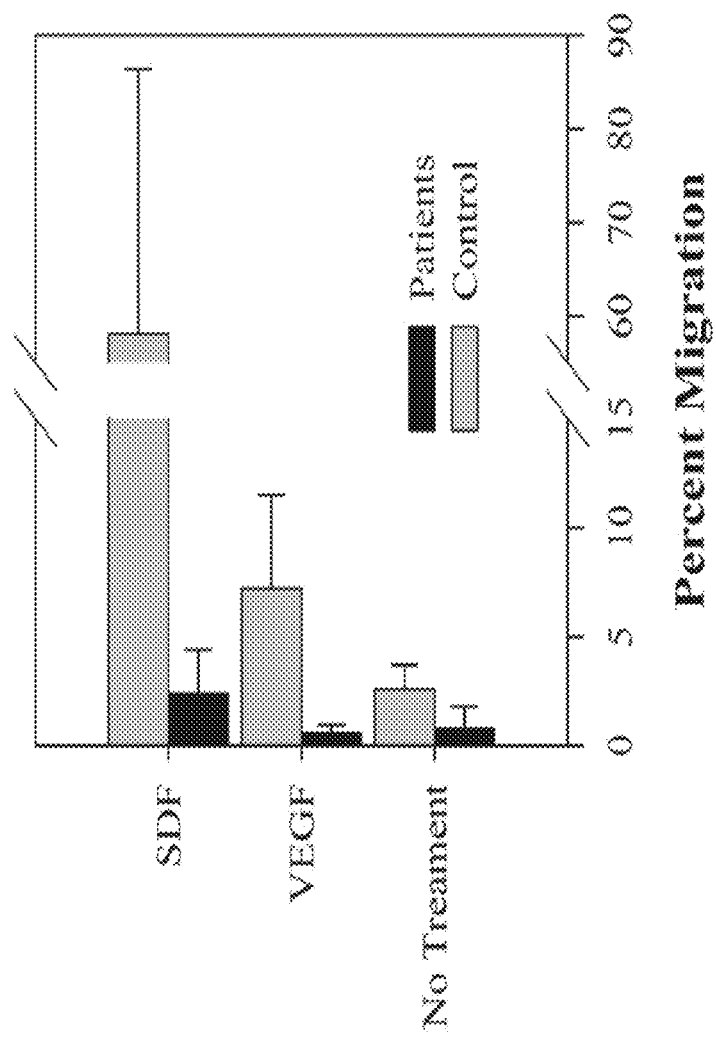

FIG. 36—Age and Disease-Related Diminution in CD133 Angiogenic Function Transmigration to SDF-1 and VEGF graphically illustrates age and disease-related diminution in CD133 angiogenic function and the transmigration to SDF-1 and VEGF. Patients and controls were tested for transmigration with SDF-1, VEGF, or no treatment. Results are expressed as Percent Migration.

Figure 37:
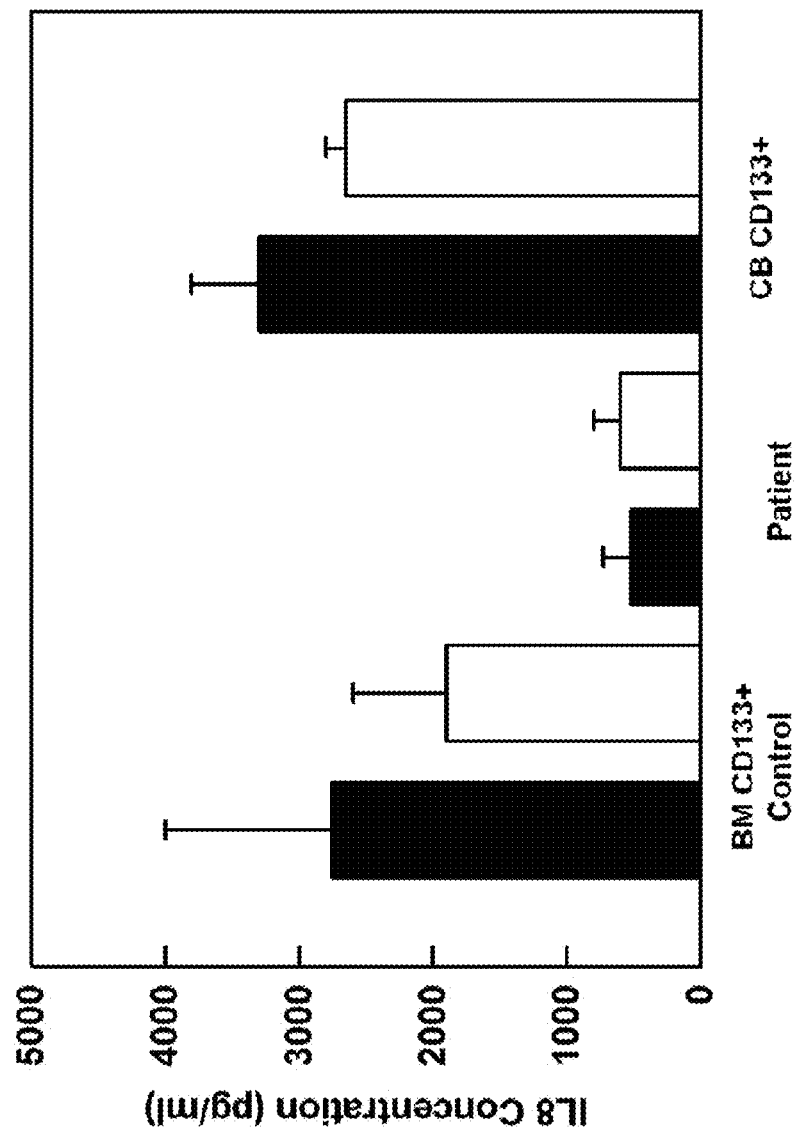

FIG. 37—Age and Disease-Related Diminution in CD133 Angiogenic Function graphically illustrates the results of an experiment studying age and disease-related diminution in CD133 angiogenic function as related to IL8 concentration. Groups include BM CD133+ Control, Patient, and CB CD133+.

Figure 38:
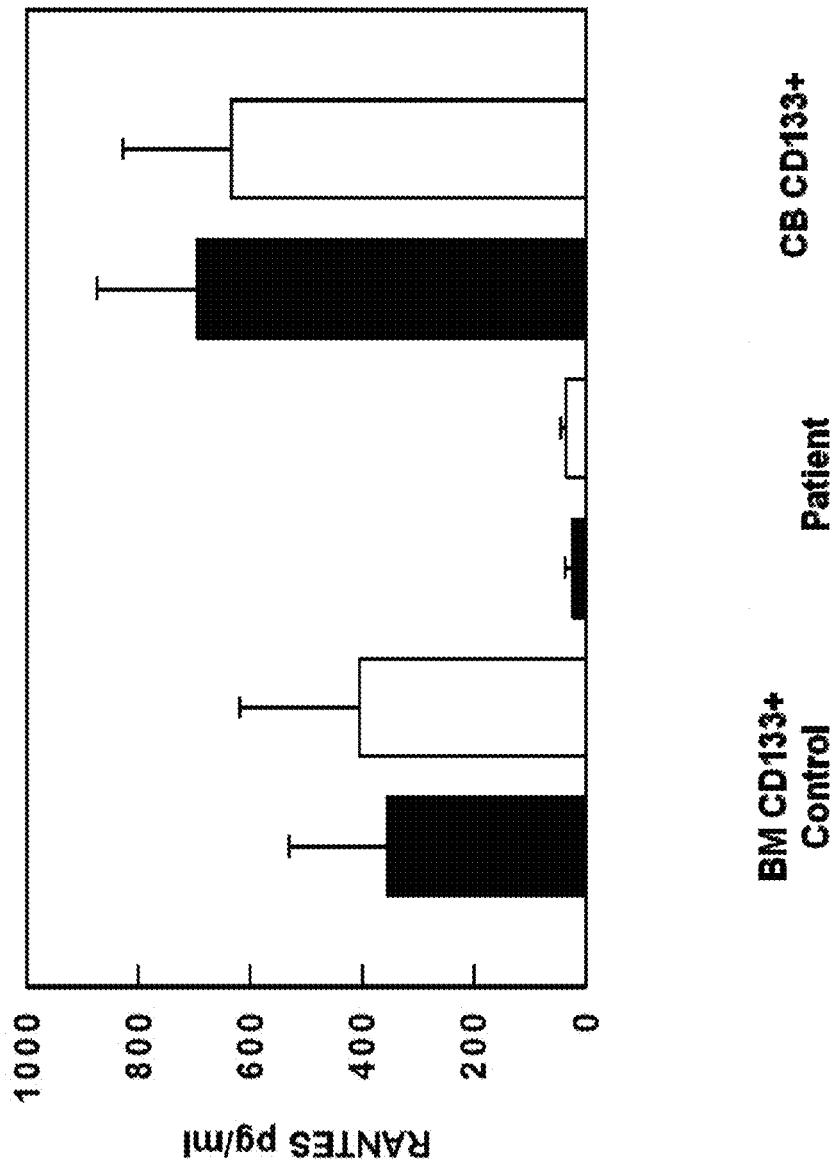

FIG. 38—Age and Disease-Related Diminution in CD133 Angiogenic Function graphically illustrates the results of a study on age and disease-related diminution in CD133 angiogenic function and Rantes. Groups include BM CD133+ Control, BM CD133 Patient, and CB CD133+.

Figure 39:
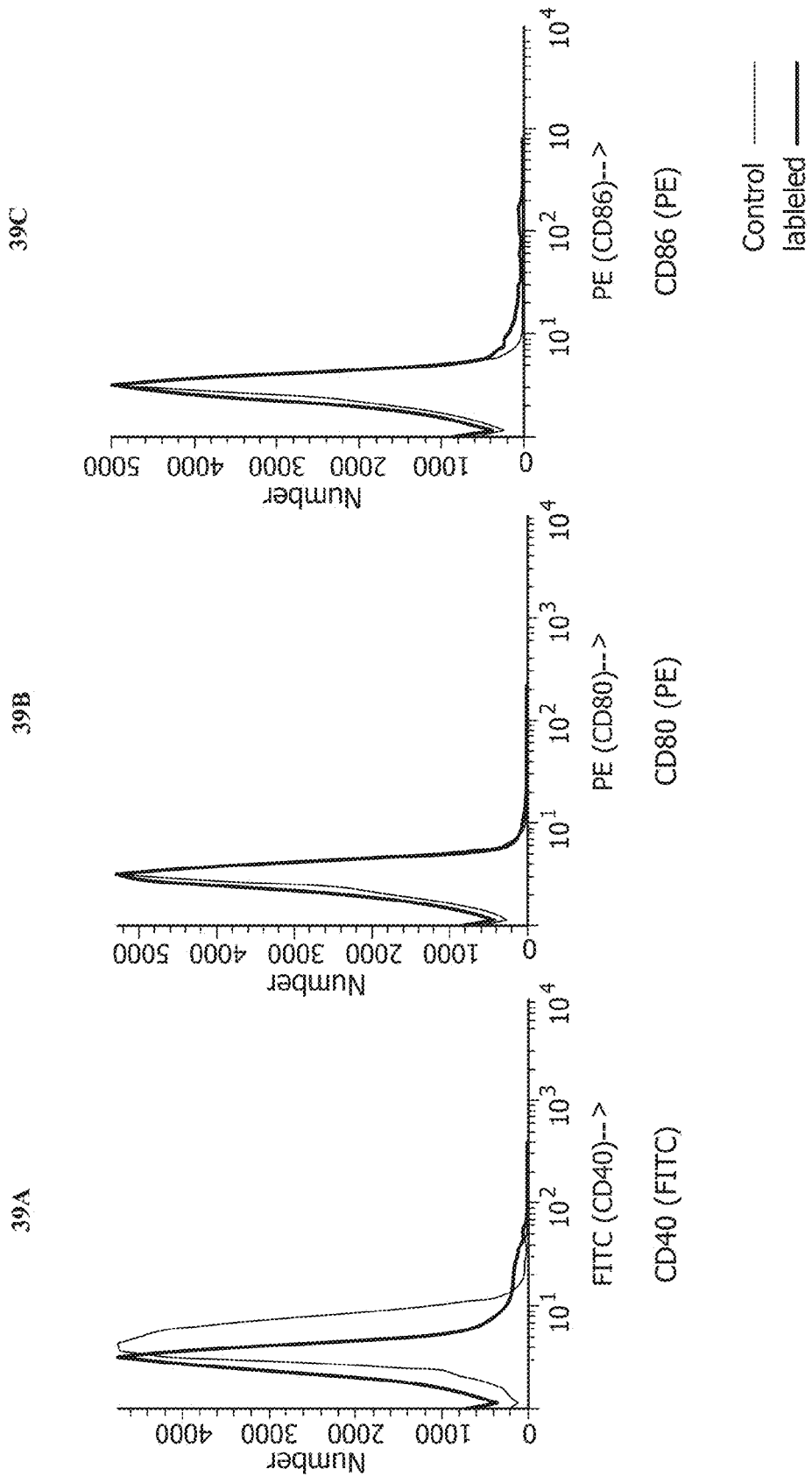

FIG. 39A-C—Co-Stimulatory Antigen Expression on UCB-Derived CD133 comprising three panels, graphically illustrates the results of an experiment on co-stimulatory antigen expression on UCB-derived CD133 cells. The left panel represents CD40 (FITC), CD80 (PE) and CD86 (PE).

Figure 40:
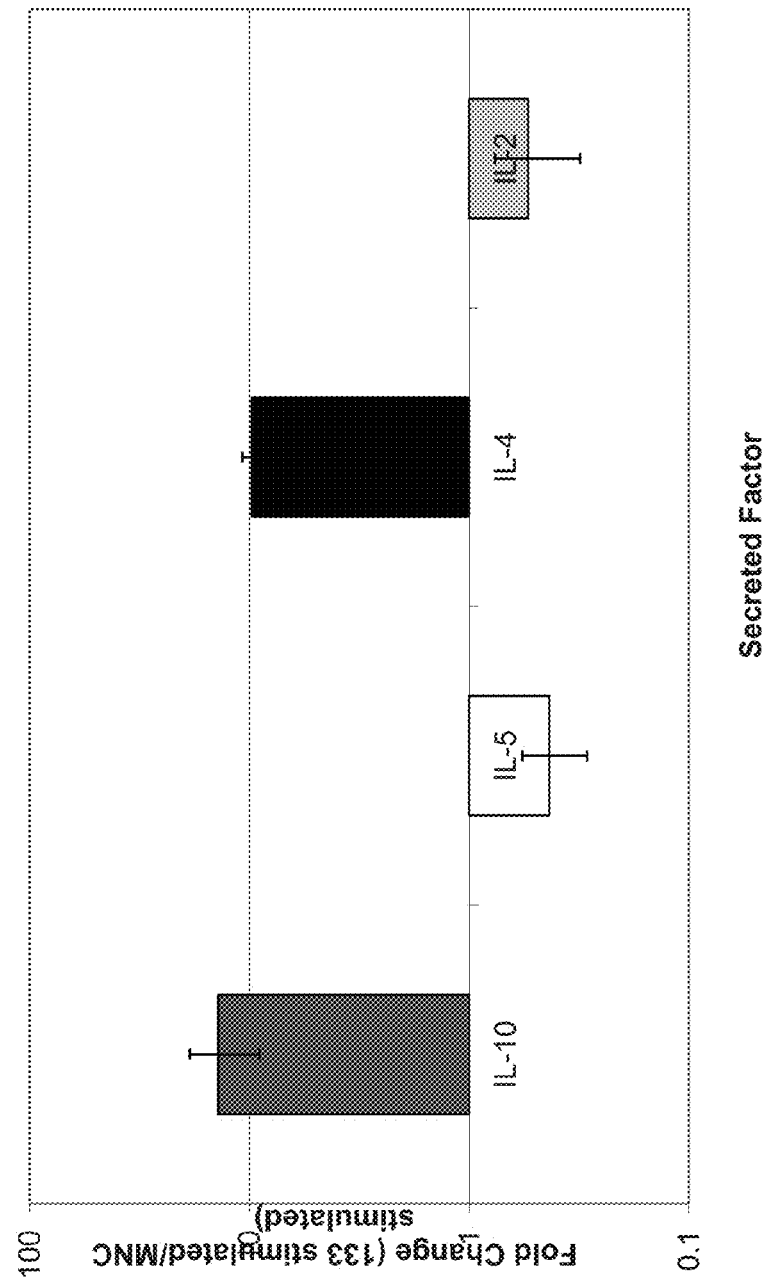

FIG. 40—UCB CD133+ are defective APC and induce TH2 immune responses in MLR graphically illustrates the results of a study demonstrating that UCB CD133+ are defective APC and induce TH2 immune responses in MLR. Groups include IL-10, IL-5, IL-4, and IL-2. The ordinate represents Fold Change (133 stimulated/MNC stimulated) and the abscissa represent the secreted factor.

Example 5

Figure 41:
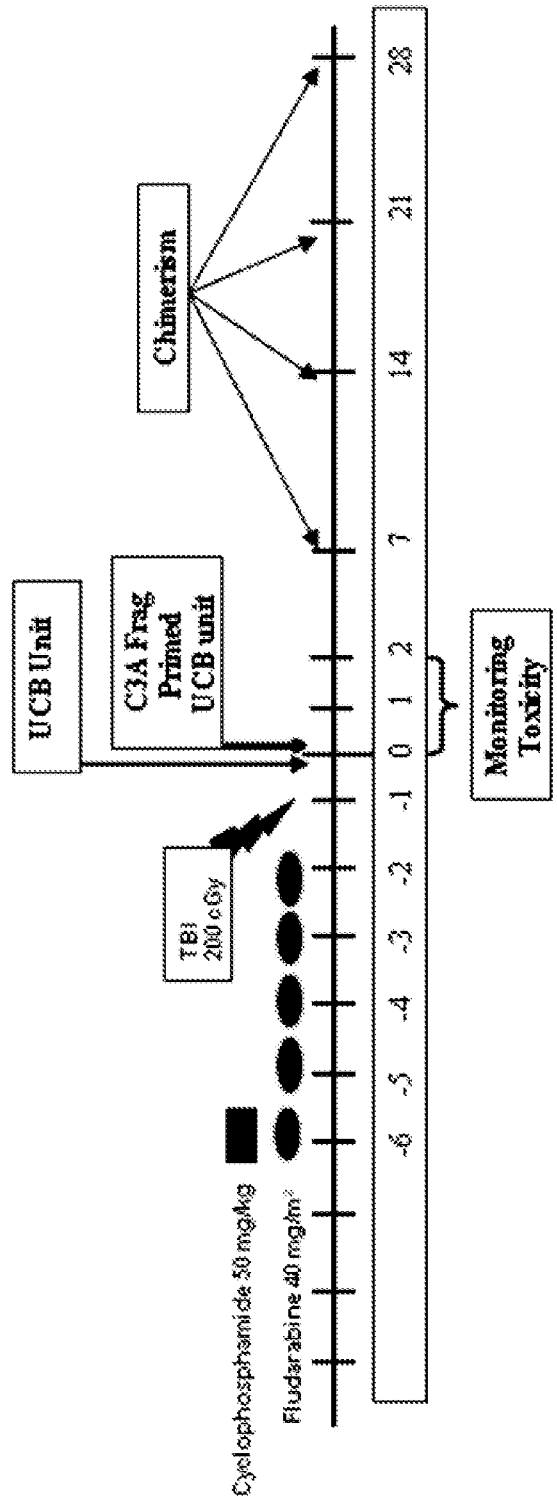

FIG. 41—Treatment Schema. This was a non-randomized pilot phase I/II study of the safety and efficacy of the incubation of one of two umbilical cord blood units with complement fragment 3a (C3a). After thawing, the unit with lower cryopreserved nucleated cell dose was primed with the C3a for 30 min, and infused immediately after the infusion of the unmanipulated unit. This approach was based on the fact that the larger unit offers the best chance for engraftment should the manipulation damage the 'engraftability' of the smaller unit.

Figure 42A:
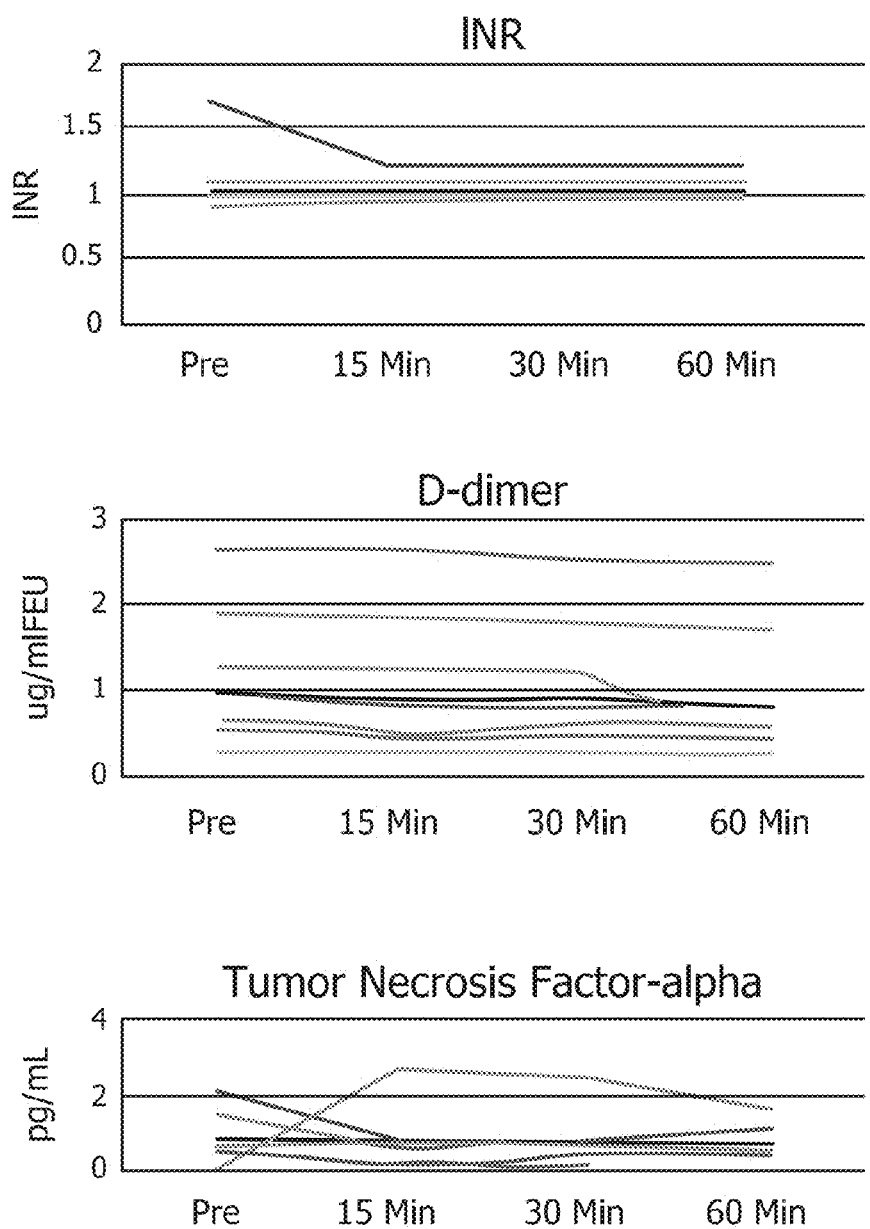
Figure 42C:
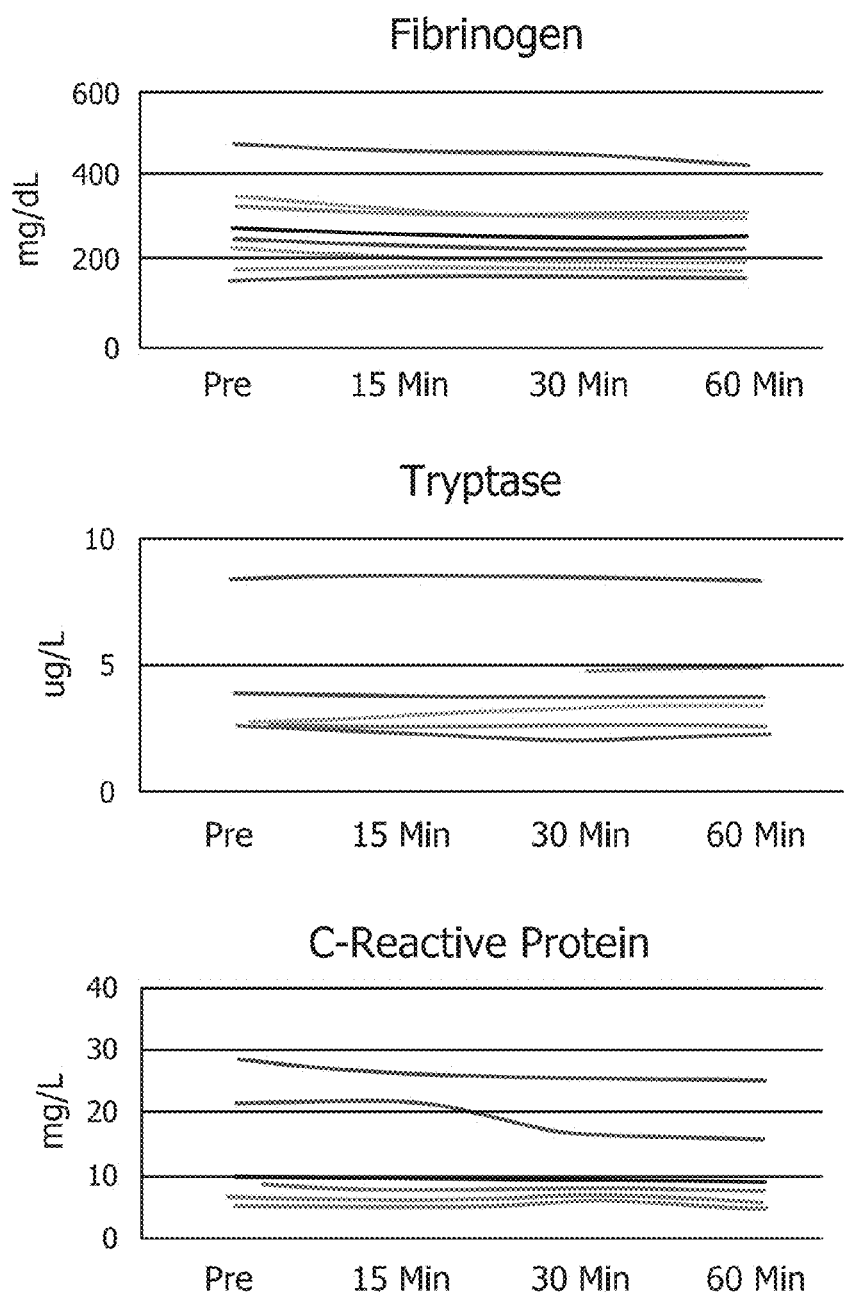

FIG. 42A-C—Effect of C3a primed UCB on downstream pathways. There was no effect of the infusion of C3a primed UCB on any downstream pathways including INR (42A), partial thromboplastin time (42B), serum fibrinogen (42C), d-dimer (42A), histamine (42B), tryptase (42C), C-reactive protein (42C), nor plasma levels of IL-6 (42B) or TNF-alpha (42A) (nine panels).

Figure 43:
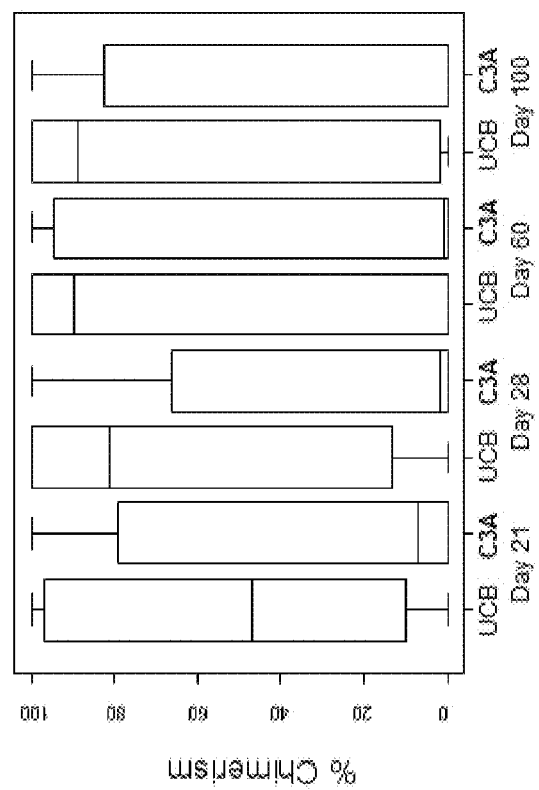

FIG. 43—% chimerism Day +21. The C3a primed unit was noted to predominate at day 21 as assessed by chimerism in 6 of 10 patients, with 3 of the non-primed units predominant at this time point, and one patient was non-evaluable due to technical difficulty with the non-primed unit requiring infusion of a backup unit.

Figure 44:
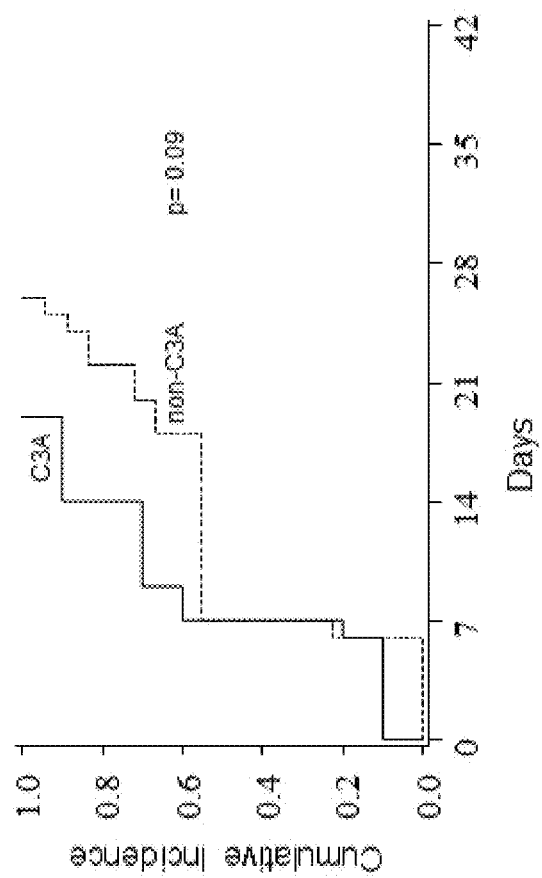

FIG. 44—Absolute Neutrophil Engraftment Comparing C3a and non-C3a primed UCB units. Although a trend toward faster neutrophil engraftment was observed in C3a primed UCB units, this trend did not attain statistical significance (p=0.09).

Figure 45:
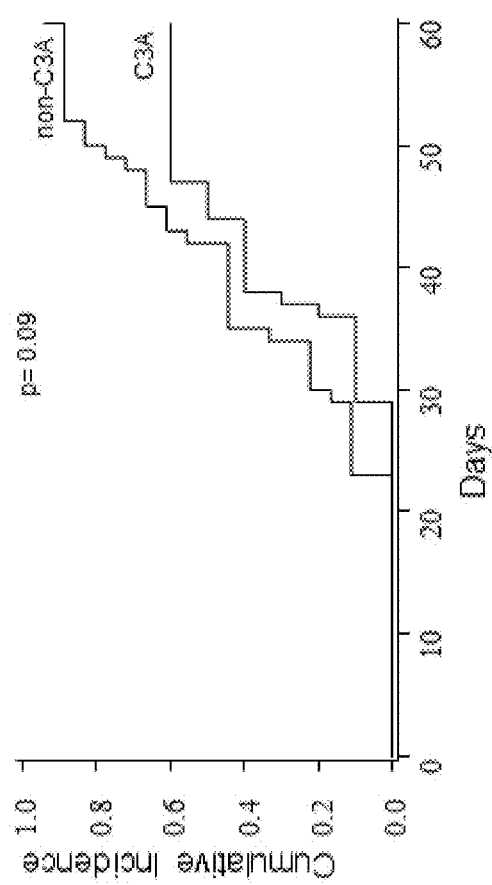

FIG. 45—Kaplan Meier Estimate of platelet engraftment comparing C3a primed UCB units vs. non-C3a.

Figure 46:
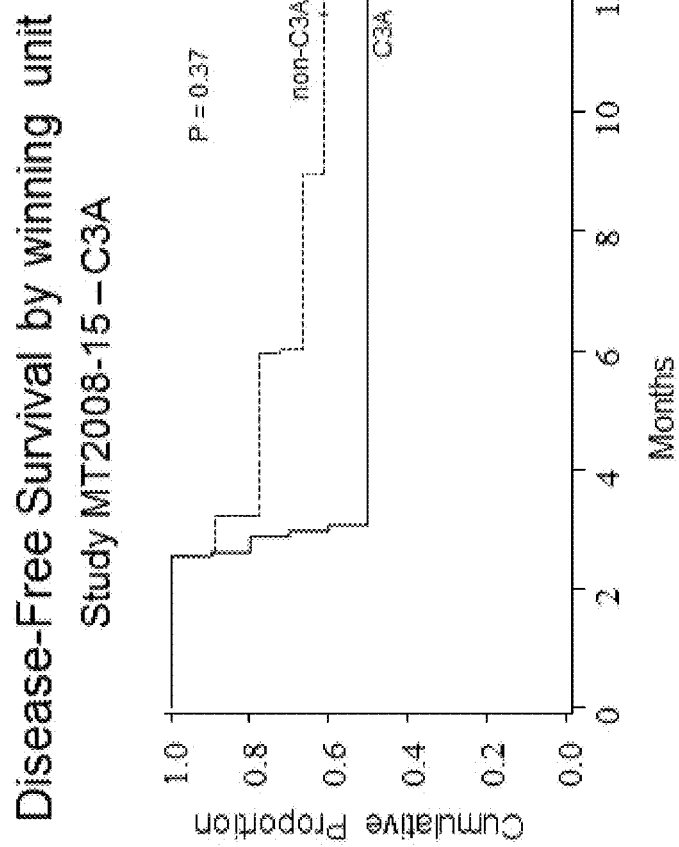

FIG. 46—Kaplan Meier Estimate of Disease Free Survival comparing C3a primed UCB vs. non-C3a primed. No difference in DFS was noted comparing C3a primed UCB vs. non-C3a primed.

FIG. 47—Analyses UCB CD3 T-cell doses infused comparing C3a Primed UCB units vs. non-C3a Primed. As the design of the study incorporated C3a priming of the smaller unit in patients receiving 2 unit UCB, we analyzed CD3 T-cell doses infused in the first 10 study patients. CD3+ T-cells infused in non-C3a primed units was significantly higher (p<0.01).

Figure 48:
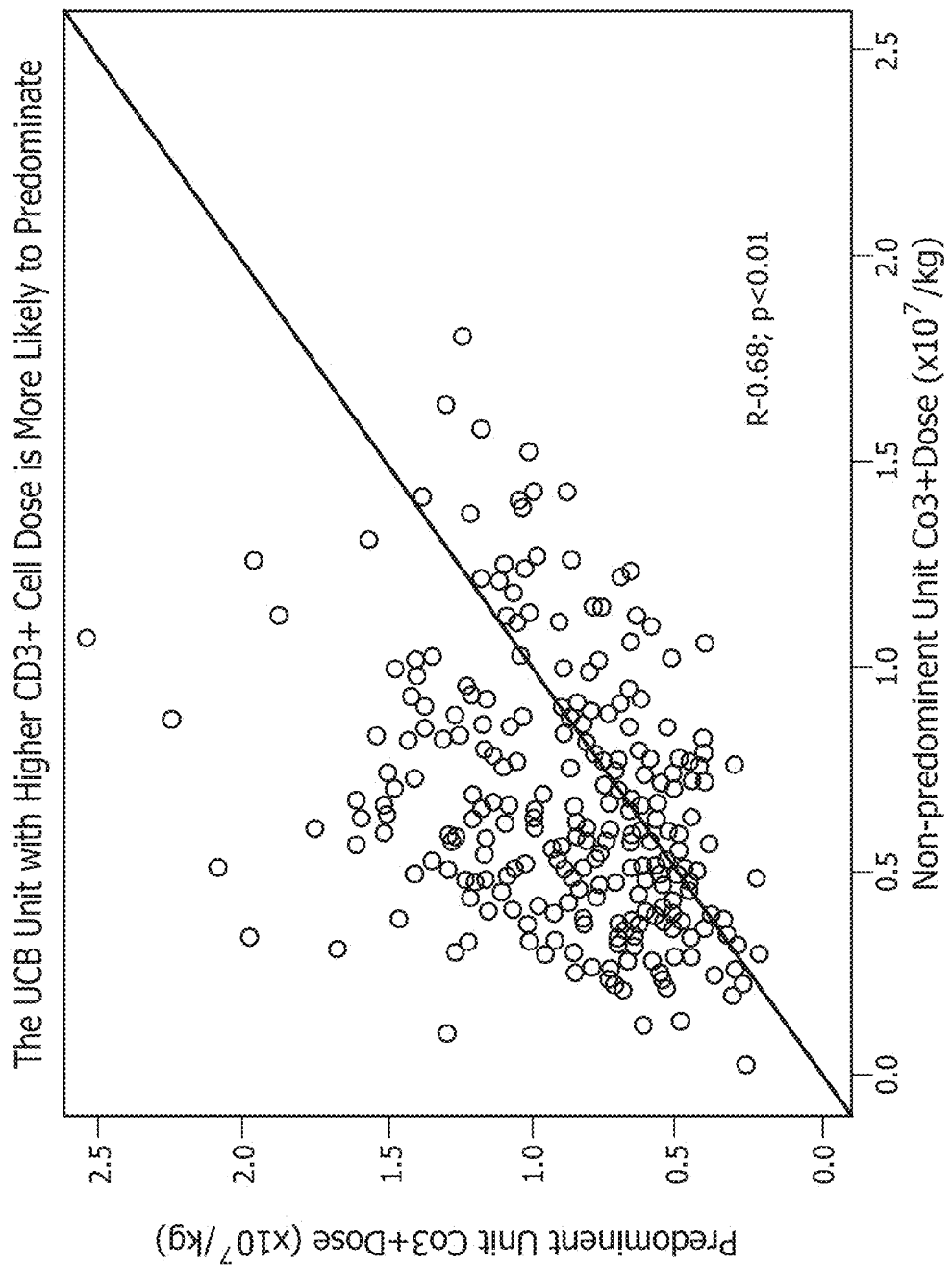

FIG. 48—Analyses UCB CD3+ T-cell dose infused. Recent analyses have demonstrated that UCB grafts with higher CD3+ T-cell dose are more likely to engraft in the patient. This observation may have implications in the results of our clinical trial incorporating C3a priming as T-cell doses of C3a primed units was significantly lower than that of non-C3a units.

Figure 49:
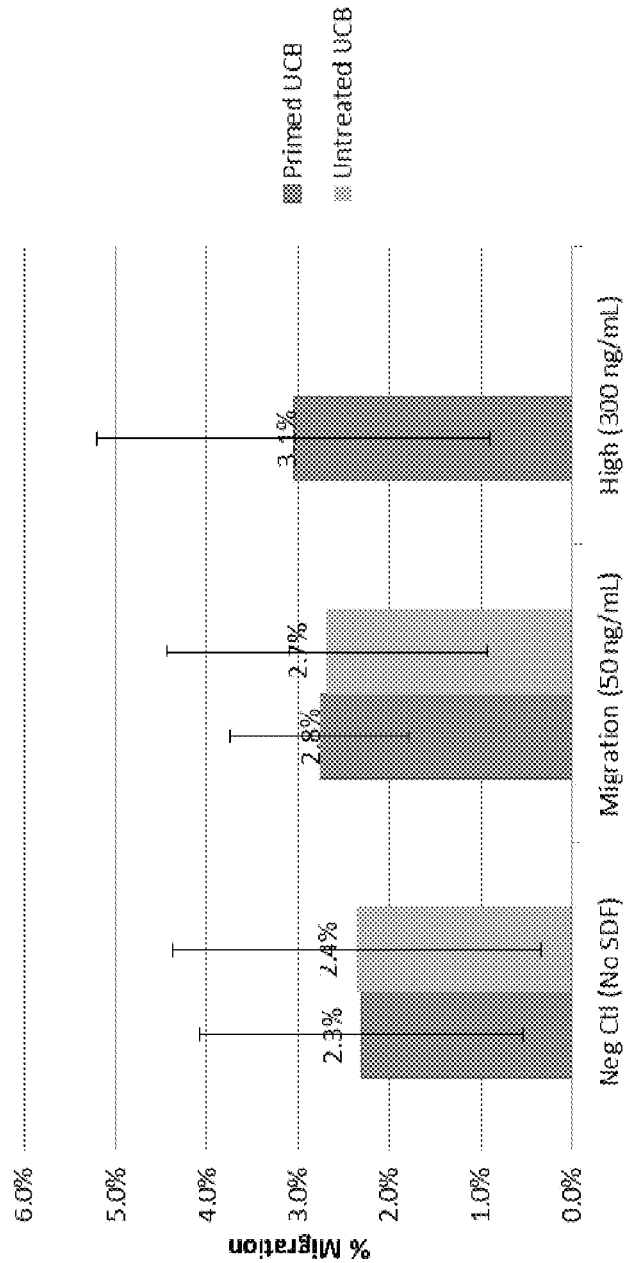

FIG. 49—UCB C3a SDF Gradient Summary.

Figure 50:
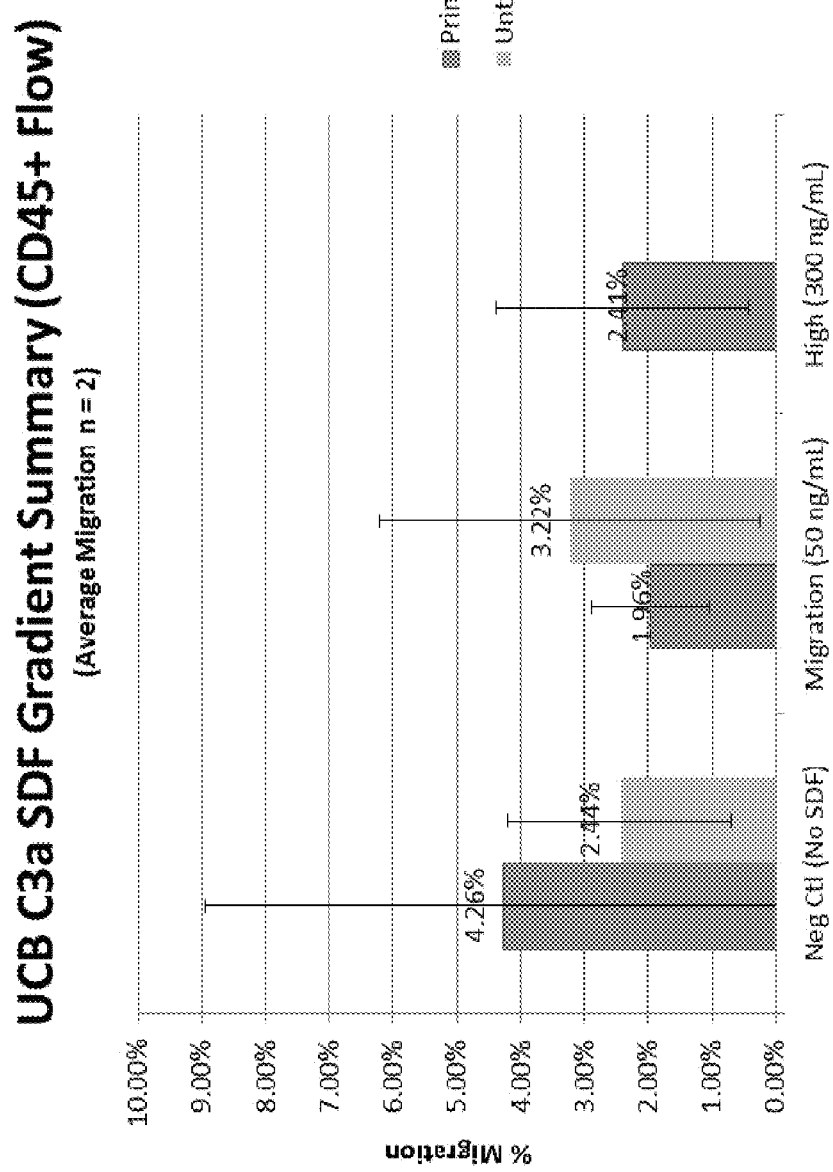

FIG. 50—UCB C3a SDF Gradient Summary (CD45+ Flow).

Figure 51:
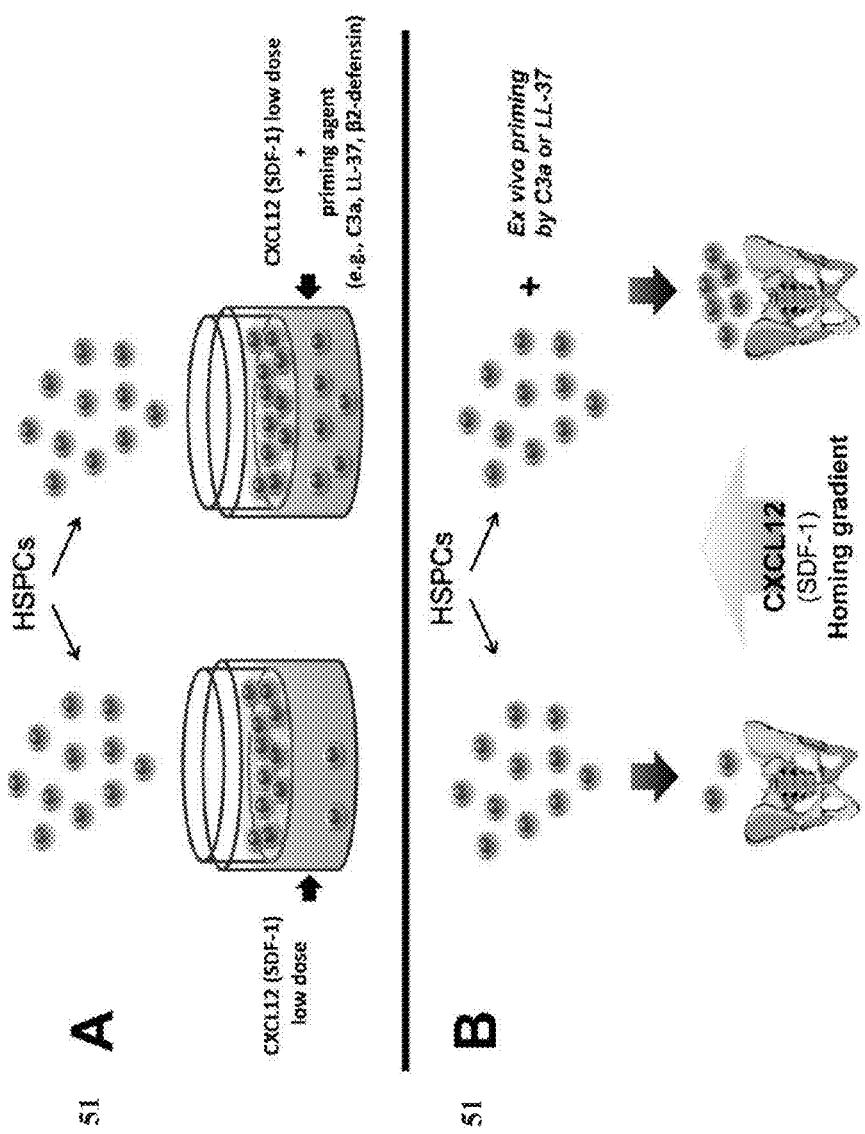

FIG. 51A-B—A priming effect increases the responsiveness of HSPCs to shallow CXCL12 gradients. The overall scheme of chemotactic assays performed in the transwell system to evaluate the HSPC priming phenomenon (Panel A). In the presence of a priming agent (e.g., cationic antimicrobial peptides [CAMPs] such as C3a, cathelicidin [LL-37], or β2-defensin), HSPCs may respond more robustly to low doses of CXCL12. This phenomenon was tested by this faculty group in the clinic, where UCB is exposed ex vivo to a priming agent (e.g., C3a) before transplantation in order to respond more robustly to CXCL12 homing gradient (Panel B—thick arrow).

Figure 52:
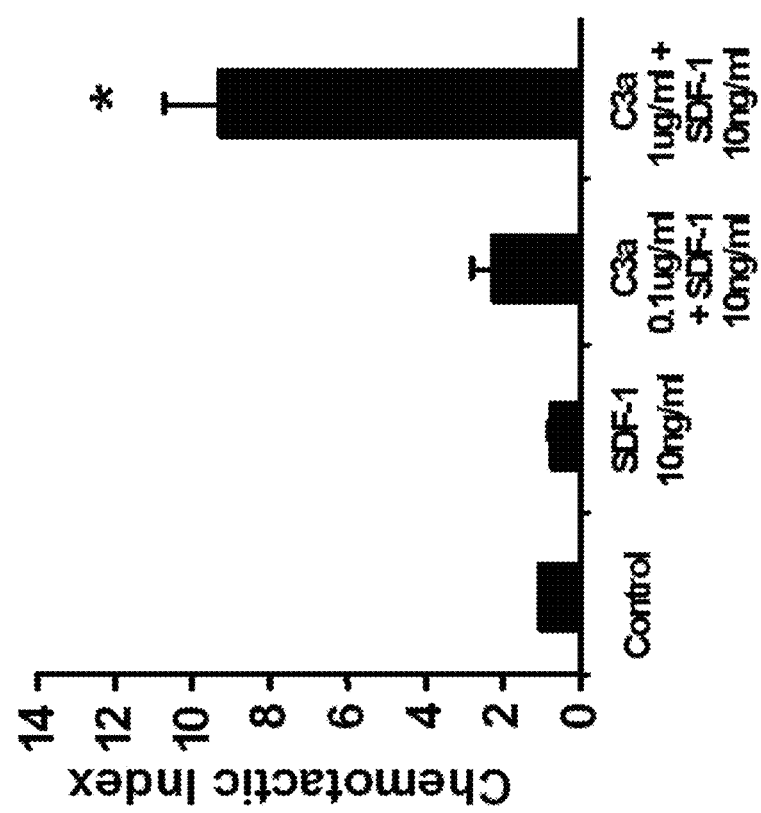

FIG. 52—In Vitro Migration Assay UCB. UCB MNC are loaded in the top chamber and the number of $CD34^+$ HSC present after the 3 h chemotaxis assay in the lower chambers from trans-wells are enumerated by FACS. Co-culture of human UCB MNC with C3a at concentration 1 ug/ml was associated with significantly higher rates of UCB chemotaxis in vitro.

Figure 53:
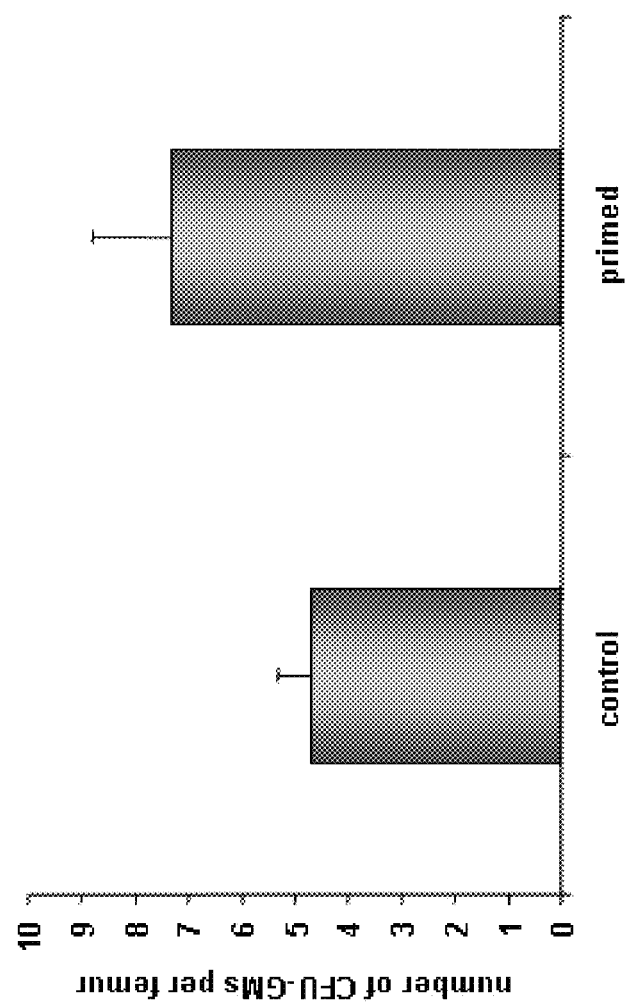

FIG. 53—24 h Homing of C3a primed UCB vs. control in NOG. Further biologic function analyses were performed to determine whether NOG engraftment of UCB CD34 and MNC correlates with migratory responsiveness to SDF-1 gradients measured in vitro. UCB primed with C3a was compared to control unprimed as to number of human CFU-GM per femur measured 24 h after injection of human cells via tail vein.

FIG. 54A-B—NOD.SCID engraftment comparing C3a Primed UCB vs. Control. Co-culture of UCB with C3a was associated with significantly higher human CD45 cells detected by FACS in marrow of NOD.SCID at 8 weeks after injection. 54A—control; 54B—C3a FIG. 55A-B—Multi-parametric analysis of hematopoietic stem and progenitor cells from umbilical cord blood by cytometry. A, Schematic representing a simplified hematopoietic hierarchy. B, Immunophenotyping strategy, using Ficoll-processed UCB sample, for the detection of chemokine receptors expression on the surface of HSPCs sub-population by flow cytometry. HSPC population was first gated out the lineage markers (Lineage⁻: CD2, CD3, CD11b, CD14, CD15, CD16, CD19, CD56, CD123, CD235a) and CD45RA. Phenotypic definitions of HSPC subsets were differentiated based on the expression of $CD133^+$ alone (the most immature), $CD133^+CD34^+$ and $CD34^+$ alone. HSPCs were further analyzed for the expression of HLA-DR or CD49f. Cytometry analysis of surface expression of chemokine receptors are displayed as histogram plots.

Figure 56:
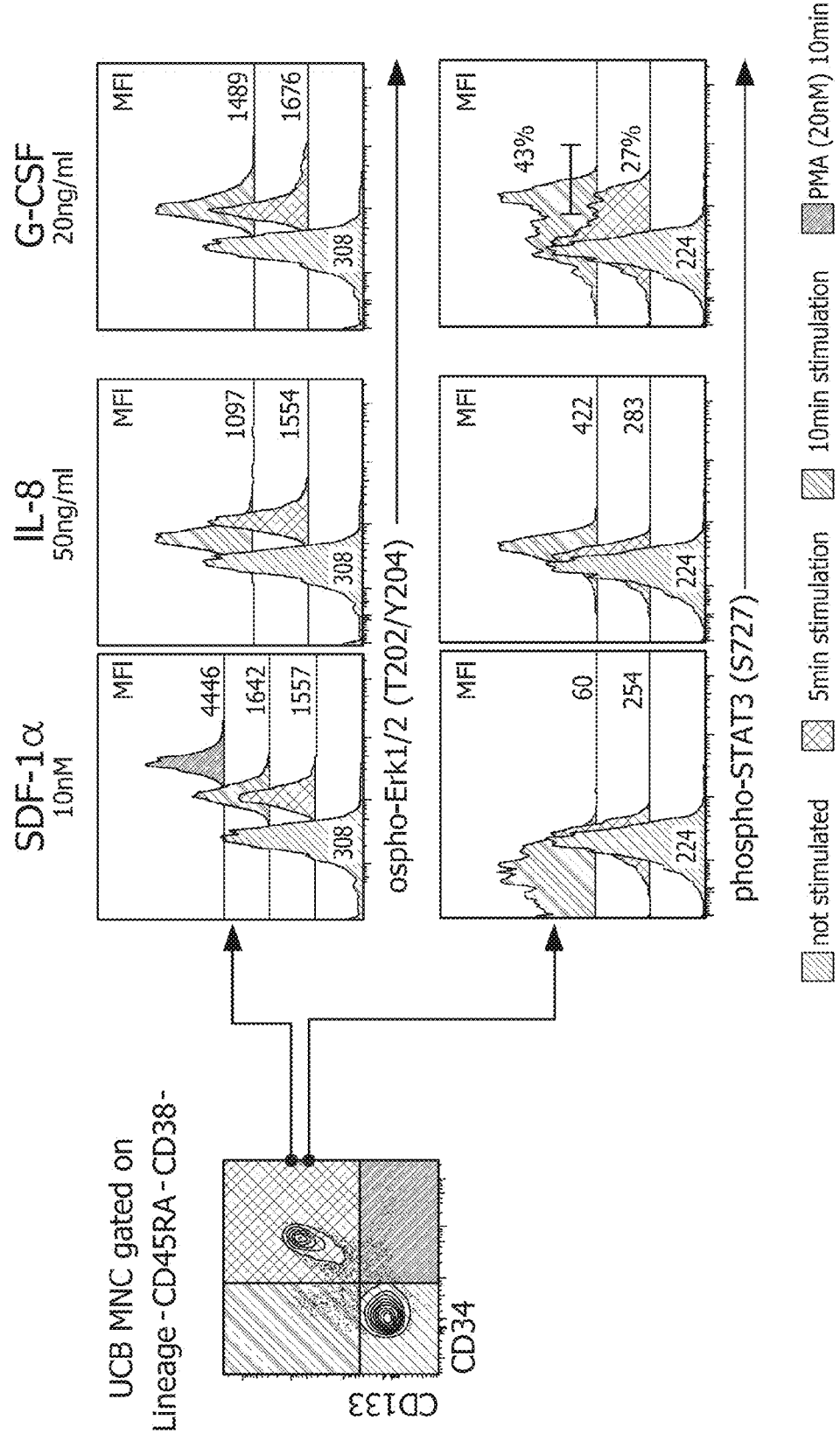

FIG. 56—Phospho-signaling analysis of human UCB-HSPC reveals biochemical heterogeneity of HSC compartment. Schematic illustration of detection of intracellular phospho-signaling events in multiple HSPC populations by cytometry. HSPCs were purified using lineage separation beads (Miltenyi). UCB progenitors were stimulated for 10 minutes with SDF-1α, IL-8, G-CSF, or PMA, fixed, and then permeabilized to allow for phospho-Erk1/2 or phospho-STAT3 staining Cells were then stained for surface markers that identify hematopoietic subsets. Flow cytometry analysis of phospho-Erk1/2 (T202/Y204) and Stat3 (pY705) levels of $CD34^+CD133^+$ were performed on BD LSRII/Fortessa.

DETAILED DESCRIPTION

Abbreviations and Acronyms

ABP—adult blood plasma
β2D—β2-defensin
C3aR—C3a-receptor
CAMPs—cationic antimicrobial peptides
CBP—cord blood plasma
CFU—colony forming unit
ChIP—chromatin immunoprecipitation
CI—confidence interval
CPDA—citrate phosphate dextrose anticoagulant
fMLP—N-Formyl-L-methionyl-L-leucyl-L-phenylalanine
FN—fibronectin
FG—fibrinogen
GVHD—graft vs. host disease
HS—hyaluronic acid
hsa—*Homo sapiens*
HSC—Hematopoietic stem cell
HSPC—hematopoietic stem progenitor cells
LF—lactoferrin
LL37—active fragment of cathelicidin
MβCD—methyl-β-cyclodextran
MMP—matrix metalloproteinase
MNC—mononuclear cell
MPP—multipotent progenitors
PB—peripheral blood
PBMC—peripheral blood mononuclear cell
PMV—platelet microvesicle
SDF-1—stromal cell-derived factor-1
SLP—supernatant from leukophoresis product
STHSC—short term HSC
TNC—total nucleated cells
TRM—transplant-related mortality
UCB—umbilical cord blood
UCBT—UBC transplant

DEFINITIONS

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agent" is meant to include something being contacted with a cell population to elicit an effect, such as a drug, a protein, a peptide. An "additional therapeutic agent" refers to a drug or other compound used to treat an illness and can include, for example, an antibiotic or a chemotherapeutic agent.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

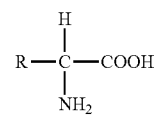

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring or synthetically made) in large numbers but of course they need not be limited to these.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, skin, hair, tissue, blood, plasma, cells, sweat and urine.

The term "cancer", as used herein, is defined as proliferation of cells whose unique trait—loss of normal controls—results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer.

As used herein, the term "carrier molecule" refers to any molecule that is chemically conjugated to the antigen of interest that enables an immune response resulting in antibodies specific to the native antigen.

The term "cell surface protein" means a protein found where at least part of the protein is exposed at the outer aspect of the cell membrane. Examples include growth factor receptors.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

Complement C3a is a 77 amino acid residue protein, derived from the human complement C3a precursor (GenBank Accession No. NP_000055.2). C3a des-arg is the fragment of C3a where the end arginine residue is cleaved.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

As used herein, the term "conservative amino acid substitution" is defined herein as an amino acid exchange within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

By the term "immunizing a subject against an antigen" is meant administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of the antigen.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

As used herein, the term "induction of apoptosis" means a process by which a cell is affected in such a way that it begins the process of programmed cell death, which is characterized by the fragmentation of the cell into membrane-bound particles that are subsequently eliminated by the process of phagocytosis.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

The term "population of cells" as used herein refers to a mixed population such as blood, bone marrow-derived, or umbilical cord blood cells. By the term "at least two different populations of cells" is meant the original sources are different, such as obtaining two or more different lots/units of umbilical cord blood, or umbilical cord blood from a source combined with bone marrow-derived cells from another source, etc. In some instances, the "population of cells" can be subjected to methods for enriching a cell type, such as CD133 or CD34 cells. Of course, if methods are found to obtain pure populations of CD133 or CD34 cells, these cells are encompassed by the methods of the invention as well.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. In particular, purified sperm cell DNA refers to DNA that does not produce significant detectable levels of non-sperm cell DNA upon PCR amplification of the purified sperm cell DNA and subsequent analysis of that amplified DNA. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, D.C., p. 574).

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M NaPO$_4$, 1 mM EDTA at 50° C. with washing in 2× standard saline citrate (SSC), 0.1% SDS at 50° C.; preferably in 7% (SDS), 0.5 M NaPO$_4$, 1 mM EDTA at 50° C. with washing in 1×SSC, 0.1% SDS at 50° C.; preferably 7% SDS, 0.5 M NaPO$_4$, 1 mM EDTA at 50° C. with washing in 0.5×SSC, 0.1% SDS at 50° C.; and more preferably in 7% SDS, 0.5 M NaPO$_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215: 3:403-10; Altschul et al., 1997 Nucleic Acids Res. 25:3389-3402). The default settings provided with these programs are suitable for determining substantial similarity of nucleic acid sequences for purposes of the present invention.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

By the term "vaccine," as used herein, is meant a composition which when inoculated into a subject has the effect of stimulating an immune response in the subject, which serves to fully or partially protect the subject against a condition, disease or its symptoms. In one aspect, the condition is conception. The term vaccine encompasses prophylactic as well as therapeutic vaccines. A combination vaccine is one which combines two or more vaccines, or two or more compounds or agents.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

The methods of the invention involve, in one aspect, administration of umbilical cord blood cells to subjects. Umbilical cord blood cells are cells harvested from the veins and arteries of an umbilical cord. Methods for extracting such cells from umbilical cords are known in the art and have been published (See for example US Published Application No. 20060275271). These cells may be harvested and frozen prior to use or they may be used without freezing. Methods for freezing such cells are also known in the art and have been published (See for example US Published Application No. 20060275271).

As used herein, an isolated cell population is a cell population that has been physically separated from the environment and/or the context in which it naturally occurs or exists. Thus, once the umbilical cord blood cells are removed from the umbilical cord, they are considered isolated.

In important embodiments of the invention, the umbilical cord blood cells are fractionated in order to generate enriched cell populations. As used herein, an enriched cell population is a cell population that has been manipulated in order to increase the frequency of a particular cell type in the population relative to the frequency of that cell type prior to manipulation.

It is to be understood that the cell type being enriched is one that existed in the population prior to manipulation, and that enrichment results from the removal of other cell types from the population rather than addition of the cell type of interest. Of particular interest according to the invention are cell populations enriched in CD34+, CD133+, or CD34+/CD133+ cells. CD34 and CD133 are cell surface protein (or markers) that have been identified previously as present on hematopoietic progenitor cells (including on hematopoietic stem cells). As used herein, a CD34+ cell is a cell that expresses CD34 on its cell surface. Similarly, a CD133+ cells is a cell that expresses CD133 on its cell surface. A CD34+/CD133+ cell is a cell that expresses both CD34 and CD133 on its surface.

Methods for preparing cell populations enriched in particular cell types are known in the art. In the case of cell populations that are defined by a cell surface marker (such as CD34+, CD133+, and CD34+/CD133+ cells), these methods generally use antibodies that are specific for the expressed marker(s). These antibodies can be attached to a number of solid supports including plates (e.g., in panning methods), column matrices (e.g., in column enrichment methods), magnetic beads (e.g., in magnetic separation methods), and the like. These supports are then contacted with the cell population of interest and cells expressing the marker of interest are allowed to bind to the antibody, while the remaining unbound cells are removed. The bound cells are then removed by any number of techniques (e.g., enzymatic, mechanical, competitive binding, temperature, etc.). Enriched populations can also be produced by contacting cells with the antibody of interest and then sorting cells based on the presence or absence of the antibody using fluorescence activated cell sorting. The presence of the antibody is generally observed by labeling the antibody with a fluorescent probe (e.g., FITC) or by contacting the cells with a second antibody that recognizes the first antibody and is itself labeled with a fluorescent probe. These methods, as well as others, are known in the art and those of ordinary skill will be able to readily enrich the desired populations.

Anti-CD34 antibodies include but are not limited to QBend10, 563, HPCA-2, 581, AC136, and Birma K3. Anti-CD133 antibodies include but are not limited to ANC9C5. These antibodies are commercially available from sources such as R&D Systems, Santa Cruz Biotechnology.

The isolated enriched populations can be administered to subjects in amounts (or numbers) effective to treat the patient, as described herein. The numbers of cells necessary for treatment will depend on a number of factors including the severity of the symptoms experienced by the subject (as may be deduced from for example an NIHSS score), the size (or area) of the infarct as determined using a medical imaging technique such as MRI, the degree of enrichment of the desired cell type in the administered population, the age and/or weight of the patient, and the like. In one embodiment, cell numbers in the range of about 1 to $10 \times 10^6$ or about 2 to $8 \times 10^6$ can be administered to the subject. Thus depending on the particular patient and the population being administered, the number of cells administered can be about $2 \times 10^6$, about $3 \times 10^6$, about $3 \times 10^6$, about $5 \times 10^6$, about $6 \times 10^6$, about $7 \times 10^6$, about $8 \times 10^6$, about $10 \times 10^6$, about $20 \times 10^6$, about $50 \times 10^6$, or about $100 \times 10^6$. These amounts may refer to the total number of CD34+, CD133+ or CD34+/CD133+ cells, or the total mononuclear cells administered to the subject, depending on the embodiment and the degree of enrichment in the cells.

In another embodiment, the number of cells can be injected base on weight (kg) of the subject. In one embodiment, cell numbers in the range of about 1 to $10 \times 10^6$/kg or about 2 to $8 \times 10^6$/kg can be administered to the subject. Thus depending on the particular patient and the population being administered, the number of cells administered can be about $2 \times 10^6$/kg, about $3 \times 10$/kg$^6$, about $3 \times 10^6$/kg, about $5 \times 10^6$/kg, about $6 \times 10^6$/kg, about $7 \times 10^6$/kg, about $8 \times 10^6$/kg about $1 \times 10^7$/kg, about $5 \times 10^7$/kg. These amounts may refer to the total number of CD34+, CD133+ or CD34+/CD133+ cells, or the total mononuclear cells administered to the subject, depending on the embodiment and the degree of enrichment in the cells, or as described elsewhere herein.

The cells to be administered may be provided in a single cord blood unit although in some instances multiple cord blood units must be combined to achieve the cell numbers being administered. As used herein, a cord blood unit is the amount of cord blood harvested from a single cord.

In one embodiment, an effective amount of at least one growth factor, cytokine, hormone, or extracellular matrix compound or protein is administered as part of the composition or is used to pretreat cells. In one aspect, a combination of these agents is used or they are included in the mixture of the invention. In one aspect, growth factors useful in the practice of the invention include, but are not limited to, EGF, PDGF, GCSF, IL6, IL8, IL10, MCP1, MCP2, Tissue Factor, FGFb, KGF, VEGF, PDGF, MMP1, MMP9, TIMP1, TIMP2, TGFβ, interferons, and HGF. One of ordinary skill in the art will appreciate that the choice of growth factor, cytokine, hormone, or extracellular matrix protein used will vary depending on criteria such as the age, health, sex, and weight of the subject, etc. In one aspect, the growth factors, cytokines, hormones, and extracellular matrix compounds and proteins are human.

The present invention encompasses the use of fragments of human Complement C3a precursor (NCBI Reference Sequence: NP_000055.2; 1663 aa), as well as homologs and fragment thereof. In particular, the methods encompass use of the fragments C3a (SEQ ID NO:1; 77 amino acid residues) and desArgC3a (SEQ ID NO:2; 76 amino acid residues), and active homologs, fragments, and derivatives thereof. These fragments (peptides) can be obtained different ways. They can, for example, be purchased commercially, isolated and purified, or synthesized. Homologs and fragments of C3a and desArgC3a can be prepared as well, as described herein or using techniques known in the art.

The methods of the invention further encompass the use of at least one microRNA ("miRNA") to prime cells before administration to a subject in need thereof. In one aspect, a useful miRNA is miR-184 (SEQ ID NO:3).

Useful sequences of the invention include, for example:

```
                                          SEQ ID NO: 1-
Human Complement C3a anaphylatoxin
(77 residues)
SVQLTEKRMDKVGKYPKELRKCCEDGMRENPMRFSCQRRTRFISLGEACK

KVFLDCCNYITELRRQHARASHLGLAR

SEQ ID NO: 2-
Human C3a des-arg (76 residues)
SVQLTEKRMDKVGKYPKELRKCCEDGMRENPMRFSCQRRTRFISLGEACK

KVFLDCCNYITELRRQHARASHLGLA

SEQ ID NO: 3-
human MiR-184
uggacggagaacugauaagggu
```

Note that the only difference between C3a and desArgC3a is that the last arginine residue is deleted from C3a to form desArgC3a.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters. Examples of solid phase peptide synthesis methods include the BOC method which utilized tertbutyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation," a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones, or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for homologs of proteins and peptides. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on protein function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Homologs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein or peptide obtained as described herein may be purified by following known procedures for protein purification, wherein an immunological, enzymatic, or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

Amino Acid Substitutions

In certain embodiments, the disclosed methods and compositions may involve preparing peptides with one or more substituted amino acid residues. In various embodiments, the structural, physical and/or therapeutic characteristics of peptide sequences may be optimized by replacing one or more amino acid residues.

In one embodiment, the invention encompasses the substitution of a serine or an alanine residue for a cysteine residue in a peptide of the invention. Support for this includes what is known in the art. For example, see the following citation for justification of such a serine or alanine substitution: Kittlesen et al., 1998 Human melanoma patients recognize an HLA-A1-restricted CTL epitope from tyrosinase containing two cysteine residues: implications for tumor vaccine development J Immunol., 60, 2099-2106.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of Alkyl-Substituted Hydrophobic Amino Acids:

including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of Aromatic-Substituted Hydrophobic Amino Acids:

including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine Substitution of Amino Acids Containing Basic Functions:

including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of Acidic Amino Acids:

including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of Side Chain Amide Residues:

including asparagine, glutamine, and alkyl or aromatic substituted derivatives of asparagine or glutamine.

Substitution of Hydroxyl Containing Amino Acids:

including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; miRNA, siRNA, and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

miRNAs are RNA molecules of about 22 nucleotides or less in length. These molecules are post-transcriptional regulators that bind to complementary sequences on target mRNAs. Although miRNA molecules are generally found to be stable when associated with blood serum and its components after EDTA treatment, introduction of locked nucleic acids (LNAs) to the miRNAs via PCR further increases stability of the miRNAs. LNAs are a class of nucleic acid analogues in which the ribose ring is "locked" by a methylene bridge connecting the 2'-O atom and the 4'-C atom of the ribose ring, which increases the molecule's affinity for other molecules.

In one embodiment, an anti-miRNA oligomer directed against miR-184 can be used. See U.S. patent application Ser. No. 13/503,189, WO2007/112754, and WO2007/112653 for additional descriptions of oligomers, locked nucleic acid oligomers, gapmers, mixmers, totalmers, etc. In one aspect, an anti-miR-184 can be purchased.

The invention is also directed to methods of administering the compounds, cells, proteins and peptides (collectively referred to as compounds) of the invention to a subject.

Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

The present invention is also directed to pharmaceutical compositions comprising the peptides of the present invention. More particularly, such compounds can be formulated as pharmaceutical compositions using standard pharmaceutically acceptable carriers, fillers, solubilizing agents and stabilizers known to those skilled in the art.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day. Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

Compounds which are identified using any of the methods described herein may be formulated and administered to a subject for treatment of the diseases disclosed herein.

The invention encompasses the preparation and use of pharmaceutical compositions comprising a compound useful for treatment of the conditions, disorders, and diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively).

Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent.

Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Without further description, it is believed that one of ordinary skill in the art can, using the preceding description and the following illustrative examples, make and utilize the compounds of the present invention and practice the claimed methods. The following examples therefore, specifically point out the preferred embodiments of the present invention, and are not to be construed as limiting in any way the remainder of the disclosure.

EXAMPLES

Example 1

Figure 1:
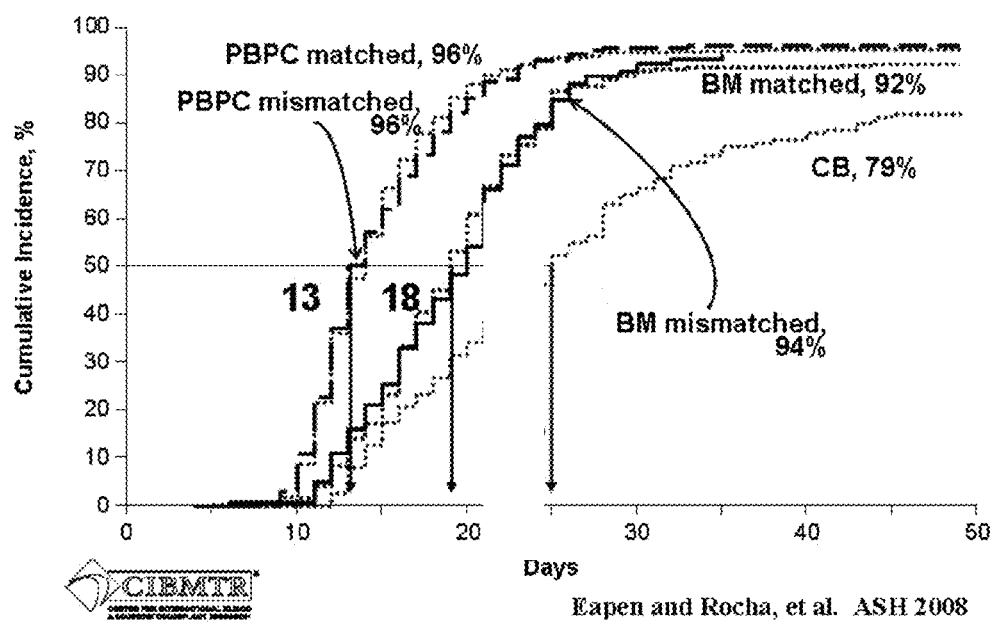
FIG. 1—Delayed neutrophil recovery and suboptimal engraftment are major barriers to the successful use of UCB in adults and children.
Figure 2:
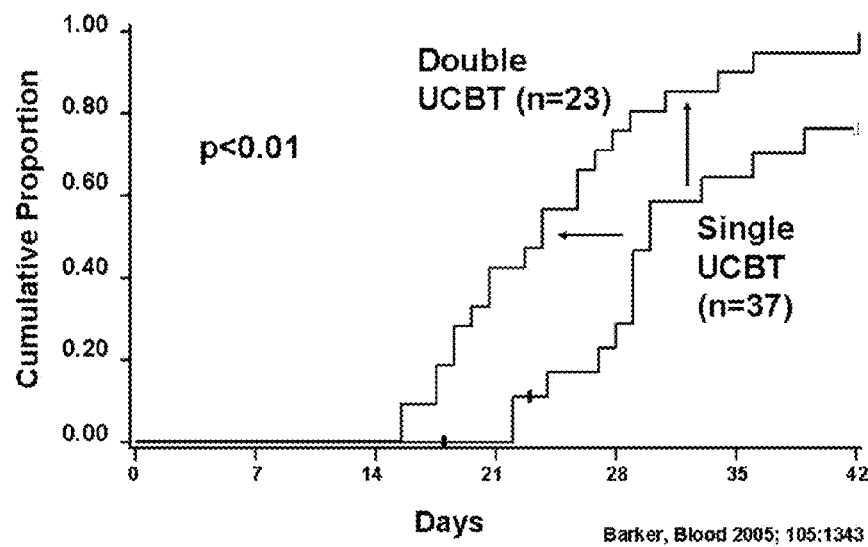
FIG. 2—Improvement on Engraftment after Myeloablation with Double Umbilical Cord Transplantation.

Engraftment after Double UCBT. It was hypothesized that the simple co-infusion of two UCB units would approximately double the number of CD34+ cells (presuming the two units were approximately equivalent in cell number). If engraftment was based on the combined CD34 cell dose, then engraftment would increase and the incidence curve would move to the left demonstrating more rapid recovery (see Example 1, FIG. 1). As shown in Example 1, FIG. 2, the result of the initial phase I study proved safety of the double UCBT platform and suggested that there was an additive effect. In the 23 patients with high-risk hematologic malignancy (age range, 13-53 years) that received 2 UCB units (median infused dose, $3.5 \times 10^7$ total nucleated cells [TNC]/kg; range [r], $1.1$-$6.3 \times 10^7$/kg) neutrophil recovery occurred at a median of 23 days (r, 15-41 days) which was significantly shorter than a similar cohort of patients who had received single UCB units grafts (65% incidence of engraftment at a median of 32 days). The study also demonstrated that both units could contribute to hematopoiesis early on. At day 21, chimerism was derived from both donors in 24% of patients. By day 100, a single unit predominated in all patients.

More recently we updated our experience with this platform in 105 consecutive patients with malignant disease transplanted with two partially HLA matched UCB units.

Engraftment.

Figure 3:
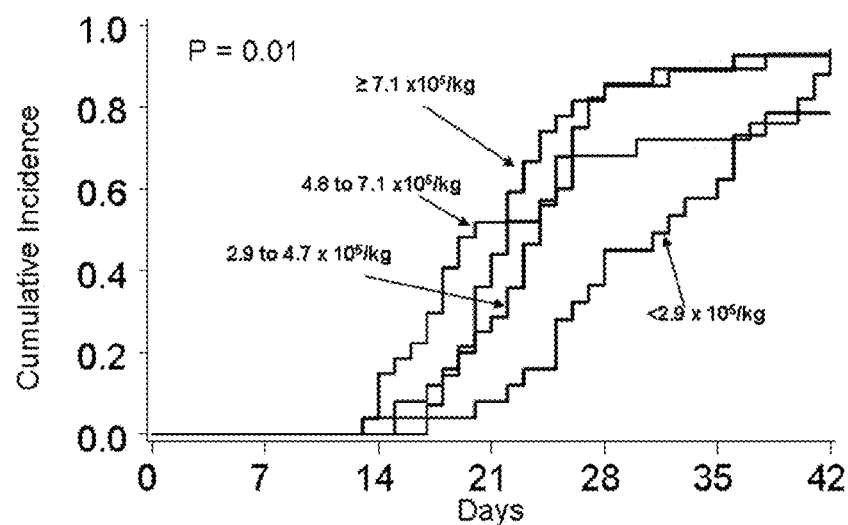
FIG. 3—Impact of CD34+ Cell Dose (in quartiles on Engraftment after Myeloablative Double UCBT.

The incidence of sustained donor engraftment was 89% (95% confidence interval [CI], 82-95) at a median of 23 days (r, 13-42). In logistic regression, patients who received the combined CD34+ cell dose that was $>2.9 \times 10^5$/kg had a higher probability of engraftment (OR 3.18, CI: 1.38-7.29) (FIG. 3). By day 180, the incidence of platelet recovery $\geq 50 \times 10^9$/L was 64% (CI: 52-76%). These data confirm the safety of double UCB transplantation in terms of engraftment and refute the null hypothesis that engraftment would be jeopardized by the bi-directional immune rejection between the two units. Notably, 76% of recipients had persistence of only one UCB unit by day 21. While the remaining 24% had engraftment of both units at day 21, the predominating unit always predominated long term. To date, <5% of patients have 'double chimerism' after day 100.

The next question was whether any factor could be identified that could predict the winning unit. We evaluated cell doses, % viability, order of infusion, ABO match, sex match, KIR match, and HLA match—no factor has yet been shown to predict which unit will predominate either in recipients of myeloablative or non myeloablative regimens. The best matched unit 'wins' 46% of the time and the unit with the highest CD34 cell dose 'wins' 50% of the time.

Other Outcomes. GVHD.

Incidences of grade II-IV and III-IV acute GVHD were 51% (CI: 41-62%) and 19% (CI: 11-26%), respectively. The incidence of chronic GVHD was 26% (CI: 17-35%), and no factor were associated with a greater risk. Six month and two years TRM was 26% (CI: 18-35%) and 32% (95% CI: 22-41%).

Relapse and Disease-Free Survival (DFS).

With a median follow-up of 2 years (r, 1.0-6.5), the cumulative incidence of relapse at 3 yrs was 19% (CI: 11-27%). The overall probability of DFS at 3 yrs was 51% (CI: 40-60%).

Summary.

These results indicate that the co-infusion of two partially HLA matched UCB units is safe and efficacious, as measured by high incidence of engraftment. Like the single UCB transplant setting, patients that received higher cell doses have faster and more complete engraftment. However, time to neutrophil recovery remains slow, substantially slower than in patients transplanted with mobilized peripheral blood. The goal is to ultimately identify a strategy that retains the benefits of UCB (namely, less HLA restriction, low incidence of GVHD, and robust GVL effect) and yet have hematopoietic recovery rates comparable to mobilized peripheral blood (median day 13).

Complement Pathway and Homing and Engraftment

Complement 3a Fragment Priming

We have shown that both C3a and its derivate $C3a_{des-Arg}$ potentiate (prime) chemotaxis of human $CD34^+$ cells to low-threshold doses of SDF-1. However, on their own, neither C3 cleavage fragments chemoattract $CD34^+$ cells. Exposure of UCB $CD34^+$ cells to a low dose of SDF-1 promotes actin polymerization which is enhanced by the presence of C3a.

CXCR4 expression, however, is not enhanced after C3a exposure. The expression of CXCR4 on BM or UCB-derived CD34+ cells may vary between 20% to 60%. As only 3% of CD34+ cells are clonogenic progenitors and less than 1% of CD34+ cells are true HSC, this result is not unexpected.

To engraft, HSC must first adhere to the endothelium of BM sinuses in the hematopoietic microenvironment. Next, they must cross the subendothelial basement membrane, a process in which matrix metalloproteinases (MMP) are crucial. Lastly, they must occupy the hematopoietic niche and proliferate.

In vitro studies have shown that C3a increases adhesion of UCB $CD34^+$ cells to human umbilical vein endothelial cells. However, the combination of C3a priming and SDF-1 led only to a slight increase in the adhesion of $CD34^+$ cells.

Priming UCB and BM CD34+ cells with C3a has been shown to significantly increase MMP-9 and MMP-2 secretion and trans-Matrigel migration which mimics cell crossing of the subendothelial membrane toward a low dose of SDF-1. Importantly, murine BM-derived Sca-1+, human BM- and UCB-derived CD34+ cells primed with C3a before transplantation into lethally irradiated mice were shown to home more efficiently as compared to unprimed cells as measured by frequency of CFU-GM and CFU-S from the primary recipients and CFU-S from the spleens of secondary recipients.

Figure 4:
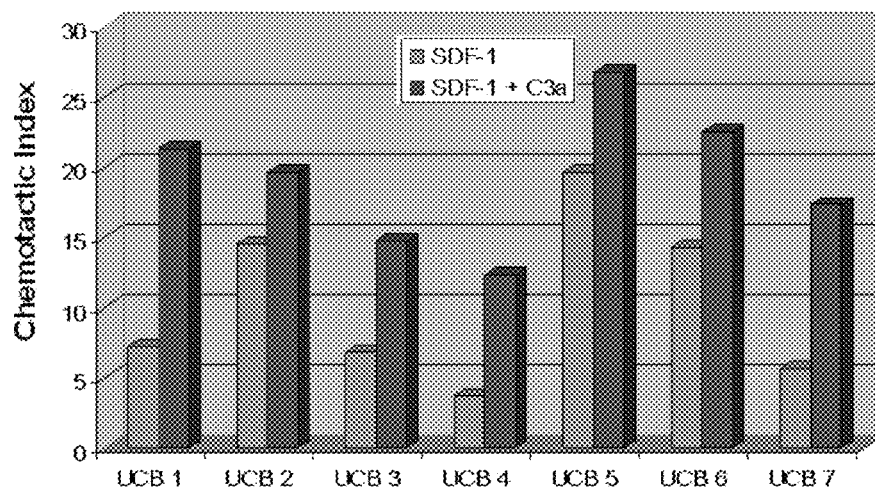
FIG. 4—Transwell Migration of C3a Primed Bone Marrow Mononuclear Cells.
Figure 5A:
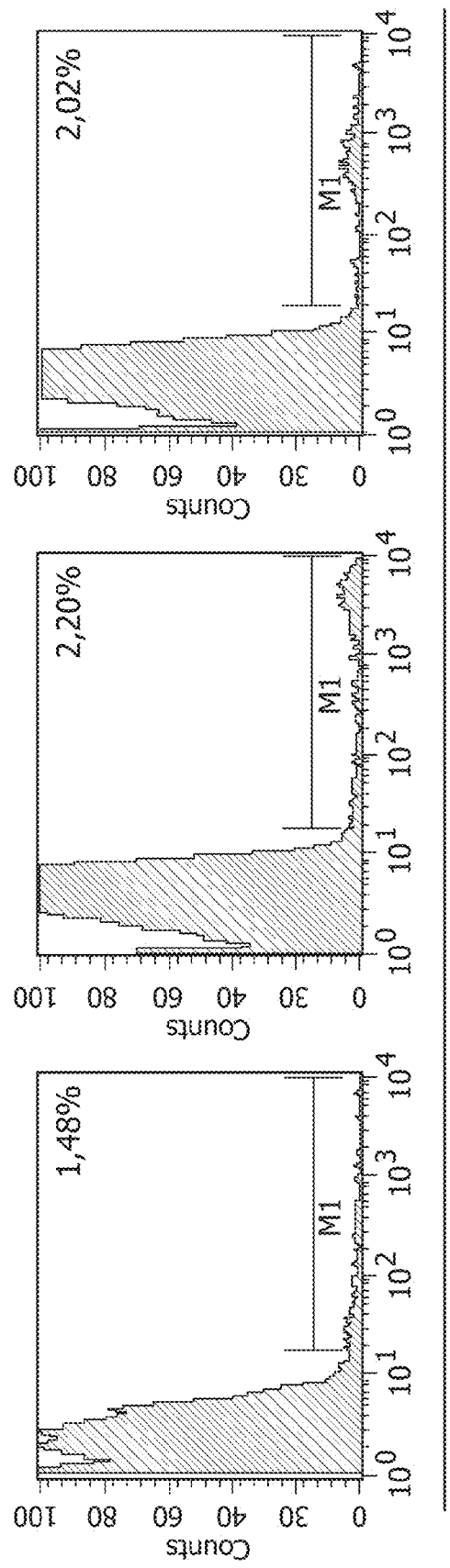
FIG. 5A-B—Long-Term Engraftment of C3a Primed Progenitors (comprising upper and lower panels).
Figure 5B:
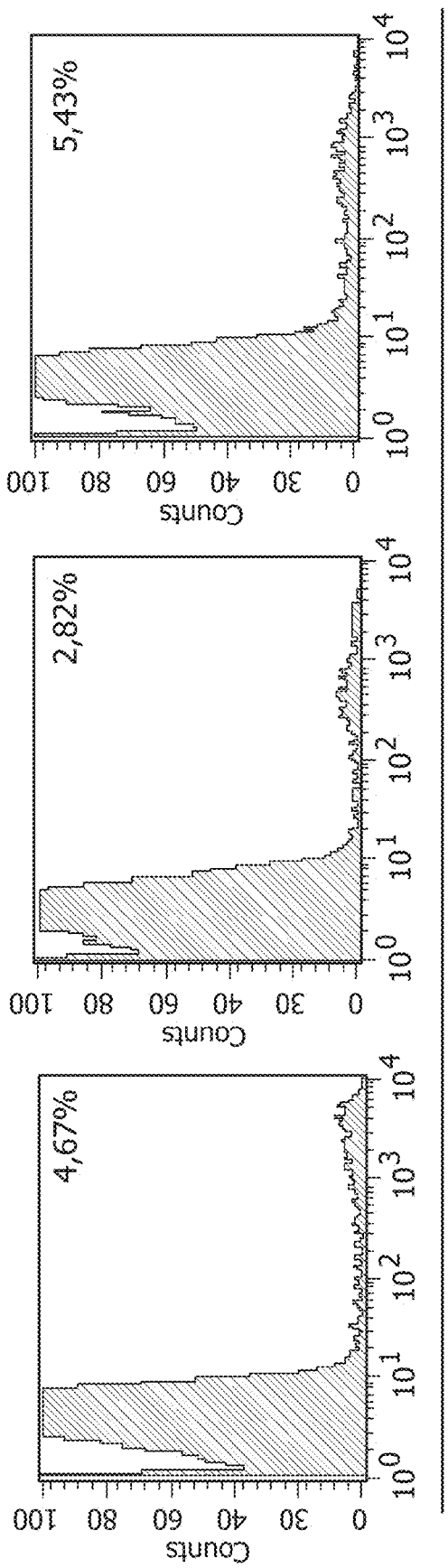

In vitro and in vivo data indicates that priming of UCB-derived CD34+ hematopoietic stem cells (HSC) by short-term (15-30 min) exposure to C3a fragment enhances CXCR4 incorporation into membrane lipid rafts. This results in a better interaction of CXCR4 with the proteins responsible for signal transduction that are located downstream of this receptor. C3a primed UCB CD34+ HSC exhibit enhanced SDF-1-mediated transwell cell migration (FIG. 4), enhanced marrow homing as measured by the number of CFU-GM harvested per femur 24 h after injection of NOD/SCID mice. As compared to unprimed cells, C3a primed progenitors exhibit long-term human engraftment as measure by flow cytometry for human anti-CD45 in NOD/SCID mice harvest after 12 weeks (FIG. 5A-B). Moreover, mice that receive C3a primed hematopoietic progenitors had a 5 day faster rate of leukocyte recovery relative to untreated mice with a benefit in platelet counts as well (FIG. 6A-B). In the murine studies, neither infusional toxicity nor evidence of coagulopathy was observed.

The dose of C3a fragment has been optimized in these studies to maximize chemotactic response of CD34+ cells to low/suboptimal dose of SDF-1. This dose (1 ug/ml) corresponds to activation of 1% of the C3 that circulates in biological fluids at the concentration 1.2 mg/ml. C3a fragment is fully internalized with no residual complement protein measured by ELISA in supernatant of UCB CD34+ HSC and progenitors after short-term priming.

Since the complement system is highly conserved during evolution, the biological effects of complement in murine model not surprisingly closely mimic those observed in humans. For both murine and human HSC and progenitors we have observed i) a positive C3a mediated priming effect on responsiveness to suboptimal doses of SDF-1, and ii) C3a induced incorporation of CXCR4 into membrane lipid rafts. In addition, it appears that the optimal dose of C3a is similar for both murine and human HSC and progenitors.

cGMP Grade Validation Runs.

The first validation runs have been performed. Studies sponsored by the NHLBI's Production Assistance for Cellular Therapies (PACT) program have demonstrated high recovery of CD34+ cells and CFU-GM without effect on cell viability or sterility. For these studies, an UCB unit was thawed using the standard clinical method and divided in 2 aliquots for C3a priming and a control.

Figure 7:
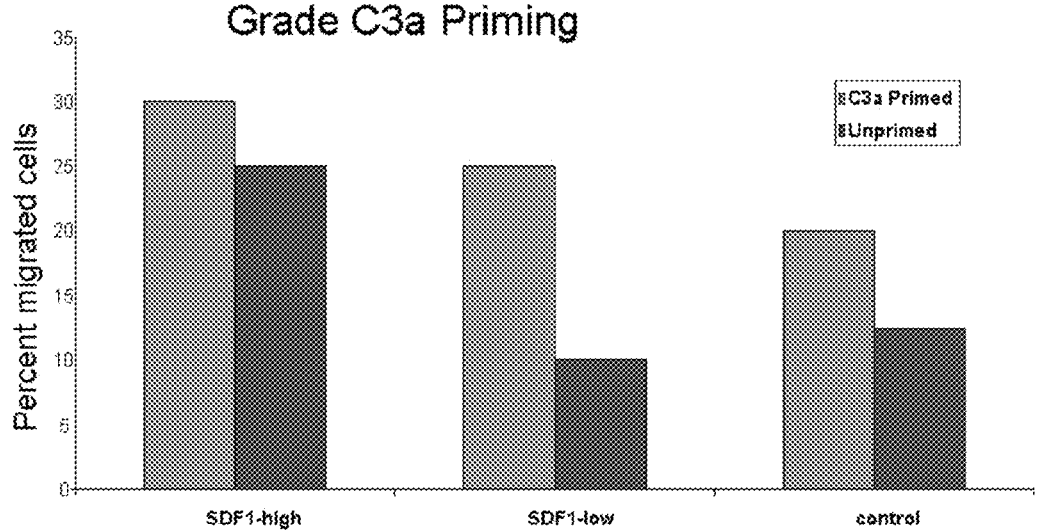
FIG. 7—SDF-1 Mediated Migration after GMP Grade C3a Priming.

In summary, the validation run passed lot release (gram stain negative, sterility, endotoxin free, viability >70%) with >90% recovery of CD34 count and CFU-GM and responsiveness in the SDF-1 migration assay. In the SDF-1-mediated migration assay (FIG. 7) the study cell population are the cells exposed to low concentration of SDF-1 (middle bars); unprimed cells were the negative control (right bars) whereas those exposed to high concentration (left bars) of SDF-1 were the positive control. Importantly, there was no detectable residual C3a in the supernatant after 30 minutes incubation by ELISA assay.

Complement 5a and Cationic Peptides Priming.

Figure 8A:
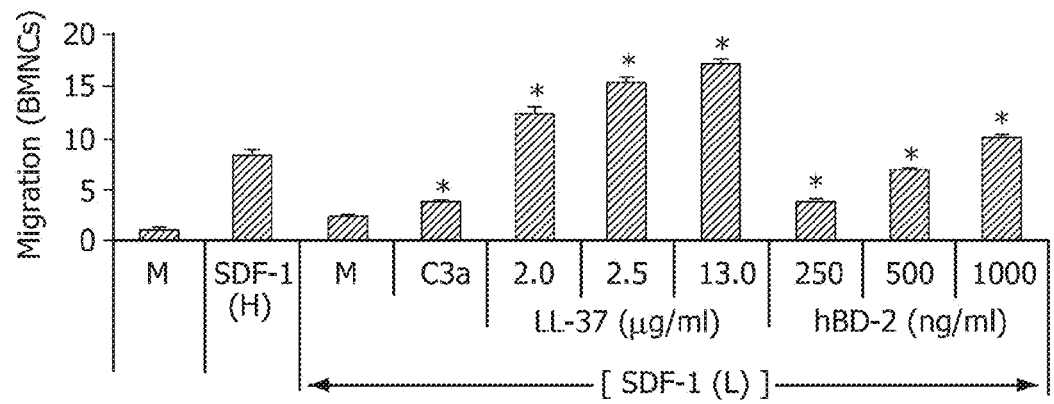
FIG. 8A-B—A) BM mononuclear cell and B) CFU-GM migration in response to an SDF-1 gradient after priming with LL-37 or hBD-2. Values are fold increases of migrated cells compared to media alone.
Figure 8B:
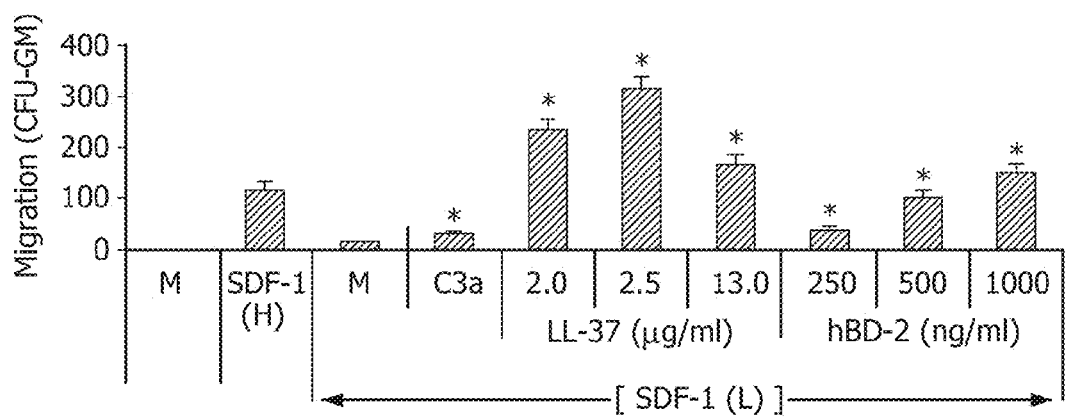

We also evaluated the effect of complement fragment 5a (C5a). We found that C5a receptor (C5aR) was not expressed on the surface of HSC and progenitors, and that a C5a-mediated promobilization effect was mediated by stimulated granulocytes. After leaving the BM, granulocytes undergo degranulation in response to plasma C5a and secrete cationic peptides, such as cathelicidin (LL-37) and β-defensin-2 (hBD-2). In the original studies, it was demonstrated that recombinant LL-37 and hBD-2 highly enhanced the responsiveness of hematopoietic progenitors to plasma SDF-1 (FIG. 8A-B). However, this phenomenon was not receptor-dependent, as agonists of membrane receptors that may bind beta2-defensin (FPRL-1), cathelicidin (CCR6)—FPRL-1 agonist, and MIP-3alpha did not show similar priming effects. It was hypothesized that this response may be affected by the distribution of membrane lipids by cationic peptides. To support this hypothesis, an inhibitor of cell membrane raft formation (methyl-β-cyclodextrin) was shown to inhibit the priming effects of both compounds, indicating this effect is dependent on CXCR4 incorporation into lipid rafts. Direct confocal analysis of CXCR4 and lipid raft colocalization in the presence or absence of cationic peptides confirmed these findings.

Leukophoresis products enriched in activated granulocytes release hBD-2 and LL-37. The question was whether this might explain why mobilized peripheral blood hematopoietic progenitors engrafts substantially faster relative to marrow. We therefore performed studies in a murine BM transplant model where syngeneic BM mononuclear cells were exposed ex vivo to LL-37 for 30 minutes and subsequently transplanted into lethally irradiated recipients. Interestingly, mice transplanted with BM primed by these cationic peptides showed accelerated recovery of platelets and neutrophils by ~3-5 days compared to unprimed control cells. These data suggest that small cationic peptides, which primarily possess antimicrobial functions and are harmless to mammalian cells, could be clinically applied to prime human HSC and progenitor populations as a strategy to enhance rate of hematopoietic recovery. On the basis of these findings, this represents a second strategy for reducing the period of neutropenia in recipients of UCB Summary.

Preclinical studies detailed here suggest that C3a and LL-37 are potentially clinically relevant approaches to enhance the homing of human UCB HSC and progenitors via the SDF-1/CXCR4 mediated pathway.

Example 2

The number of UCB HSPCs contained in a single unit for transplantation is limited. Our preliminary data show that UCB vary in chemotactic responsiveness to SDF-1 gradient. The data presented below supports our new hypothesis that priming the CXCR4-SDF-1 axis could improve HSPC homing and thus accelerate allogeneic engraftment of UCB.

In Vitro Chemotactic Responsiveness of UCB HSPCs Varies with the Donor.

An increased migration of UCB-derived CD34+ cells, as compared to BM and mPB CD34+ cells was reported in transwell migration assays was previously reported. However, we noticed large inter-individual differences in the in vitro migratory ability of UCB CD34+ cells, ranging from 1.1% to 14.3% for spontaneous migration and 3.1% to 62.3% for SDF-1-induced (300 ng/mL) migration. The lower migratory capacity in vitro of UCB-derived CD34+ cells was not due to lower expression of CXCR4, but likely reflects the decreased migratory behavior of these cells. More importantly, by exposing/priming UCB-derived CD34+ cells with C3a or $_{desArg}$C3a, we were able to significantly increase the responsiveness of UCB cells to SDF-1 gradient, in particular in those cases when responsiveness to SDF-1 was relatively low. Based on this, we postulate that UCB HSPC responsiveness to an SDF-1 gradient varies with each collected UCB unit and that, in cases when responsiveness is low, UCB HSPCs should be identified and primed before infusion.

Supernatants from Leukophoresis Products (SLP) and their Selected Components (e.g., C3a) Prime/Enhance HSPC Chemotactic Responses to an SDF-1 Gradient.

HSPCs from the mPB engraft faster compared to HSPCs aspirated from BM. To test the hypothesis that mPB-derived HSPCs are primed in their responses to SDF-1 by molecules present in SLP, we pooled together SLP from three patients and exposed BM or UCB CD34+ cells to the SLP during chemotaxis to a low (10 ng/mL) dose of SDF-1. We found that CD34+ cells placed in the upper chambers with SLP loaded either in the upper or lower chambers responded significantly better to the low dose of SDF-1 than CD34+ cells without SLP, reaching ~45% of their maximal chemotactic response achieved with a high (optimal) dose of SDF-1 (300 ng/mL) (Example 2, FIG. 11, panel A). On their own, SLP only slightly chemoattracted CD34+ cells and did not increase chemotaxis of CD34+ cells to a high dose of SDF-1 (Example, FIG. 11, panel A).

Since the population of CD34+ cells is heterogeneous and clonogenic HSPCs account for only about 3-5%, we investigated whether SLP could also prime chemotactic responses of CD34+ clonogenic progenitors to SDF-1. After chemotaxis CD34+ cells were collected from the lower chambers and plated to grow clonogenic myeloid (CFU-GM), erythroid (BFU-E), and megakaryocytic (CFU-Meg) colonies. We found that SLP efficiently increased the chemotactic response of clonogenic CD34+ progenitors and heat inactivation of SLP significantly decreased (by ~50%) the priming effect with respect to a low dose of SDF-1 (not shown). To evaluate whether mPB CD34+ cells remain in a primed status when they are resuspended in SLP, in the next set of experiments, mPB CD34+ cells were maintained in SLP or washed free of SLP and resuspended in fresh leukapheresis buffer. We observed that the priming responses of mPB CD34+ cells as well as CD34+ clonogenic CFU-GM to a threshold dose of SDF-1 decreased to control values after the cells were washed out of the SLP.

Moreover, as SLP contains several components that potentially could prime the responses of CD34+ cells, (Example 2, FIG. 11, panel B) the most important being PMV and activated complement proteins such as anaphylatoxin C3a, soluble VCAM-1, soluble ICAM-1, uPAR, FG, and FN, we evaluated whether these factors could induce the chemotaxis of HSPCs when used alone. We found no evidence that they did (not shown). We also examined whether FG, FN, soluble VCAM-1, soluble ICAM-1, uPAR, and C3a prime HSPCs in their responses to SDF-1. We found that when these molecules were added to the lower chambers together with SDF-1, they increased the chemotactic response of UCB CD34+ cells to SDF-1 (FIG. 3, panel B). To determine whether this also affects UCB CD34+ clonogenic progenitors, UCB CD34+ cells were collected from the lower chambers after the chemotaxis assay and plated in methylcellulose cultures. We found that all of these compounds, like SLP, increased the SDF-1-directed chemotaxis of CFU-GM, BFU-E, and CFU-Meg progenitors. Moreover, a similar effect for the established hematopoietic cell lines Molt 4, Nalm-6, and THP-1 was also found (data not shown).

Both C3a and $_{desArg}$C3a Enhance SDF-1-Dependent Migration of CD34+ Cells.

FIG. 12 supports the effect of C3a demonstrated in FIG. 11 panel B and demonstrates that both C3a and its derivate C3a$_{des-Arg}$ potentiate (prime) chemotaxis of human CD34+ cells to low-threshold doses of SDF-1. However, on their own, neither C3 cleavage fragments chemoattract CD34+ cells. In this study, we will employ C3a to enhance/prime responsiveness of UCB to SDF-1 gradient.

C3a does not Upregulate Expression of CXCR4 but it Induces Actin Polymerization in UCB CD34+ Cells.

In another set of experiments, we attempted to elucidate the molecular mechanisms by which C3a enhances the responsiveness of hematopoietic cells to an SDF-1 gradient. BM or UCB CD34+ cells were cultured in medium supplemented with C3a (1 mg/ml) or control medium (medium alone) and the influence of this incubation on the expression of CXCR4 was evaluated after 0, 12, and 24 hrs using fluorescence activated cell sorting (FACS) analysis, with negative results (not shown). However, we observed that actin polymerization of CD34+ cells to a low dose of SDF-1 was enhanced in the presence of C3a.

Incorporation of CXCR4 into Lipid Rafts is Responsible for the Priming Effect in Normal Human BM CD34+ Cells.

Since it has been demonstrated that optimal signaling from CXCR4 correlates with its presence in lipid rafts, we asked whether the C3a and $_{desArg}$C3a modulate the incorporation of CXCR4 into lipid rafts. As lipid raft formation is perturbed by polyene antibiotics (e.g., Nystatin, Amphotericin B), we first examined whether these compounds inhibit the chemotaxis of CD34+ cells to an SDF-1 gradient (Example 2, FIG. 13, panel A).

We found that both compounds used at doses that are not toxic to the cells significantly inhibited SDF-1-mediated migration of both CD34+ cells and CD34+ clonogenic progenitors, confirming that the presence of CXCR4 in lipid rafts is crucial for the chemotactic response of these cells. To address this issue further, the formation of rafts in the cells was perturbed by MβCD, which depletes cholesterol from the cell membrane. The CD34+ cells were pre-incubated with MβCD for 1 hr. Chemotaxis to a low dose of SDF-1 in the presence of C3a (in the upper chambers) was evaluated. We found that pre-incubation of CD34+ cells with MβCD inhibited ~60% of the priming effect of C3a (FIG. 13, panel B).

More importantly, by employing a similar strategy, we observed that CXCR4 is present in membrane lipid rafts in UCB CD34+ cells and its association with membrane lipid rafts ceased when UCB CD34+ cells were resuspended in control medium or medium supplemented with C3a or $_{desArg}$C3a (FIG. 14). The stained cells were examined using a BX51 fluorescence microscope (Olympus America, Melville, N.Y.) equipped with a charge-coupled device camera (Olympus America). Separate pictures were merged using Image-Pro Plus software (Media Cybernetics, Inc., Silver Spring, Md.). Each staining was repeated three times on separate samples.

CXCR4 in Lipid Rafts Interacts/Activates Rac-1.

Furthermore, direct evidence of the effect of priming agents on CXCR4 incorporation into membrane lipid rafts was obtained from Western blot analysis of CXCR4 expression in various fractions of cell membranes isolated according to their lipid raft content (Example 2, FIG. 15A-B). We found that stimulation of hematopoietic THP-1 cells by C3a or $_{desArg}$C3a stimulates incorporation of CXCR4 into GM1-enriched membrane lipid rafts (fractions 3-5) (Example 2, FIG. 15, panel A). At the same time, we observed that priming THP-1 cells with C3a or $_{desArg}$C3a increased the incorporation of Rac-1, a small GTPase that is crucial for cell migration/adhesion, into membrane lipid rafts (not shown). Thus, C3 cleavage fragments increase incorporation of CXCR4 and Rac-1 into membrane lipid rafts, thereby promoting Rac-activation and resulting in enhanced sensitivity/responsiveness of hematopoietic cells to an SDF-1 gradient. The role of C3a in incorporation of CXCR4 into membrane lipid rafts in UCB cells and involvement of other signaling molecules to this phenomenon will be evaluated in Aim 1.

C3a Enhances Homing of HSPCs to BM.

As final proof of our hypothesis and to test whether the primed cells home better to BM, we primed murine BM-derived Sca-1$^+$ and human BM- and UCB-derived CD34$^+$ cells with C3a before their transplantation into lethally irradiated mice. Sixteen hrs after transplantation, recipient mice were sacrificed and cells were recovered from their marrow cavities. These cells were subsequently assayed in: 1) in vitro clonogenic assays for the number of clonogenic murine and human CFU-GM that homed to the BM of BALB/C and fNOD/SCID mice, respectively; and 2) for the number of murine CFU-S that form day-12 colonies in the spleens of lethally irradiated secondary recipients. Example 2, FIG. 16A-B shows that murine CFU-GM and CFU-S (Panel A) and human CFU-GM (Panel B) homed better into the BM of lethally irradiated recipient mice when they were preincubated with C3a for 30 min before transplantation. Of note, no CFU-GM and CFU-S were recovered from the femurs of lethally irradiated control animals that did not receive hematopoietic cells Cationic Peptides Released from Granulocytes Enhance Responsiveness of HSPCs to SDF-1 Gradient.

To address which factors released from granulocytes stimulated by C5a may increase responsiveness of HSPCs to SDF-1 gradient, we focused on granulocyte-derived cationic AMPs. We selected four potential candidates: lactoferrin (LF), β1-defensin, β2-defensin (β2D) and active fragment of cathelicidin (LL-37).

Example 2, FIG. 17A-B shows that LL-37 or β2D, which alone do not show chemotactic activity (data not shown), enhance/prime migration of murine bone marrow mononuclear cells (FIG. 17 panel A) and CFU-GM (FIG. 17 panel B) to low doses of SDF-1. To our surprise, this LL-37 and β2-defensin "priming" effect was several times higher as those described by us previously for C3a (15-17). Preliminary data show that similar phenomenon occurs for human UCB-derived cells (not shown).

Since enhanced responsiveness of HSPCs to SDF-1 gradient in the presence of C3a (priming effect) is mediated by incorporation of CXCR4 into membrane lipid rafts, we tested if similar phenomenon is responsible for LL-37 or β2D-dependent priming. FIG. 10 panel A shows that both LL-37 or β2D are also able to increase incorporation of CXCR4 into membrane lipid rafts. This was subsequently confirmed in chemotactic assays after perturbation of lipid raft formation by exposure of cells to cell membrane cholesterol-depleting agent methyl-β-cyclodextran (MβCD). FIG. 18 panel B shows that exposure of cells to MβCD inhibited LL-37-enhanced responsiveness to SDF-1 gradient. In control experiments this pretreatment did not affect N-Formyl-L-methionyl-L-leucyl-L-phenylalanine (fMLP) mediated migration (data not shown), which use G-protein dependent but non-lipid raft associated fMLP receptor.

Example 3

Cell Cycle Regulation and Th1/Th2 Cytokine Profile UCB Graft CD4 T-Cells

Our laboratory group and other investigators have identified characteristics unique to UCB naïve CD4 T-cell regulation, which have been confirmed in CD4$^+$CD45RA$^+$ T-cells, including: 1) a lack of NFAT1 protein expression in resting CD4$^+$CD45RA$^+$ T-cells and delayed up-regulation during primary antigen stimulation; 2) muted Th1/Th2 cytokine response and maintained IL-2 during primary stimulation; 3) higher basal proliferation of UCB T-cells; and 4) rescue of NFAT1 protein expression and promotion of a Th1 cytokine response in UCB CD4 T-cells treated with exogenous IFN-γ. Without wishing to be bound by any particular theory, it is hypothesized herein that the maturation and functionality of UCB CD4 T-cells responds differently to primary antigen CD3/28 co-stimulation vs. adult, and these differences may have relevance to UCB CD4 Th0 T-cell differentiation (Th1, Th2, Th17, Treg), that may ultimately contribute to UCB allogeneic tolerance observed in clinical reports to date. Preliminary data presented below is focused initially on: A) unique cytokine phenotype and proliferative functionality of UCB CD4$^+$ T-cells compared to adult, moving to B) it's unique transcription factor regulation including NFAT1 translation control by miRNA, higher UCB CD4$^+$/45RA$^+$ BACH2 expression and it's regulation of IL-2, potentially contributing to C) altered Treg maturation and function during short-term in vitro culture. Cells can be treated or transfected with the synthetic precursor miR-184 (Ambion, Catalog #1700 to specifically target and knockdown miR-184.

Lack of NFAT1 Protein in Unstimulated UCB CD4 T-Cells.

We have observed consistent and reproducible significantly reduced expression of NFAT1 protein in more than 500 experiments performed since 1999 analyzing resting UCB CD4 T-cells, and slow up-regulation during primary stimulation up to 96 h as we initially reported in 1999 in *Blood* (Kadereit et al., 1999, Blood, 94:9:3101). Lack of NFAT1 expression was not associated with the predominantly naïve CD45RA$^+$ phenotype of the UCB graft T-cells, as CD45RA$^+$ T cells expressed NFAT1 protein levels are equivalent to memory CD45RO$^+$ T cells. Interestingly, publication of subsequent gene array analyses demonstrated no difference in NFAT1 mRNA expression comparing UCB and adult T cells indicating differing post-transcriptional regulation.

Higher Rates of Proliferation in UCB T-Cells as Compared to Adult.

T-cells isolated from NFAT1 gene deleted mice demonstrate markedly increased proliferation in the absence of any external stimulation [7]. We measured proliferation in absence of stimulation in human UCB T-cells, and noted that after 24 h culture, UCB proliferation was significantly greater than adult (2870±603 cpm for UCB vs. 225±47 cpm for adult) (FIG. 20). 0.2×10$^6$ T-cells were plated in triplicate and pulsed with 1 µCi of $^3$H-thymidine (Amersham, Buckinghamshire, UK), cultured for 24 h in 96-well plates, and harvested onto glass fiber filtermats (Wallac, Turku, Finland) using a Harvester 96 (Tomtec Inc., Hamden, Conn.). Incorporated $^3$H-thymidine was measured using a MicroBeta Trilux scintillation counter. Reduced NFAT1 expression in human UCB T-cells was associated with this measured increased rate of proliferation (data not shown).

UCB CD4 T-Cells have Attenuated Expression of IFN-γ, TNF-α, IL-4, and IL-5, with Maintained IL-2 During Primary Antigen (CD3/28) Stimulation.

NFAT1 is known to be crucial for expression of inflammatory Th1 cytokines and other immunomodulatory proteins as evidenced by NFAT1-gene deleted mice. As NFAT1 protein is expressed at reduced levels in UCB, we performed microarray analyses of selected CD4 T-cells from UCB and adult during primary stimulation and queried the microarray dataset generated for genes known to be dependent on NFAT1. UCB CD4 T-cells exhibited reduced Th1 and Th2 expression with the exception of IL-2 (see Example 3, Table 1) during primary antigen (CD3/28) co-stimulation.

Example 3

Table 1

TABLE 1

UCB vs. Adult CD4 NFAT dependent genes

| Th1 cytokines | | | | Th2 cytokines | | |
|---|---|---|---|---|---|---|
| | 0 hr | 6 hr | 16 hr | | 0 hr | 6 hr | 16 hr |
| IFN-γ | −2.14 | −10.56 | −9.19 | IL4 | — | −6.50 | −3.73 |
| IL-2 | — | — | — | | | −8.00 | −4.00 |
| TNF-α | — | −2.46 | — | IL5 | — | −17.15 | −8.00 |

Rescue of IFN-γ Expression in UCB T-Cells after IFN-γ-Induced Upregulation of NFAT1.

Earlier publications showed that NFAT1 expression in T-cells is dependent in part on the presence of IFN-γ during primary stimulation, as blocking of IFN-γ blunts NFAT1 protein and mRNA upregulation. Conversely, addition of exogenous IFN-γ during stimulation resulted in increased expression of NFAT1; however rescue of NFAT1 expression in UCB T-cells in these experiments incorporating mitogen stimulation rather than CD3/28 antigen stimulation, was dependent on the presence of monocytes, as the addition of IFN-γ during stimulation of purified UCB T-cells did not result in an increase of NFAT1 expression.

To further test expression and regulation, exogenous IFN-γ was added (100 or 1,000 U/ml) during mitogen stimulation and cytoplasmic IFN-γ expression in UCB T-cells was measured. When exogenous IFN-γ was added, percentages of IFN-γ-expressing T-cells nearly increased to that measured in adult T-cells, rapidly within 24 h stimulation (Example 3, FIG. 21A-C). This rescue effect was specific for IFN-γ, as addition of TNF-α or IL-2 did not result in up-regulation of IFN-γ expression. Importantly however, the rescue-effect on IFN-γ expression in UCB T cells depended on up-regulation of NFAT1, as shown by dual staining for NFAT1 and IFN-γ (FIG. 21A-C). IFN-γ expression was only observed in NFAT1 co-expressing T-cells. Moreover, only the combination of mitogen (ConA) stimulation and addition of exogenous IFN-γ resulted in strong increases of NFAT1 expression and concomitant IFN-γ expression within the same cells, while treatment with IFN-γ alone did not stimulate IFN-γ expression and only slightly increased NFAT1 expression. Stimulation with mitogen alone resulted in increase in NFAT1 up-regulation, with only a slight increase in IFN-γ expression Rescue of NFAT1 and Reduction miR-184 Expression in UCB CD4 Treated with IFN-γ.

To test the hypothesis that NFAT1 up-regulation during primary antigen stimulation of UCB CD4 T-cells may be dependent on IFN-γ, we have conducted new experiments and show here that by supplementing with exogenous IFN-γ during CD3/28 antigen stimulation in the absence of monocytes, increases in NFAT1 protein expression is observed. In addition to increases in NFAT1 protein, we observed a marked decrease in miR-184 (FIG. 22A-B). These results were confirmed in UCB vs. adult selected CD4$^+$CD45RA$^+$ T-cells (data not shown).

Adult CD4$^+$CD45RA$^+$ T-Cells Lack Expression of BACH2 in the Presence of Normal NFAT1 Expression.

Examination of our prior gene array data showed that BACH2, a bZIP transcription factor with no previously known function in adult human T-cells was up-regulated compared to adult CD4 T-cells. Western blot confirmed absence of BACH2 in adult CD4 T-cells with normal NFAT1 protein expression. These differing BACH2 expression levels comparing UCB vs. adult were confirmed in selected CD4$^+$/45RA$^+$ T-cells (FIG. 23A-B).

Loss of BACH2 Expression Results in Reduced IL-2 Expression in UCB CD4$^+$/45RA$^+$ T-Cells.

Our work and others has demonstrated that upon activation, UCB CD4 T-cells express reduced levels of TNF-α and IFN-γ while maintaining equivalent IL2 levels as compared to adult controls. Our prior gene array analyses detected increased expression of BACH2, a bZIP transcription factor in UCB CD4 and CD4$^+$/45RA$^+$ T-cells, which was validated by qRT-PCR and Western blot. We therefore performed cross-linking chromatin immunoprecipitation (ChIP), and observed that BACH2 binds to the proximal promoter of IL-2. Next, we performed transient transfection of BACH2 siRNA in UCB CD4$^+$/45RA$^+$ T-cells which demonstrated significant reductions in IL-2 production (FIG. 24A-C). To confirm whether BACH2 was indeed functional, we measured human IL-2 promoter-controlled luciferase activity which confirmed decrease in IL-2 gene transcription in UCB CD4$^+$/45RA$^+$ T-cells transfected with BACH2 siRNA. Thus, BACH2 maintains IL-2 production when NFAT1 protein is reduced, potentially impacting UCB graft CD4$^+$/45RA$^+$ T-cell differentiation during primary antigen stimulation. FIG. 24A-C demonstrates 140 fold loss of IL-2 in mRNA expression and undetectable IL-2 protein in UCB CD4$^+$/45RA$^+$ T-cells treated with BACH2 siRNA.

miR-184 Regulation of NFAT1 in UCB CD4$^+$ T Cells.

With no differences in NFAT1 mRNA expression detected in microarray analyses comparing UCB and adult T-cells, this provided basis for the hypothesis that regulation of NFAT1 expression might be post-transcriptional, translational or post-translational. As specific miRNAs have also been implicated in T-cell differentiation, we conducted a search to determine miRNAs that may contribute to the observed differing UCB NFAT1 translational regulation.

Predicted miRNA regulators were determined by querying the Sanger miRBase registry. Briefly, this system uses the miRanda algorithm to determine and score sites of complementarity between mRNA 3' UTR sequences and known miRNA species. Predicted interactions are favored which exhibit a high degree of complementarity at the 5' end of the miRNA, and occur in UTR sequences conserved across multiple species. Many candidate miRNA sequences predicted to act on the 3' UTR of NFAT1 were identified (See the Sanger website in the UK). Of the 30-50 predicted micro-RNA binders (depending on the mRNA variant) identified with review of this data, the strongest predicted binder to the 3' UTR (both variants) was hsa-miR-184 (FIG. 25). Reference to NM__012340 in the figure is the reference number for NFATC2 mRNA, variant 1. Reference to NM__173091 in the figure is the reference number for NFATC2 mRNA, variant 2. Conversely, the strongest naturally-occurring sequence predicted to be targeted by hsa-miR-184 (based on it's sequence) is in the NFAT1 3' UTR.

miR-184 Expression in UCB vs. Adult CD4$^+$ T-Cells.

If hsa-miR-184 regulates translation of NFAT1 specifically in UCB naïve CD4$^+$ T-cells, we hypothesized that hsa-mir-184 would be more highly expressed in UCB CD4 T-cells compared to adult. Unstimulated CD4 T-cell lysates were enriched for small RNAs with the Sigma MISSION™ Small RNA isolation kit. RT-PCR was carried out with specific hairpin TaqMan™ RT primers for hsa-miR-184 (Applied Biosystems). FIG. 26 outlines that UCB CD4 T-cells express between 20 and 50 times more hsa-miR-184 than adult CD4+ cells. Results were confirmed in UCB vs. adult selected CD4+ CD45RA+ T-cells (data not shown).

FIG. 27A-B: Western Blot and RT-PCR Analysis of NFAT1 Following Transfection of Decoy Sequence to hsa-miR-184.

To determine whether the endogenous activity of miR-184 can directly repress NFAT1 protein quantity in UCB CD4 T-cells, we performed Western blot for NFAT1 on selected UCB CD4 T-cells following transfection with either control or blocking antisense to miR-184. We then quantified blot bands relative to β-actin and compared relative NFAT1 quantity under the influence of each treatment. Aggregate data reveal an 86% increase in NFAT1 protein expression when UCB CD4 T-cells were treated with antisense to miR-184. Likewise, when unstimulated adult CD4 T-cells are transfected with a synthesized precursor to miR-184, NFAT1 protein levels are reduced by approximately 31%. These experiments indicate negative regulation of NFAT1 protein by miR-184 and further suggest a non-degrading mechanism of action. Results were confirmed in UCB vs. adult selected CD4+CD45RA+ T-cells (data not shown).

Summary.

This example delineates the unique post-transcriptional regulation of NFAT1 by both mir-184 and exogenous IFN-γ in UCB CD4 T-cells. NFAT1 protein deficiency results in a lack of a strong Th1 response upon primary stimulation with the exception of IL-2 expression, unless antigen stimulation occurs in the presence of excess IFN-γ.

Loss of BACH2 Expression Results in Reduced Fox3 Expression in UCB CD4+/45RA+ T-Cells.

UCB CD4+/45RA+ T-cells were transfected with BACH2 siRNA or scrambled control siRNA. 24 h post-transfection an aliquot of cells was harvested (resting), and the remaining cells were stimulated with anti-CD3/CD28 antibodies for 6 h. Relative mRNA expression of BACH2, NFAT1, and IL2 was compared between BACH2 siRNA treated and control siRNA treated UCB CD4+/45RA+ T-cells (see FIG. 28A-B). Results revealed an average 40 fold decreases in FoxP3 mRNA in BACH2 siRNA-treated UCB CD4+/45RA+ T-cells. Error bars represent SEM [**=(p<0.002)]. To confirm protein expression CD4+/45RA+ T-cells from UCB (n=3) were treated with BACH2 siRNA (+) or control siRNA (−). Whole cell lysates from BACH2 siRNA and control siRNA treated UCB CD4+/45RA+ T-cells were analyzed for BACH2 and FoxP3 by Western Blot. BACH2 protein expression was undetectable in BACH2 siRNA treated UCB CD4+/45RA+ T-cells and FoxP3 was reduced. BACH2 siRNA knock down had no effect on NFAT1 mRNA expression.

FIG. 29A-B: Induced CpG Demethylation Increases miR-184 Expression in AB CD4+ T-Cells.

Although we have established a relationship between miR-184 expression in UCB CD4+ cells and lower expression of NFAT1 protein, the mechanism by which miR-184 expression is promoted in UCB (and conversely inhibited) in adult CD4 T-cells remains unclear. However, expression of many miRNA species is known to be mediated by epigenetic events such as DNA methylation. In fact, expression of miR-184 has previously been shown to be influenced by the methyl-CpG binding protein MeCP2 in an imprinting-associated mechanism. Indeed we observed a small predicted (obs/exp>0.6, GC>50%) CpG island upstream of the miR-184 genomic site as well as several additional downstream CpG sites (FIG. 29 A). Inhibition of demethylation-induced gene silencing is accomplished by treating with 5-aza-deoxycytidine, which is incorporated into replicating DNA and blocks DNA methyltransferase enzymes. We treated adult CD4 T-cells with 10 uM 5-aza deoxycytidine for 24 h and observed a significant increase in miR-184 expression, which was notably abrogated when cells were stimulated in vitro (FIG. 29 B).

FIGS. 30A-B and 31A-B. Transmigration of UCB MNC and CD4/45RA to SDF-1 without and with C3a Priming.

Cord blood MNC (FIG. 30A-B) isolated by Ficoll density gradient centrifugation or naïve CD4+/45RA+ T-cells (FIG. 31A-B below), isolated from MNC fractions (Miltenyi), were incubated in DMEM media with 1% human serum albumin or exposed to complement protein C3a (1 µg/ml) for 30 minutes at RT. Total UCB MNC (1×10⁵/transwell) or CD4+45RA+ T-cells (1×10⁵/transwell, purity >80%) from UCB (n=2) (FIG. 31A-B) were allowed to transmigrate (Costar Transwell plates with 5 µm pores with polycarbonate filters) to media alone (to measure random migration) or to 10 ng/ml SDF-1 for 3 h. Transmigrated cells were counted (Z Series Coulter counter) and stained with anti-CD4-PerCP anti-CD45-APC antibodies for 20 min in PBS buffer with 10% FBS prior to flow cytometric analyses on a FACS washing in PBS/10% PBS, cells were fixed in 2% paraformaldehyde prior to acquisition. All analyses utilized the BD analysis software. For analysis, either gated lymphocytes exhibiting CD45 and CD4 labeling were compared between the absence and presence of C3a priming.

Treatment of UCB MNC or selected naïve CD45+ CD4+ cells with C3a prime migration of a portion of the cell populations to a low SDF-1 gradient is also shown herein to be effective to prime the migration of CD34+ cells to SDF-1. This response may improve homing of these cell populations towards gradients of SDF-1.

Summary of Preliminary and Published Work.

Ongoing and published work underscores the fact that there are distinct phenotypic differences between normal human UCB and adult CD4+/45RA+ T-cells of potential relevance to neonatal T-cell ontogeny, which may be exploited to enhance optimal allogeneic stem cell transplantation outcomes. We have observed differing kinetics of UCB NFAT1 translation and higher expression of hsa-miR-184 in UCB CD4+/45RA+ T-cells compared to adult, and that it binds to and represses translation at it's predicted targeted sequence present on the NFAT1 mRNA. Further, we have observed that interference with the activity of hsa-miR-184 permits increased expression of the NFAT1 protein; supporting the hypothesis that hsa-miR-184 may be one important regulator of NFAT1 translational repression, ultimately contributing to the lower NFAT1 protein levels observed in UCB-derived CD4+/45RA+ T-cells and the unique immune-tolerant low Th1 cytokine profile elicited upon activation. In addition UCB CD4+/45RA+ T-cells maintain equivalent levels of IL-2 and FoxP3 to adult CD4+/45RA+ T-cells, which are required for optimal T regulatory cell development and homeostasis. Our recent published work provides insight as to normal maintained IL-2 expression mediated by the novel bZIP transcription factor BACH2, notably increased in UCB CD4+/45RA+ T-cells, thereby maintaining IL-2 production in the absence of NFAT1 normal protein levels. New exciting preliminary findings herein are that BACH2 may regulate FoxP3 in UCB CD4+/45RA+ T-cells lacking normal NFAT1 protein levels. In addition, new preliminary data is included that UCB graft naïve CD4+/45RA+ T cells treated with IFN-γ during primary antigen stimulation results in reduction in miR-184 expression and normalization of deficient NFAT1 protein expression. Further, our most recent studies have identified CpG islands upstream and immediately downstream of the mi-RNA 184 genomic site and treatment with the de-methylating agent 5-Aza-Deoxycitidine results in enhanced mi-RNA 184 expression. Finally, UCB MNC and CD4$^+$45RA$^+$ T-cells are noted to migrate to an SDF-1 stimulus.

Example 4

Age Related Changes in Vasculogenesis: Role of IL-8 and Rantes Deficiency

Limitations of current management of vascular disease includes re-occlusion and diffuse small vessel disease. Prior evidence links the level of circulating marrow-derived HSC, characterized by expression of CD133 and CD34, with the occurrence of ischemic vascular events. There is emerging evidence of age-related diminution in the number and function of marrow-derived CD34/133+ HSC in response to ischemia.

Methods

FDA-approved IND human clinical trial—trial design incorporated dose escalating CD133 autologous marrow-derived HSC for patients with a totally occluded coronary artery not amenable to standard revascularization intervention.

CD133 HSC administration—administered via coronary infusion in the vessel providing collateral blood flow.

Study population—included cardiovascular patients (median age 65+/−8 y) with at least one region of ischemic myocardium, enrolled on a phase I dose escalation study (NCT00365326) of intracoronary infusion of autologous marrow derived CD133 HSC.

Controls—controls for correlative laboratory analyses included marrow and PBMC from volunteer young adult donors (age 34+/−9 y) and newborn UCB.

All human cells were collected according to institutional IRB protocols under written informed consent.

UCB & BM MNC and isolated CD133+ HSC were tested in vitro including: colony forming unit-EC, surface phenotype for chemotactic receptors, migration to SDF-1 and VEGF stimuli, and cytokine secretion.

Results and Conclusions

Example 4, FIG. 32 schematically illustrates correlative studies of CD133 in coronary ischemia. Example 4, FIG. 33 is a table summarizing the results of a phase I clinical and provides BM cell counts, sterility results, etc. for nine subjects. Example 4, FIG. 34 graphically illustrates age and disease-related diminution in CD133 angiogenic function. Groups include umbilical cord blood, control PB, patient PB, control BM, and patient BM. Results are expressed as Number of CFUs. Example 4, FIG. 35 graphically illustrates age and disease-related diminution of CD133 angiogenic function and the expression of chemotactic receptors. Groups include CD31, CXCR4, and VEGFR2 for control BM, Patient BM and UCB. Results are expressed as Percent Surface Expression. Example 4, FIG. 36 graphically illustrates age and disease-related diminution in CD133 angiogenic function and the transmigration to SDF-1 and VEGF. Patients and controls were tested for transmigration with SDF-1, VEGF, or no treatment. Results are expressed as Percent Migration. Example 4, FIG. 37 graphically illustrates the results of an experiment studying age and disease-related diminution in CD133 angiogenic function as related to IL8 concentration. Groups include BM CD133+ Control, Patient, and CB CD133+. Example 4, FIG. 38 graphically illustrates the results of a study on age and disease-related diminution in CD133 angiogenic function and Rantes. Groups include BM CD133+ Control, BM CD133 Patient, and CB CD133+. Example 4, FIG. 39A-C, comprising three panels, graphically illustrates the results of an experiment on co-stimulatory antigen expression on UCB-derived CD133 cells. The left panel represents CD40 (FITC), CD80 (PE) and CD86 (PE). Example 4, FIG. 40 graphically illustrates the results of a study demonstrating that UCB CD133+ are defective APC and induce TH2 immune responses in MLR. Groups include IL-10, IL-5, IL-4, and IL-2. The ordinate represents Fold Change (133 stimulated/MNC stimulated) and the abscissa represent the secreted factor.

Regulatory Path for Phase I Allogeneic UCB CD133 Infusion in Coronary Ischemia— the regulatory study path disclosed herein has included initial analyses of CD133 HSC in the autologous setting, with intent to proceed to allogeneic UCB pending results of the autologous trial and further UCB pre-clinical safety and efficacy analyses. Additional pre-clinical studies are ongoing to delineate the relationship if any between CD133+ immunogenicity and vasculogenesis functionality.

These data identifying diminished angiogenic function of CD133 from advanced aged patients with cardiovascular disease, as well as pragmatic issues related to autologous cell collection, supports the concept that an allogeneic HSC source, may be optimal for wide application of stem cell therapeutics in vascular ischemia. Our current studies focus on selected CD133+ UCB-derived HSC not only to enrich this population but also to delete immune and antigen presenting cells from a MNC preparation that may exert adverse immunologic effects in a patient with an intact immune system.

It is not clear in studies to date whether microvascular vasculogenesis is mediated by: 1) direct cell-cell interactions activating cells in situ within the ischemic bed; and/or 2) paracrine cytoprotective mechanisms. However, significant anatomic incorporation of infused stem cells does not appear to be required for evident improved collateralization.

A number of inflammatory cytokines, including TNF, IL-6 and IL-8, as well as iNOS (inducible nitric oxide synthase), all components of innate immunity, are implicated in vascular ischemia. Current studies are designed to address whether the immunogenicity of UCB-derived CD133+ allogeneic HSC may be advantageous to potentially augment vasculogenesis mediated by recipient cells in situ or potentially deleterious in dampening vasculogenesis or worsening vascular ischemia via allogeneic inflammatory responses.

Example 5

Stem Cell Priming to Enhance Engraftment

This research team conducted discovery level innovative laboratory work and moved this bench work to successful enrollment of patients under a phase I/II human pilot study under FDA IND, and performed novel in vivo validation study approaches to support the clinical protocol incorporating complement C3a priming in 2 unit UCB stem cell transplantation after reduced intensity conditioning for adult patients undergoing allogeneic transplantation for management of hematologic disease.

The underlying hypothesis was that by employing C3a priming of UCB graft stem cells and CD3$^+$ T-cells, their homing and engraftment would be enhanced. Faster HSC engraftment and lymphoid reconstitution mediated by UCB CD34$^+$ HSC C3a priming was expected to generate a robust immune system in the patient and reduce life-threatening early onset infectious complications.

Priming of UCB Before Transplantation as a New Strategy to Enhance Engraftment of UCB CD34 HSC.

We hypothesized that in double UCB transplants, UCB HSCs with a better response to SDF-1 gradient would more efficiently populate hematopoietic niches in BM and engraft permanently. We tested responsiveness of UCB graft CD34+ HSC in vitro to SDF-1 gradient prior to and after C3a co-culture, and compared results of CD34+ HSC chemotaxis with rates and kinetics of UCB unit engraftment in humans.

Example 5, FIG. 41

Treatment Schema

This was a non-randomized pilot phase I/II study of the safety and efficacy of the incubation of one of two umbilical cord blood units with complement fragment 3a (C3a). After thawing, the unit with lower cryopreserved nucleated cell dose was primed with the C3a for 30 min, and infused immediately after the infusion of the unmanipulated unit. This approach was based on the fact that the larger unit offers the best chance for engraftment should the manipulation damage the 'engraftability' of the smaller unit.

Key Eligibility Criteria.

1) Patients aged 18-75 years with high-risk malignancy; 2) Availability 3 HLA 0-2 antigen (HLA-A and B at intermediate resolution; HLA-DRB1 at high resolution) mismatched unrelated UCB donor units. The two units that will compose the graft must each contain a minimum of $1.5 \times 10^7$ nucleated cells/kg each. Patient must also have a $3^{rd}$ unit (also containing a minimum of $1.5 \times 10^7$ nucleated cells/kg) which will serve as back-up in the event the primed unit fails to pass lot release criteria; 3) Adequate organ function and performance status.

Conditioning Regimen.

Patients receive cyclophosphamide (CY) 50 mg/kg×1 day (total dose: 50 mg/kg), fludarabine (FLU) 40 mg/m² daily×5 (total dose: 200 mg/m²), total body irradiation (TBI) 200 cGy in 1 fraction, equine-anti-thymocyte globulin (ATG) 15 mg/kg twice daily×3 (total dose: 90 mg/kg). All patients receive cyclosporine A (CsA) for at least 6 months and myco-phenolate mofetil (MMF) for at least 30 days. Granulocyte colony stimulating factor (G-CSF) will be started at day +1 until neutrophil recovery ≥2,500/µL for 2 days. Using this conditioning regimen, the incidence of neutrophil recovery is 92% at a median of 12 days with sustained engraftment in 83% (95% CI: 75-91%). On day 21, 40% of recipient's hematopoiesis is derived from both UCB units, but by day 100 one unit predominates with the larger CD3+ cell dose predicting which unit will predominant long-term in 68% of the time (See Figures—Example 5, FIGS. 41-48).

Stopping Guidelines:

were in place for evidence of excess: 1) infusional toxicity, 2) primary graft failure by day 42, 3) Grade III-IV acute GVHD by day 100 and transplant-related mortality at day 100.

Toxicity Monitoring:

all patients were monitored and evaluated for infusional toxicity infusion of the C3a-primed UCB unit to determine if severe acute allergic reactions occur (e.g. grade 4 toxicity except for fevers alone). Toxicity and adverse events were classified according to NCI's Common Terminology Criteria for Adverse Events V4.0.

Interim Phase I Evaluation.

To date, 22 patients have been enrolled at the site, of whom 10 were evaluated for engraftment at day +21. Median age of these patients is 58 yrs (range 21-72 yrs), median weight 79 kg (range: 48-104 kg). Male predominance has been observed: 12 patients (75%). Diagnoses include acute myeloid leukemia (9 patients), myelodysplasia (6 patients), and lymphoid malignancies (6 patients). No significant infusional adverse events have been observed with the exception of hypertension which was observed to rise to grade 3 in 5 patients (See also FIGS. 41-56, Example 5).

Correlative Studies Completed:

The SDF-1 Gradient Assay performed included: i.) C3a Co-Cultured UCB Thaw/CR-049; ii) Samples: Washed/Pre-Prime—$2 \times 10^6$ TNC; iii) Samples: Primed Cord Blood—$4 \times 10^6$ TNC; iv) *Remove RBC (Cell Lysis)—1:10 Ratio of cells to lysing solution, inc. 10 min in dark @ 37° (prepare a 1:10 dilution of lysing solution to DI $H_2O$ first); v) *Wash ×2 with Base Media (400×g/5 min); vi) *Resuspend samples to $2 \times 10^6$ NC/mL with Base Media (RPMI+0.5% HSA); vii) Equilibrate sample for 10 min @37° C.; viii)*Prepare Media/SDF-1 test reagents; ix) Equilibrate for 10 min @ 37° C.

All calculations based on output/input

Membrane seeding density=6.1E+05 NC/cm2 (200,000/ 24 well insert (0.33 cm2))

Flow procedure =CD45+ abs count

As indicated in Example 5 FIGS. 49 and 50, due to technical difficulties we were not successful in measuring interpretable data as no difference in migration of cryopreserved and thawed UCB mononuclear cells was observed comparing 3 conditions including no SDF-1, physiologic dosing 50 ng/ml, vs. high concentration of SDF-1 300 ng/ml.

Clinical Correlation Between Double UCB Transplants and Responsiveness to SDF-1 Gradient.

Analyses were performed to determine whether clinical outcome of double UCB transplants might correlate with responsiveness to SDF-1 gradient. Chemotaxis assay were performed using the transwell system as described in Aim 1 on samples obtained from UCB thawed before infusion in the recipient. UCB MNC were plated in the upper chamber and SDF-1 [50 ng/ml (low threshold dose) and 300 ng/ml (control optimal dose)] or medium alone (no SDF-1 control) were placed in the lower chambers. After chemotaxis, cells were counted by FACS as described. Cells recovered from lower chambers after chemotaxis were stained with CD34 and CD3 antibodies to evaluate the number of CD34 and T-cells. We anticipated using this chemotactic index to SDF-1 and analyze to determine correlation if any with clinical outcome of which UCB unit (e.g. C3a primed vs. unprimed) engrafts after transplantation as assessed by recipient chimerism. We anticipated that we would utilize very small samples (<5%) from thawed UCB prepared for transplants. Anticipating approximately 1 billion nucleated cells (1×10e9) at the time of thaw, 5% renders 5×10e7 nucleated cells containing approximately 40-60% T-cells, renders estimates of 20-40× 10e6 CD3+ T-cells, and at 1.0-1.4% CD34—we anticipated approximately 50,000 CD34+ HSC from each UCB graft available for laboratory analyses. These cell limitations we anticipated would not render the chemotactic assays not feasible, as these assays do not require a large number of cells (15-25K)

Impact of C3a Fragment Priming on UCB Engraftment.

These laboratory experiments were performed to evaluate responsiveness of UCB to SDF-1 gradient correlated with an outcome of injections in NOD/SCID mice to evaluate engraftment in vivo. In vivo studies incorporated humanized NOD.SCID/IL2rγ$^{null}$ (NOG) mice were conducted to assess proportions and kinetics of human HSC homing, engraftment, comparing C3a primed UCB CD34+ HSC vs. controls. NOD.SCID/IL2rγ$^{null}$ is used in our studies as these mice lack the cytoplasmic region of the IL-2Rγ and reproducibly develop human T, myeloid, NK, and B-lymphoid cells when transplanted with cord blood CD34+ cells. This model therefore provides a platform to analyze in vivo competitive repopulation of the full lymphopoietic system. We compared peripheral blood, spleen, lymph nodes, and marrow engraftment at 12 weeks with enumeration of human CD45+ cells. More mature progenitors are considered to have exhausted after 8 weeks in this NOD.SCID model and human cells present are presumed to be derived from transplanted primitive progenitor cells. HLA staining was used to determine UCB chimerism and relative contribution of C3a primed UCB CD34+ HSC to marrow engraftment.

NOD.SCID/IL2rγ$^{null}$ Repopulation Assay.

NOD/LtSz-scid IL2Rγ$^{null}$ (NOG) mice were obtained from Jackson Laboratories (Bar Harbor, Me.) and were maintained in microisolator cages under specific pathogen-free conditions and provided autoclaved food and water. We expected that responsiveness to SDF-1 gradient might provide new understanding as to UCB homing and engraftment. This could have important clinical implication for UCB engraftment in humans in this type of procedure. Further, if we observe a correlation between responsiveness to SDF-1 and engraftment in control experiments, we could enhance responsiveness of one of the units to SDF-1 by employing the priming effect, thus determining if priming will improve engraftment of the particular UCB.

Stress Environment Differentially Supports Human Hematopoietic Stem Cell Compartment Mobilization.

Methods/Results:

Both ABP (Research Blood Components, Boston, Mass.) and CBP was filtered through 0.22 μm filters to remove platelets, debris, and any cells remaining in the plasma. ABP contained 14% Citrate Phosphate Dextrose Anticoagulant (CPDA) by volume while CBP varied between 28-40% CPDA by volume. ABP samples used in migration assays were diluted to match the CBP concentration with PBS. We screened for the concentrations of 115 known proteins using a multiplexed ELISA assay and compared a pool of 10 CBPs against a pool of 10 ABPs. UCB from research units not meeting clinical cell dose threshold was kindly provided by the New York Blood Center (P. Rubinstein, MD). We found 43 proteins were elevated at least two-fold in CBP versus ABP, 16 of which were elevated 10-fold relative to ABP. Out of these 43 proteins, 6 have potential implications on HSPC mobilization: IL8, GCSF (CSF-2), VCAM, MCP1, MIP3, and CXCL10. The concentrations in pg/mL and relative increases in CBP for the proteins are: 546.85 and 19.39 fold increase for IL8; 609.91 pg/mL and 6.39 fold increase for GCSF; 1142.02 pg/mL and 4.12 fold increase for MCP1; 80.80 pg/mL and 3.48 fold increase for MIP3; 4016017.46 pg/mL and 4.20 fold increase for VCAM; and 218.27 pg/mL and 2.00 fold increase for CXCL10. The relative contribution of each protein to migration was measured by preparing aliquots of CBP and treating the aliquots with neutralizing antibodies toward each protein (Abcam, Cambridge, Mass.). Antibodies were incubated at a concentration of 1 pg/mL overnight at 4° C. Migration experiments were conducted using Transwell plates (Corning Life Sciences, Lowell, Mass.). UCB was obtained 24-48 hrs following delivery, and CBP and mononuclear cells were isolated by centrifugation through a Ficoll-Paque density gradient. UCB CD133+34+ cells were selected by magnetic labeling and sorting using AutoMACS magnetic cell sorter (Miltenyi Biotec, Auburn, Calif.). UCB HSPCs were placed in upper transwells (8.0 μm pores; $1.5 \times 10^5$ cells/well) and the lower well contained CBP, ABP, or fresh RPMI-1640 basal media as a control. The cells were allowed to migrate towards the various solutions for 3 h. Cells that migrated were counted and immunophenotyped via hemocytometer and flow cytometry (BD FACS Calibur). In a comparison of migration towards CBP vs. ABP (n=11 and 10), CBP exhibited an average increase in migration by 157.8±44.1%. Migrations towards CBP depleted of one of the 6 aforementioned proteins exhibited the following HSPC migrations compared to untreated CBP (100%) were: 48.9±17% for IL8-neutralized (n=6); 90.2±20.4% for GCSF-neutralized (n=5); 102±18.0% for MCP-neutralized (n=5); 71.7±19.8% for MIP3-neutralized (n=6); 35.4±14.7% for VCAM-neutralized (n=4); and 51.7±9.5% for CXCL10-neutralized CBP (n=4).

Figure 55A:
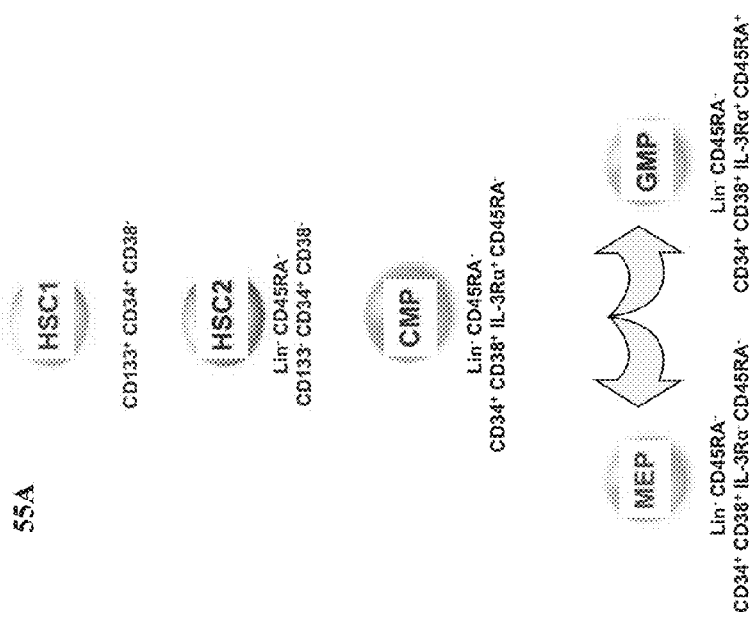
Figure 55B:
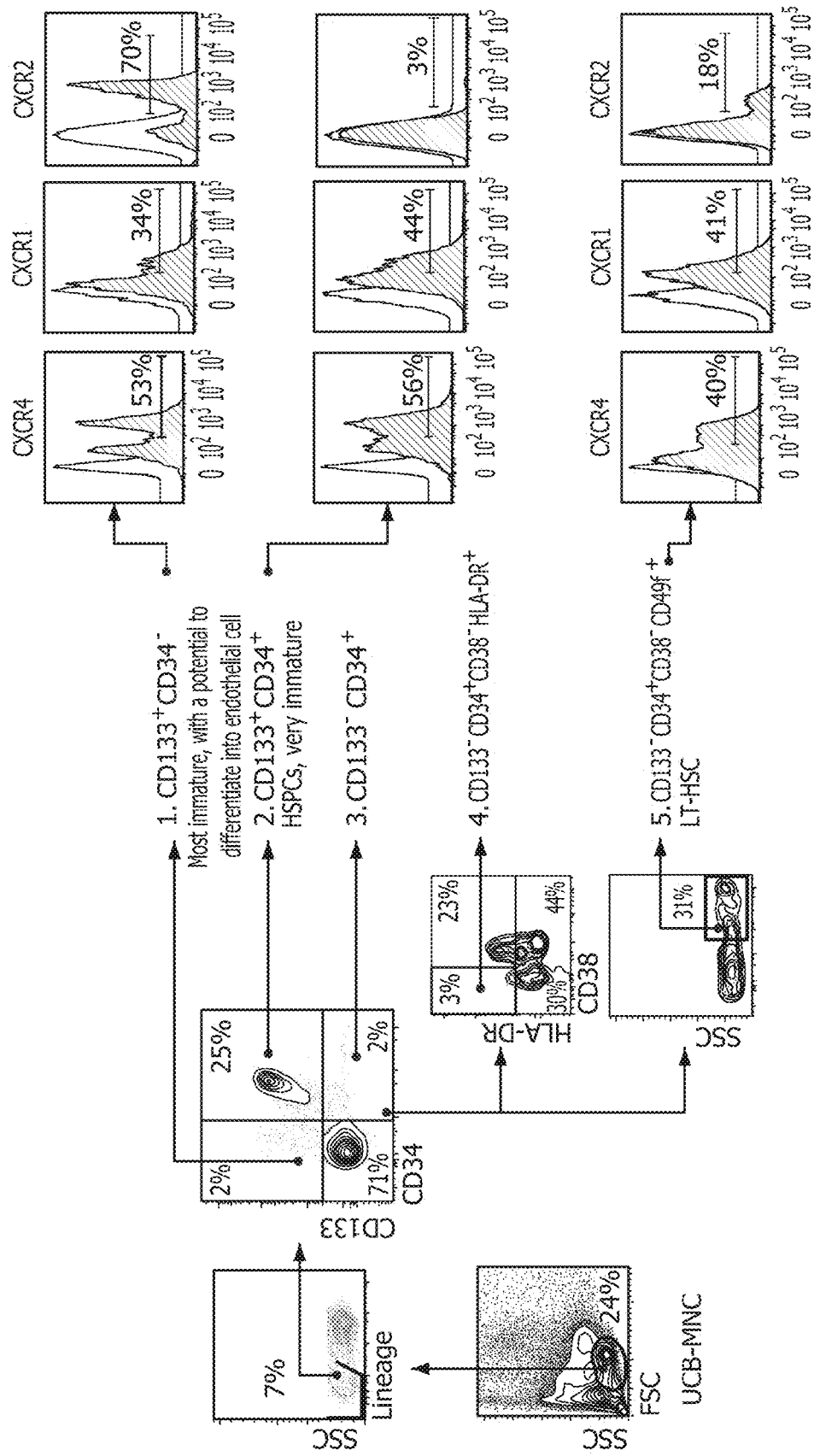

To further assess cellular and molecular mechanisms underlying UCB-HSPC migration to these identified stress-response proteins, we are using multi-parametric assays to establish the response profile of UCB-HSPC. Our current staining protocol includes more than 20 different antibodies, allowing a comprehensive picture of the complexity of HSPC. This protocol has distinct antibody set-ups that optimize the combination of fluorochrome and markers for phenotyping or functional assays. The complexity of the hematopoietic sub-populations is currently defined by protocols using six markers: CD34, CD38, CD45RA, Thy1, CD123, CD133, and the exclusion of all lineage markers (FIG. 55A). The recent characterization of CD49f (integrin α6) as a marker of long-term engrafting HSPC adds greater complexity to the analysis, thus restricting such study to very few cytometers. Protocols in our study are designed for BD LSRII/Fortessa to screen for chemokine receptors expression among HSPC subsets that display optimum response to stress stimuli (FIG. 55B). Due to the current limitations of multi-parameter flow cytometry, CXCR4, CXCR1, CXCR2, and CXCR3 must be performed separately. The simultaneous characterization of these markers on a CytoF platform will enable us to characterize new sub-populations to determine those cell populations with better short- and long-term engraftment efficiency and more rapid lineage expansion.

The heterogeneity of the HSPC subsets could be explained by stochastic, epigenetic or biochemical background. In FIG. 56, we have investigated the phospho-profile of HSC subsets to a panel of different cytokines, that these cells encounter in vivo. We have extended this approach to stress-related stimuli to better define the biochemical diversity of these cells. This approach will reveal the biochemical responsiveness of new HSPC subsets to be tested first in the NOD.SCID xenotransplantation model and ultimately in human phase I clinical trial.

Future Directions in UCB Therapeutic Angiogenesis—

Future studies include, for example, determining optimal UCB CD133 HSC cell dose in therapeutic applications including autologous and allogeneic settings. They also include delineating and optimizing relevant cytokines elicited by UCB CD133 HSC, including, but not limited to, TNF, VEGF, angiogenin, bFGF, and IL-8. Other directions including evaluating whether innate immune responses to allogeneic UCB CD133 HSC can be optimally regulated by lower infused cell dose to maintain therapeutic efficacy and to assess efficacy of directly selected vs. ex vivo expanded UCB CD133 HSC in potential therapeutic applications including central and peripheral vascular ischemia.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Brunstein, C. G., et al., Umbilical cord blood transplantation after nonmyeloablative conditioning: impact on transplantation outcomes in 110 adults with hematologic disease. Blood, 2007. 110(8): p. 3064-70.
2. Barker, J. N., et al., Transplantation of 2 partially HLA-matched umbilical cord blood units to enhance engraftment in adults with hematologic malignancy. Blood, 2005. 105(3): p. 1343-7.
3. Ballen, K. K., et al., Double unrelated reduced-intensity umbilical cord blood transplantation in adults. Biol Blood Marrow Transplant, 2007. 13(1): p. 82-9.
4. Graves, S. S., et al., Stable trichimerism after marrow grafting from 2 DLA-identical canine donors and nonmyeloablative conditioning. Blood, 2007. 110(1): p. 418-23.
5. George, T. J., et al., Factors associated with parameters of engraftment potential of umbilical cord blood. Transfusion, 2006. 46(10): p. 1803-12.
6. Nauta, A. J., et al., Enhanced engraftment of umbilical cord blood-derived stem cells in NOD/SCID mice by cotransplantation of a second unrelated cord blood unit. Exp Hematol, 2005. 33(10): p. 1249-56.
7. Komanduri, K. V., et al., Delayed immune reconstitution after cord blood transplantation is characterized by impaired thymopoiesis and late memory T-cell skewing. Blood, 2007. 110(13): p. 4543-51.
8. Cohen, G., et al., Antigen-specific T-lymphocyte function after cord blood transplantation. Biol Blood Marrow Transplant, 2006. 12(12): p. 1335-42.
9. Parkman, R., et al., Successful immune reconstitution decreases leukemic relapse and improves survival in recipients of unrelated cord blood transplantation. Biol Blood Marrow Transplant, 2006. 12(9): p. 919-27.
10. Uchida, N., et al., Umbilical cord blood transplantation after reduced-intensity conditioning for elderly patients with hematologic diseases. Biol Blood Marrow Transplant, 2008. 14(5): p. 583-90.
11. Safdar, A., et al., Infections in 100 cord blood transplantations: spectrum of early and late posttransplant infections in adult and pediatric patients 1996-2005. Medicine (Baltimore), 2007. 86(6): p. 324-33.
12. van Burik, J. A. and C. G. Brunstein, Infectious complications following unrelated cord blood transplantation. Vox Sang, 2007. 92(4): p. 289-96.
13. Szabolcs, P. and D. Niedzwiecki, Immune reconstitution after unrelated cord blood transplantation. Cytotherapy, 2007. 9(2): p. 111-22.
14. Hamza, N. S., et al., Kinetics of myeloid and lymphocyte recovery and infectious complications after unrelated umbilical cord blood versus HLA-matched unrelated donor allogeneic transplantation in adults. Br J Haematol, 2004. 124(4): p. 488-98.
15. Elfenbein, G. J. and R. Sackstein, Primed marrow for autologous and allogeneic transplantation: a review comparing primed marrow to mobilized blood and steady-state marrow. Exp Hematol, 2004. 32(4): p. 327-39.
16. Lapidot, T. and O. Kollet, The essential roles of the chemokine SDF-1 and its receptor CXCR4 in human stem cell homing and repopulation of transplanted immune-deficient NOD/SCID and NOD/SCID/B2m(null) mice. Leukemia, 2002. 16(10): p. 1992-2003.
17. Aiuti, A., et al., The chemokine SDF-1 is a chemoattractant for human CD34+ hematopoietic progenitor cells and provides a new mechanism to explain the mobilization of CD34+ progenitors to peripheral blood. J Exp Med, 1997. 185(1): p. 111-20.
18. Broxmeyer, H. E., et al., Stromal cell-derived factor-1/CXCL12 directly enhances survival/antiapoptosis of myeloid progenitor cells through CXCR4 and G(alpha)i proteins and enhances engraftment of competitive, repopulating stem cells. J Leukoc Biol, 2003. 73(5): p. 630-8.
19. Tachibana, K., et al., The chemokine receptor CXCR4 is essential for vascularization of the gastrointestinal tract. Nature, 1998. 393(6685): p. 591-4.
20. Christopherson, K. W., 2nd, et al., CD26 inhibition on CD34+ or lineage-human umbilical cord blood donor hematopoietic stem cells/hematopoietic progenitor cells improves long-term engraftment into NOD/SCID/Beta2null immunodeficient mice. Stem Cells Dev, 2007. 16(3): p. 355-60.
21. Christopherson, K. W., 2nd, et al., G-CSF- and GM-CSF-induced upregulation of CD26 peptidase downregulates the functional chemotactic response of CD34+CD38- human cord blood hematopoietic cells. Exp Hematol, 2006. 34(8): p. 1060-8.
22. Avigdor, A., et al., CD44 and hyaluronic acid cooperate with SDF-1 in the trafficking of human CD34+ stem/progenitor cells to bone marrow. Blood, 2004. 103(8): p. 2981-9.
23. Janowska-Wieczorek, A., et al., Platelet-derived microparticles bind to hematopoietic stem/progenitor cells and enhance their engraftment. Blood, 2001. 98(10): p. 3143-9.
24. Ratajczak, J., et al., Mobilization studies in mice deficient in either C3 or C3a receptor (C3aR) reveal a novel role for complement in retention of hematopoietic stem/progenitor cells in bone marrow. Blood, 2004. 103(6): p. 2071-8.
25. Reca, R., et al., Functional receptor for C3a anaphylatoxin is expressed by normal hematopoietic stem/progenitor cells, and C3a enhances their homing-related responses to SDF-1. Blood, 2003. 101(10): p. 3784-93.
26. Wysoczynski, M., et al., Incorporation of CXCR4 into membrane lipid rafts primes homing-related responses of hematopoietic stem/progenitor cells to an SDF-1 gradient. Blood, 2005. 105(1): p. 40-8.
27. Kim, Y. J. and H. E. Broxmeyer, Immune regulatory cells in umbilical cord blood and their potential roles in transplantation tolerance. Critical reviews in oncology/hematology, 2011. 79(2): p. 112-26.
28. Laughlin, M. J., et al., Outcomes after transplantation of cord blood or bone marrow from unrelated donors in adults with leukemia. The New England journal of medicine, 2004. 351(22): p. 2265-75.
29. Brown, J. A. and V. A. Boussiotis, Umbilical cord blood transplantation: basic biology and clinical challenges to immune reconstitution. Clinical immunology, 2008. 127 (3): p. 286-97.
30. Marquez-Curtis, L. A., et al., The ins and outs of hematopoietic stem cells: studies to improve transplantation outcomes. Stem cell reviews, 2011. 7(3): p. 590-607.
31. Ratajczak, M. Z., et al., A novel perspective on stem cell homing and mobilization: review on bioactive lipids as potent chemoattractants and cationic peptides as underappreciated modulators of responsiveness to SDF-1 gradients. Leukemia: official journal of the Leukemia Society of America, Leukemia Research Fund, U.K, 2012. 26(1): p. 63-72.

32. Basford, C., N. Forraz, and C. McGuckin, Optimized multiparametric immunophenotyping of umbilical cord blood cells by flow cytometry. Nature protocols, 2010. 5(7): p. 1337-46.
33. Notta, F., et al., Isolation of single human hematopoietic stem cells capable of long-term multilineage engraftment. Science, 2011. 333(6039): p. 218-21.
34. Hsu, H. C., et al., Circulating levels of thrombopoietic and inflammatory cytokines in patients with acute myeloblastic leukemia and myelodysplastic syndrome. Oncology, 2002. 63(1): p. 64-9.
35. Novershtern, N., et al., Densely interconnected transcriptional circuits control cell states in human hematopoiesis. Cell, 2011. 144(2): p. 296-309.
36. Gibbs, K. D., Jr., et al., Single-cell phospho-specific flow cytometric analysis demonstrates biochemical and functional heterogeneity in human hematopoietic stem and progenitor compartments. Blood, 2011. 117(16): p. 4226-33.
37. Weitzel et al., 2009, Blood, 113:6648-6657, microRNA 184 regulates expression of NFAT1 in umbilical cord blood CD4+ T cells.
38. Kadereit et al., 1999, Blood, 94:9:3101

What is claimed is:

1. A method for enhancing hemopoietic cell engraftment in a subject in need thereof, said method comprising contacting a population of cells comprising hemopoietic cells with an effective amount of at least one agent that enhances engraftment of said hemopoietic cells and administering said population of cells to said subject, wherein said population of cells comprising hemopoietic cells is selected from the group consisting of umbilical cord blood cells, peripheral blood cells, and bone marrow cells, wherein at least one of said at least one agents is complement protein fragment 3a (C3a) or active fragments and homologs thereof, further wherein two populations of umbilical cord blood cells are administered and each of said administered populations comprises at least $1.5 \times 10^7$ nucleated cells/kg.

2. The method of claim 1, wherein said engraftment is an allogeneic donor engraftment.

3. The method of claim 1, where said cells are umbilical cord blood CD34+ hemopoietic stem cells and CD3 T-cells.

4. The method of claim 1, wherein said population of cells comprises CD133+ cells.

5. The method of claim 1, wherein said population of cells comprises CD133+/CD34+ cells.

6. The method of claim 1, wherein said C3a comprises the sequence SEQ ID NO:1.

7. The method of claim 1, wherein said population of cells is enriched for hemopoietic stem cells, hemopoietic progenitor cells, or both hemopoietic stem and progenitor cells before being administered to said subject.

8. The method of claim 7, wherein said population of cells is enriched for CD133+ cells prior to administration to said subject.

9. The method of claim 7, wherein said population of cells is enriched for CD34+ cells prior to administration to said subject.

10. The method of claim 1, further comprising contacting said population of cells with an effective amount of at least one agent selected from the group consisting of complement protein fragment desArg3a (desArgC3a), fibronectin, fibrinogen, hyaluronic acid, soluble VCAM-1, soluble ICAM-1, uPAR, hβ2-defensin, and cathelicidin, or active fragments and homologs thereof.

11. A method for enhancing hemopoietic cell engraftment in a subject in need thereof, said method comprising contacting a population of cells comprising hemopoietic cells with an effective amount of at least one agent that enhances engraftment of said hemopoietic cells and administering said population of cells to said subject, wherein at least one of said at least one agents is complement protein fragment 3a (C3a) or active fragments and homologs thereof, wherein said population of cells is administered at a dose of at least $1.5 \times 10^7$ nucleated cells/kg to said subject, further wherein at least two different populations of cells are administered.

12. The method of claim 11, wherein said at least two different populations of cells are at least partially HLA matched.

13. The method of claim 11, wherein not all populations of cells are contacted with said agent prior to administration of said populations of cells to said subject.

14. The method of claim 13, wherein only one population of cells is contacted with said agent.

15. The method of claim 11, wherein two populations of cells are administered.

16. The method of claim 15, wherein said two populations of cells are two units of umbilical cord blood cells.

17. The method of claim 11, wherein-said population of cells comprising hemopoietic cells is selected from the group consisting of umbilical cord blood cells, peripheral blood cells, and bone marrow cells.

18. The method of claim 11, wherein when two populations of umbilical cord blood cells are administered, a first population is administered without being contacted with at least one agent that enhances engraftment and then a second population of umbilical cord blood cells is contacted with at least one agent that enhances engraftment and then said second population of cells is administered to said subject.

19. The method of 11, wherein when two populations of umbilical cord blood cells are administered, a first population is contacted with at least one agent that enhances engraftment and is then administered to said subject, and then a second population of umbilical cord blood cells is administered without being contacted with at least one agent that enhances engraftment.

20. The method of claim 11, wherein when two populations of umbilical cord blood cells are administered each population of cells is contacted with at least one agent that enhances engraftment.

21. The method of claim 11, further comprising contacting said population of cells with an effective amount of at least one agent selected from the group consisting of complement protein fragment desArg3a (desArgC3a), fibronectin, fibrinogen, hyaluronic acid, soluble VCAM-1, soluble ICAM-1, uPAR, hβ2-defensin, and cathelicidin, or active fragments and homologs thereof.

* * * * *

SEQUENCE LISTING

```
<160> NUMBER OF SEQ ID NOS: 5

<210> SEQ ID NO 1
<211> LENGTH: 77
<212> TYPE: PRT
<213> ORGANISM: Homo sapiens

<400> SEQUENCE: 1

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala Arg
65                  70                  75

<210> SEQ ID NO 2
<211> LENGTH: 76
<212> TYPE: PRT
<213> ORGANISM: Homo sapiens

<400> SEQUENCE: 2

Ser Val Gln Leu Thr Glu Lys Arg Met Asp Lys Val Gly Lys Tyr Pro
1               5                   10                  15

Lys Glu Leu Arg Lys Cys Cys Glu Asp Gly Met Arg Glu Asn Pro Met
            20                  25                  30

Arg Phe Ser Cys Gln Arg Arg Thr Arg Phe Ile Ser Leu Gly Glu Ala
        35                  40                  45

Cys Lys Lys Val Phe Leu Asp Cys Cys Asn Tyr Ile Thr Glu Leu Arg
    50                  55                  60

Arg Gln His Ala Arg Ala Ser His Leu Gly Leu Ala
65                  70                  75

<210> SEQ ID NO 3
<211> LENGTH: 22
<212> TYPE: RNA
<213> ORGANISM: Homo sapiens

<400> SEQUENCE: 3
uggacggaga acugauaagg gu                                          22

<210> SEQ ID NO 4
<211> LENGTH: 22
<212> TYPE: RNA
<213> ORGANISM: Homo sapiens
```

```
<400> SEQUENCE: 4
ugggaauagu caagaggcag gu                                              22

<210> SEQ ID NO 5
<211> LENGTH: 42
<212> TYPE: DNA
<213> ORGANISM: Homo sapiens

<400> SEQUENCE: 5
auccugguug aucuuaaugg uguccgucca aauaguaaau ag                        42
```